United States Patent
Slutsky et al.

(10) Patent No.: US 9,192,670 B2
(45) Date of Patent: Nov. 24, 2015

(54) REGULATION OF AMYLOID BETA MOLECULAR COMPOSITION FOR THE TREATMENT OF ALZHEIMER'S DISEASE

(75) Inventors: Inna Slutsky, Kfar-Saba (IL); Iftach Dolev, Tzur-Moshe (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 0 days.

(21) Appl. No.: 14/115,368

(22) PCT Filed: May 3, 2012

(86) PCT No.: PCT/IL2012/050158
§ 371 (c)(1),
(2), (4) Date: Nov. 4, 2013

(87) PCT Pub. No.: WO2012/150600
PCT Pub. Date: Nov. 8, 2012

(65) Prior Publication Data
US 2014/0074181 A1   Mar. 13, 2014

Related U.S. Application Data

(60) Provisional application No. 61/482,251, filed on May 4, 2011.

(51) Int. Cl.
*A61N 1/00* (2006.01)
*A61K 45/06* (2006.01)
*A61N 1/36* (2006.01)
*A61K 33/06* (2006.01)

(52) U.S. Cl.
CPC .................. *A61K 45/06* (2013.01); *A61K 33/06* (2013.01); *A61N 1/36025* (2013.01); *A61N 1/36082* (2013.01)

(58) Field of Classification Search
USPC ...................................... 607/45–46
See application file for complete search history.

(56) References Cited

U.S. PATENT DOCUMENTS

| | | | |
|---|---|---|---|
| 7,603,174 | B2 | 10/2009 | De Ridder |
| 2005/0021103 | A1 | 1/2005 | DiLorenzo |
| 2006/0212090 | A1 | 9/2006 | Lozano et al. |
| 2007/0135860 | A1 | 6/2007 | Tass |
| 2008/0227139 | A1 | 9/2008 | Deisseroth et al. |
| 2009/0099623 | A1 | 4/2009 | Bentwich |
| 2009/0105521 | A1 | 4/2009 | Bentwich |
| 2009/0287035 | A1 | 11/2009 | Dietrich et al. |
| 2010/0057160 | A1* | 3/2010 | De Ridder ............ 607/45 |

FOREIGN PATENT DOCUMENTS

WO    WO 2012/150600    11/2012

OTHER PUBLICATIONS

International Search Report and the Written Opinion Dated Sep. 5, 2012 From the International Searching Authority Re. Application No. PCT/IL2012/050158.

(Continued)

*Primary Examiner* — Nicole F Lavert

(57) ABSTRACT

A method of treating Alzheimer's disease (AD) is disclosed. The method comprises electrically stimulating a nerve pathway in a brain region of a subject with at least two high frequency spike bursts of electrical currents, the bursts comprising between 2-20 spikes, wherein a frequency of the spikes in the bursts is between 5-200 msec.

27 Claims, 25 Drawing Sheets
(20 of 25 Drawing Sheet(s) Filed in Color)

(56) References Cited

OTHER PUBLICATIONS

Ferrucci et al. "Transcranial Direct Current Stimulation Improves Recognition Memory in Alzheimer Disease", Neurology, 71: 493-498, Jun. 4, 2008.

Laxton et al. "A Phase I Trial of Deep Brain Stimulation of Memory Circuits in Alzheimer's Disease", Annals in Neurology, 68: 521-534, May 19, 2010.

* cited by examiner

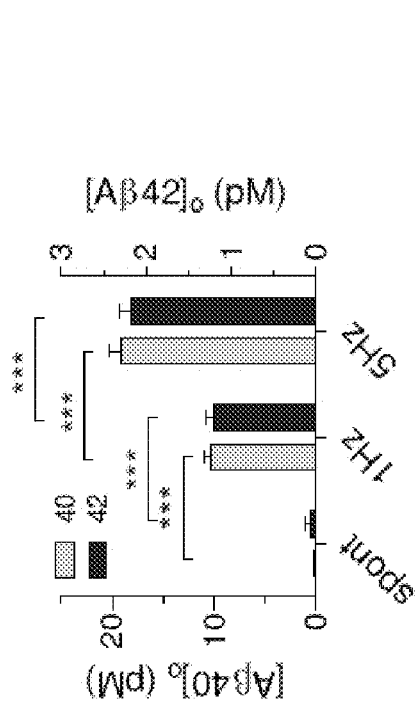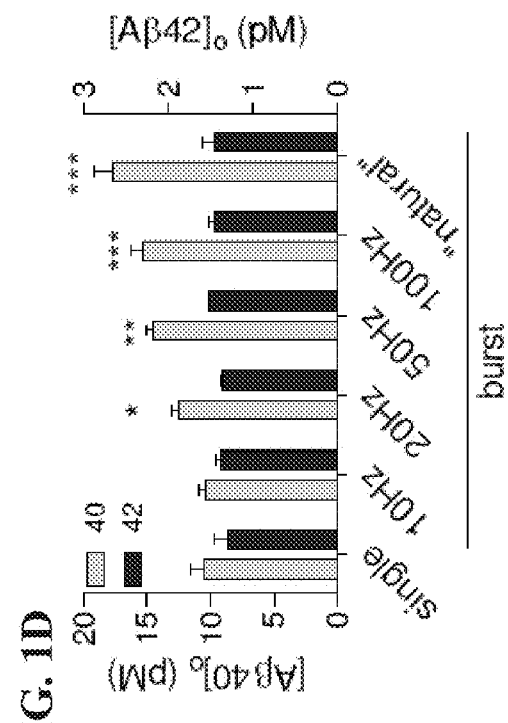

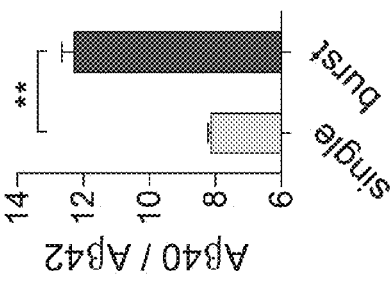
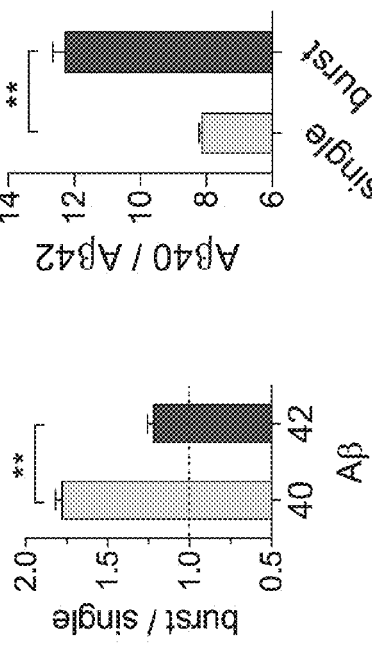
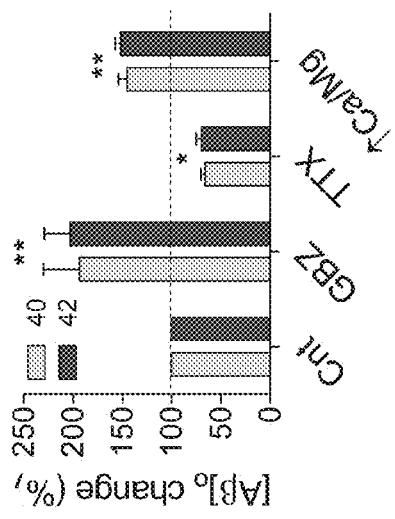
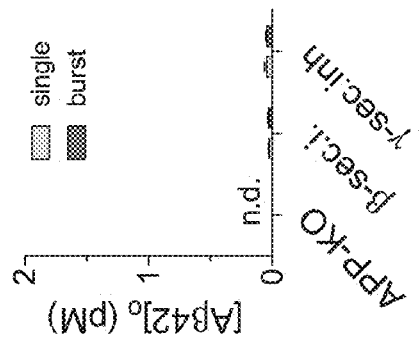
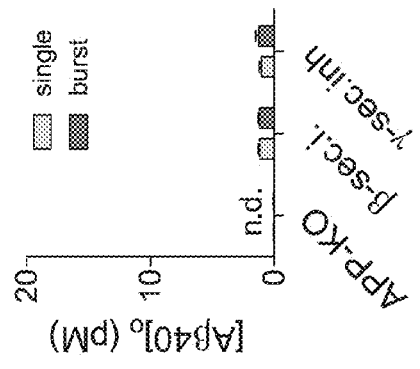

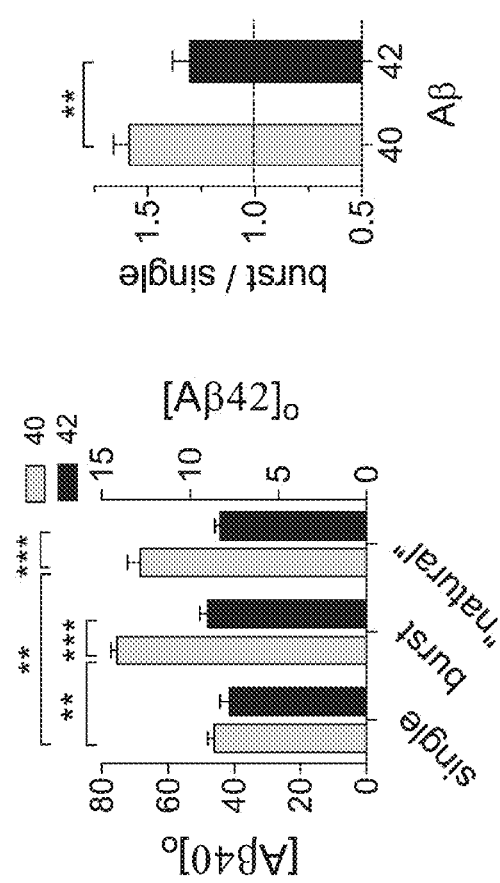
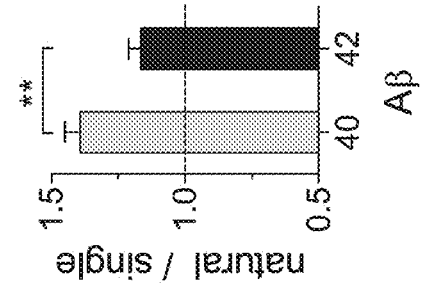
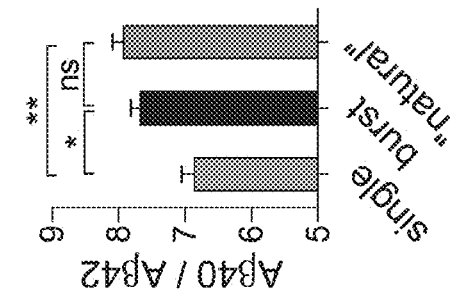
FIG. 3A  FIG. 3B  FIG. 3C  FIG. 3D

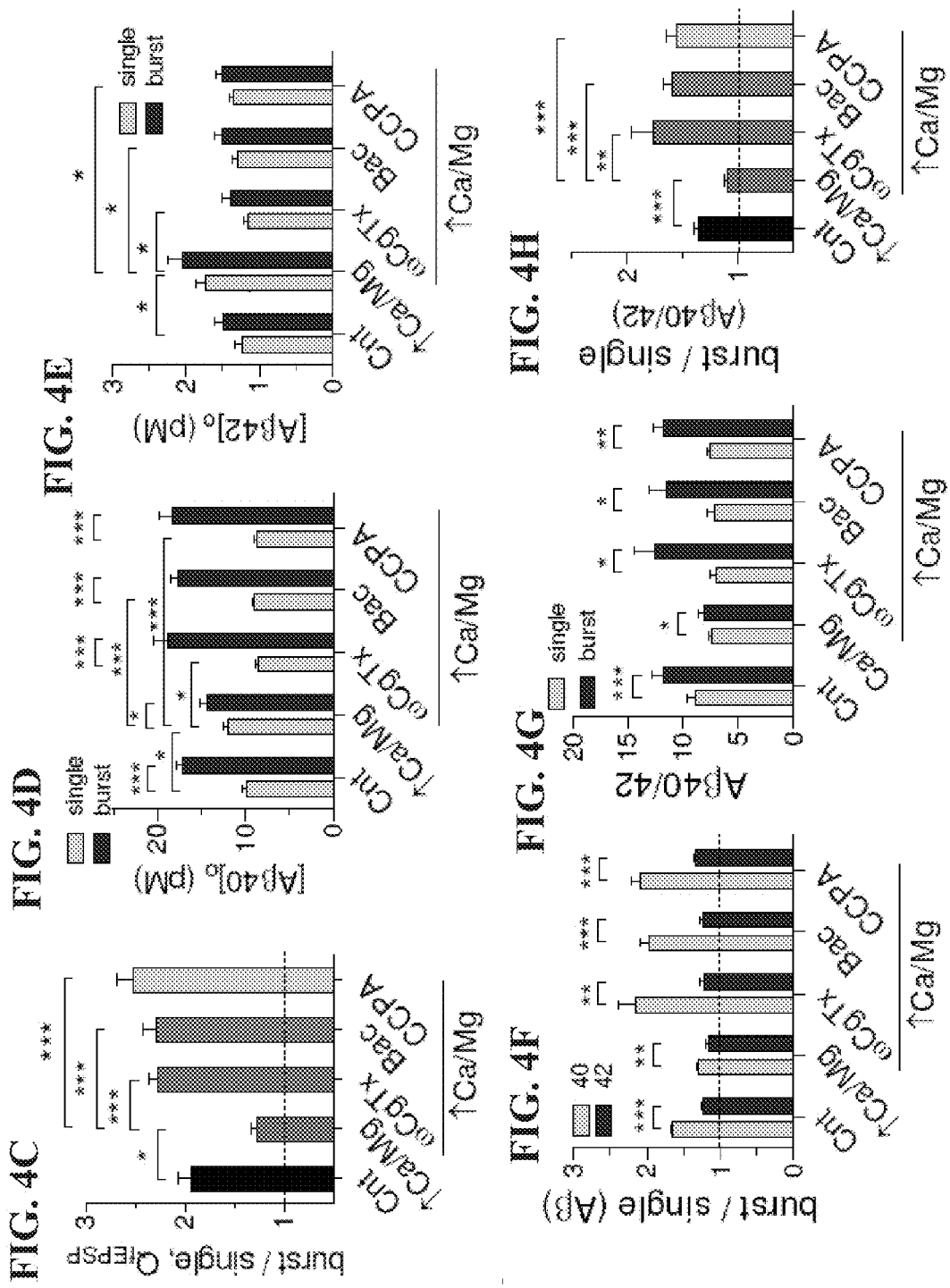

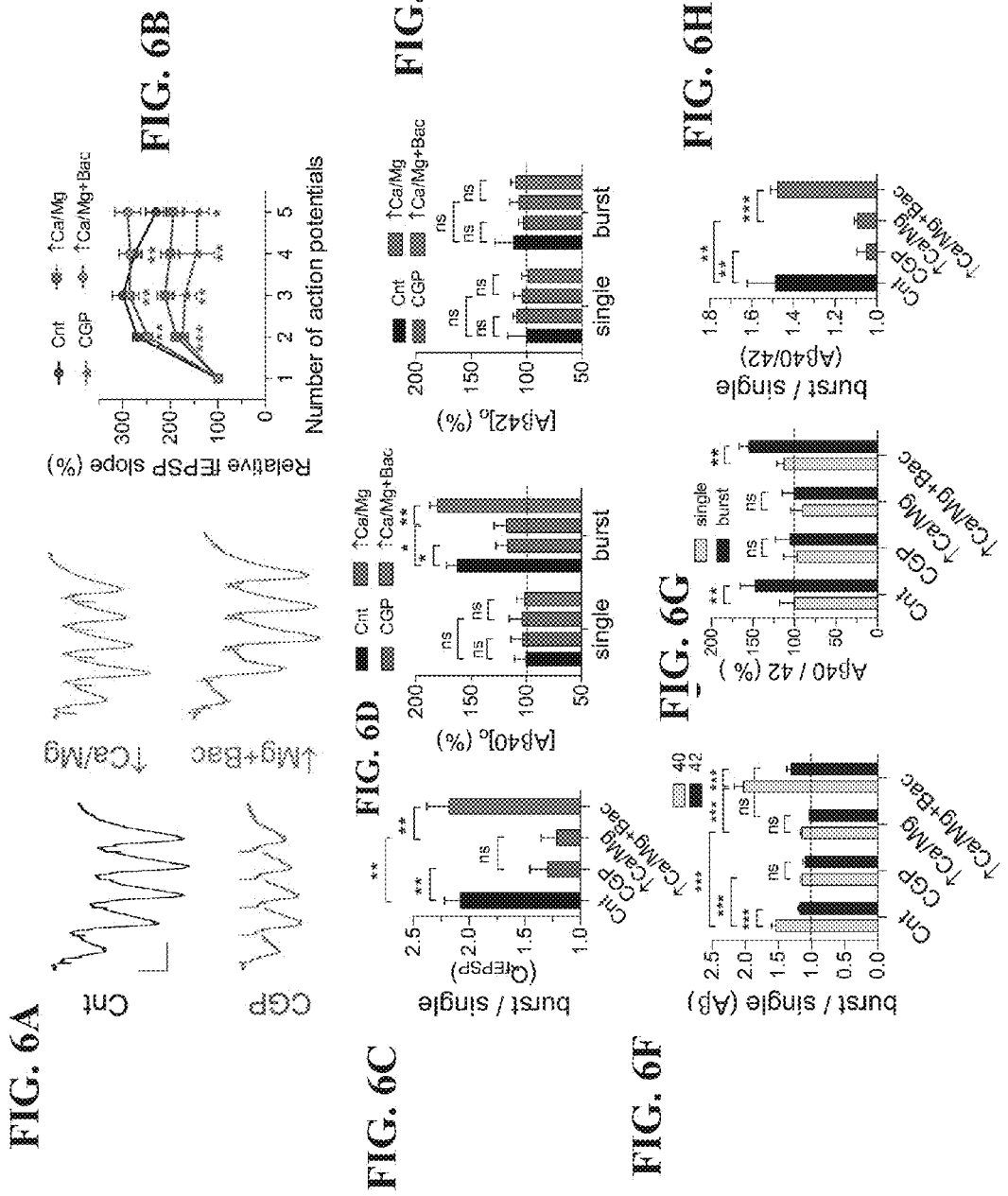

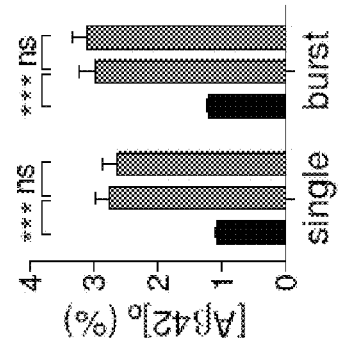
FIG. 7C
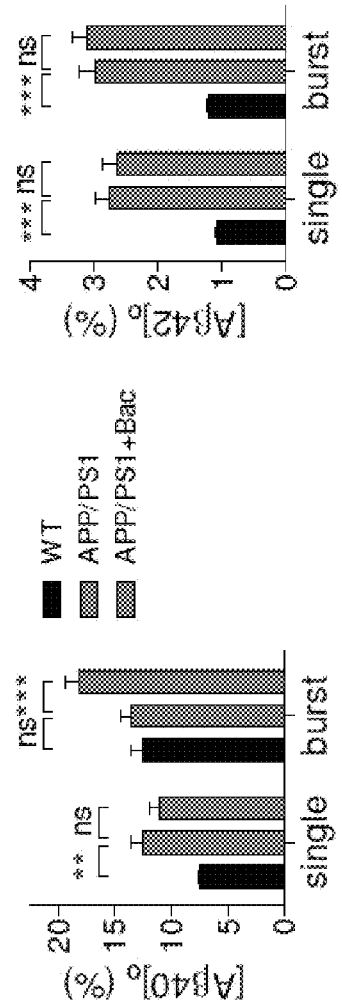
FIG. 7D
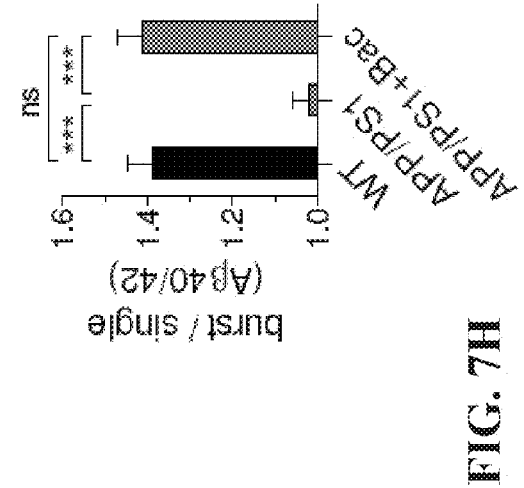
FIG. 7E
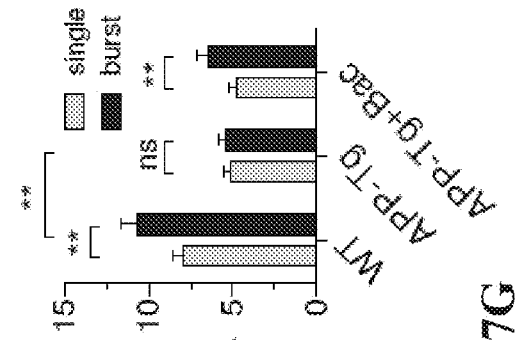
FIG. 7G
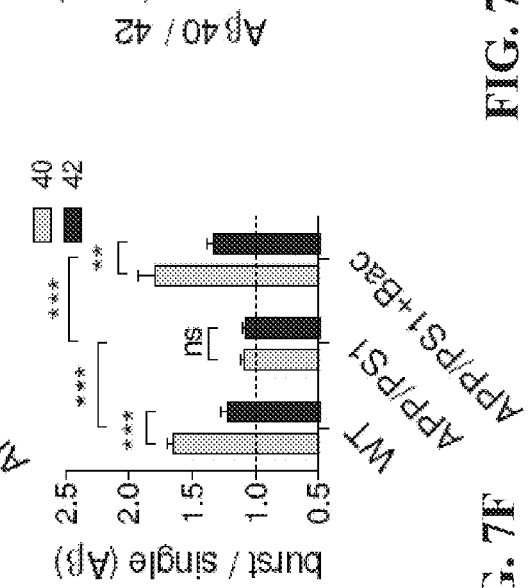
FIG. 7F
FIG. 7H

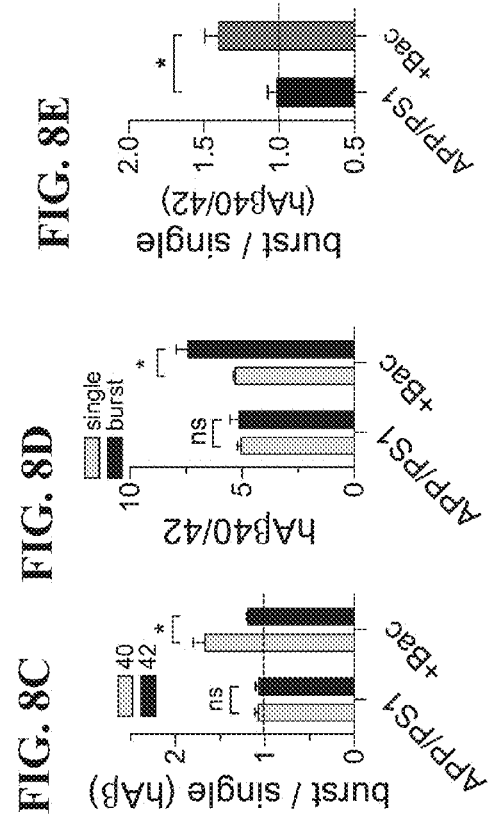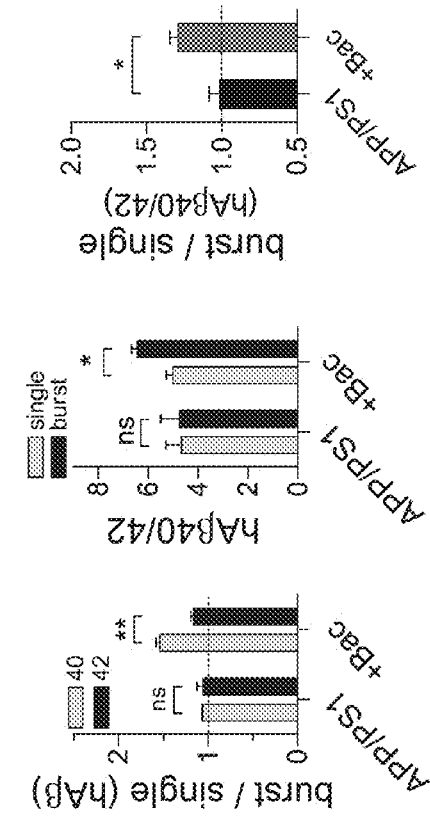

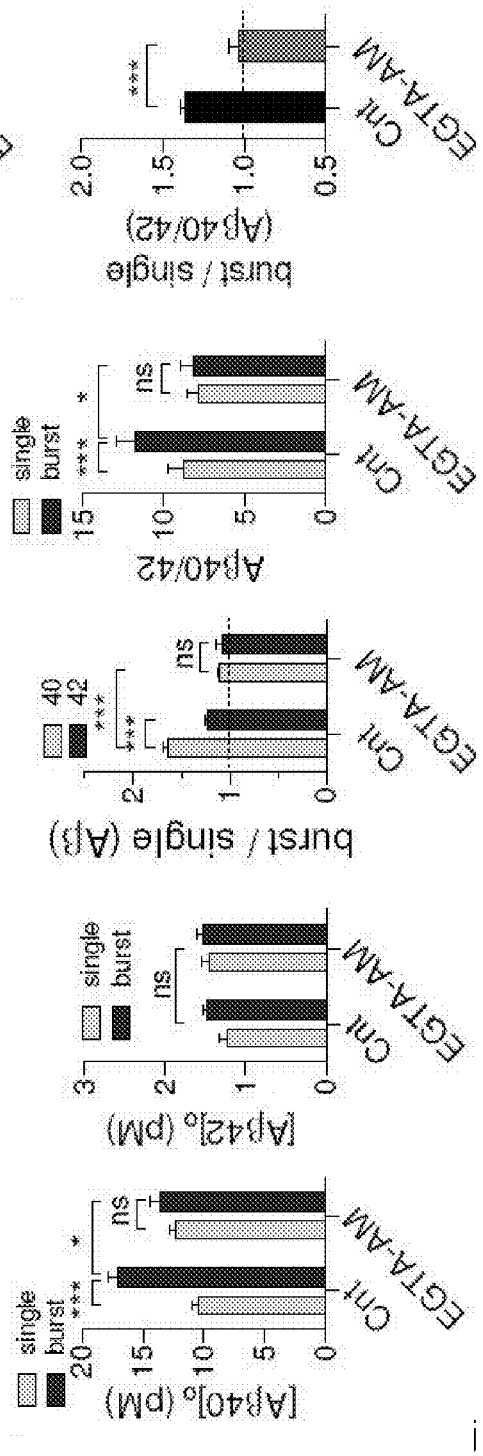

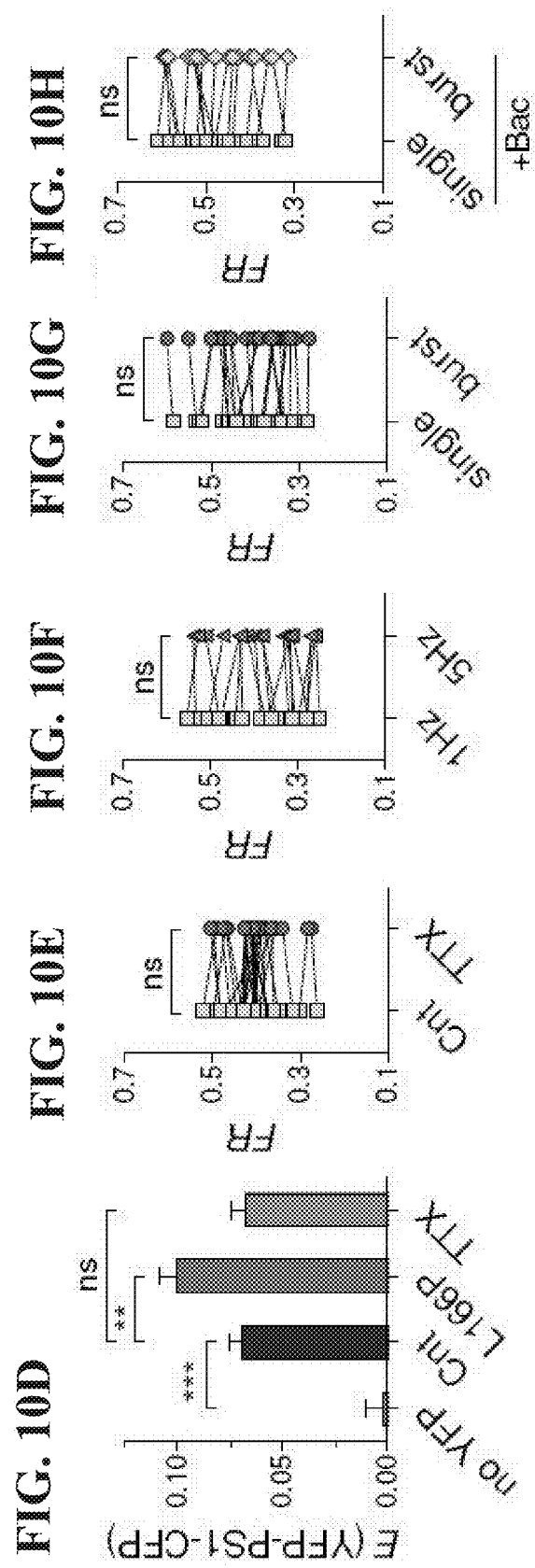

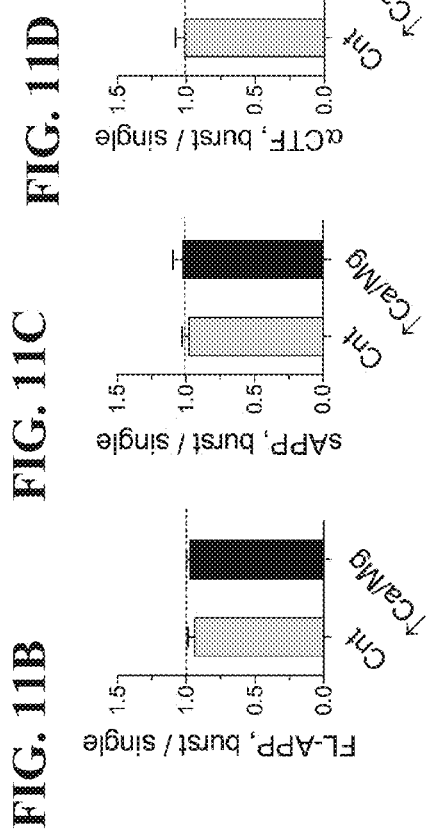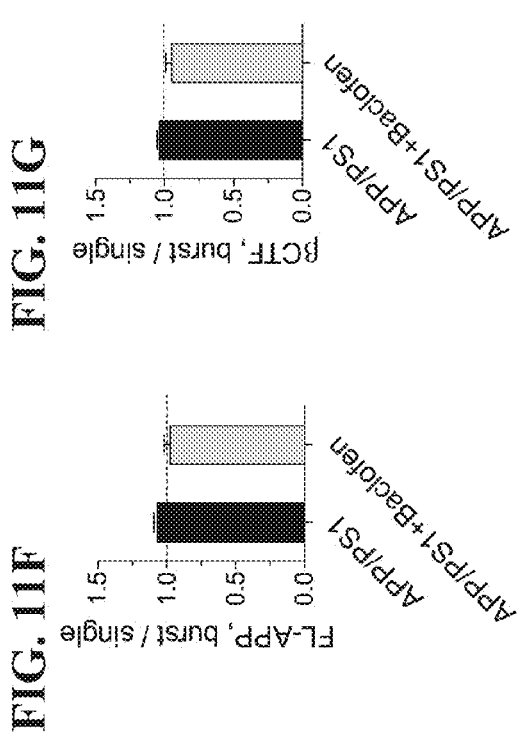
FIG. 11B  FIG. 11C  FIG. 11D
FIG. 11A
FIG. 11F  FIG. 11G
FIG. 11E

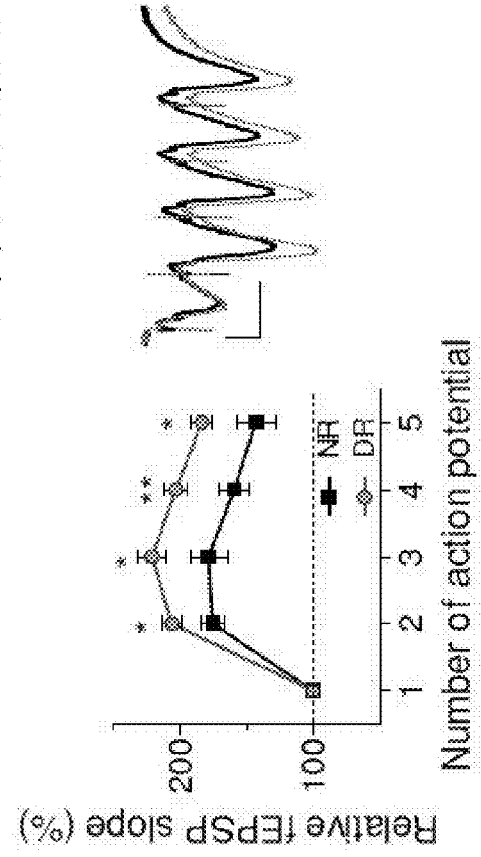
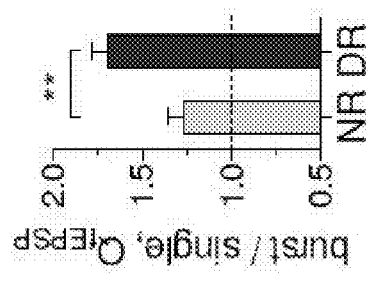
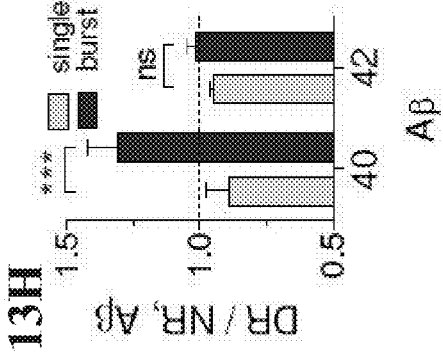
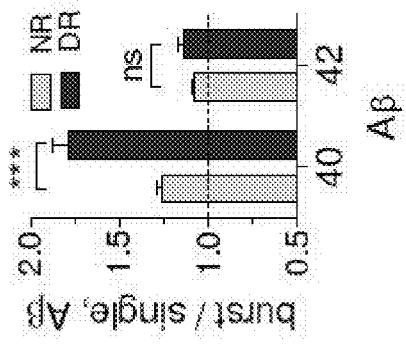
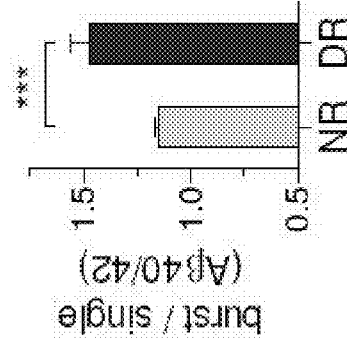
FIG. 13F  FIG. 13G
FIG. 13H  FIG. 13I  FIG. 13J

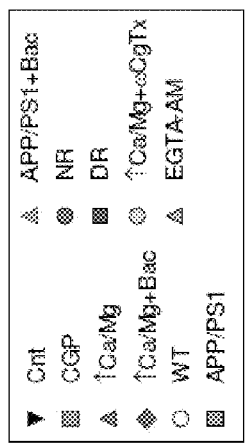
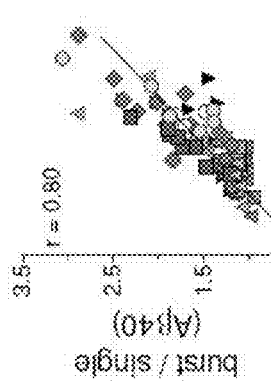
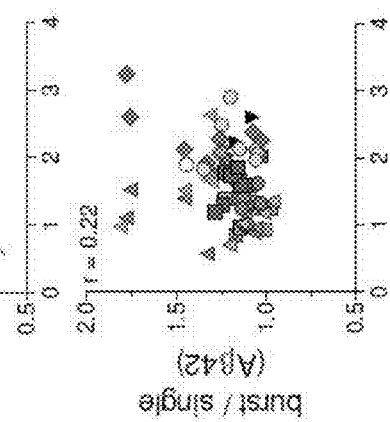
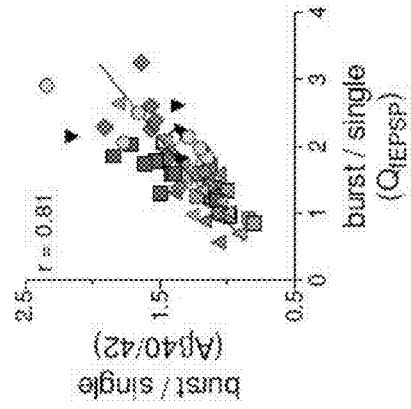
FIG. 15A
FIG. 15B
FIG. 15C

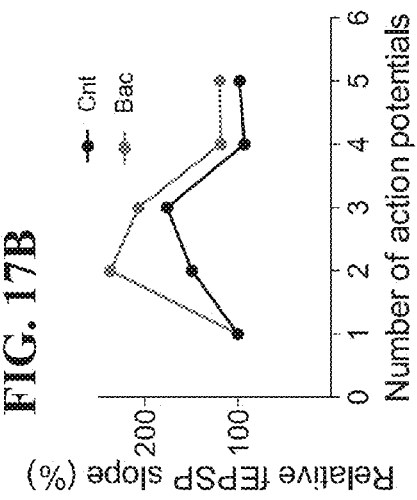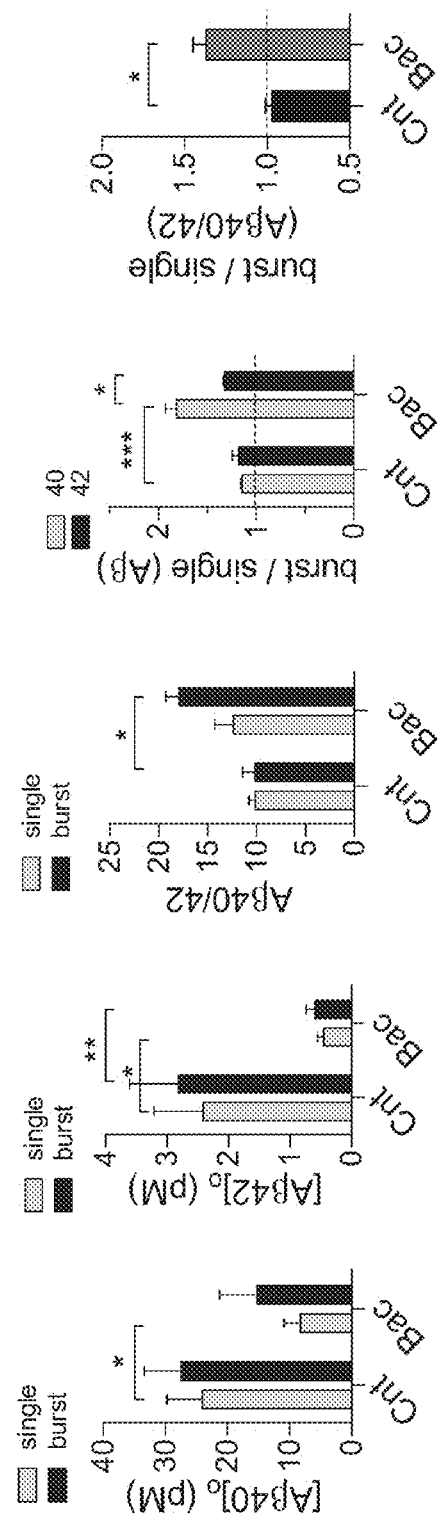
FIG. 17A  FIG. 17B  FIG. 17C  FIG. 17D  FIG. 17E  FIG. 17F  FIG. 17G

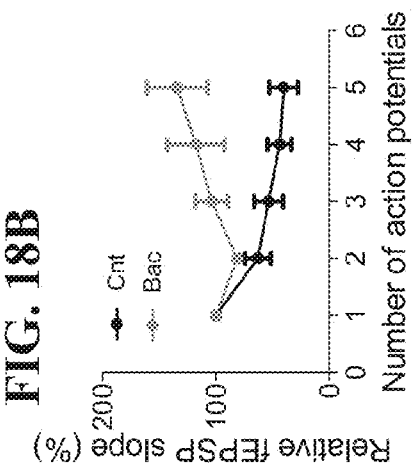
FIG. 18A
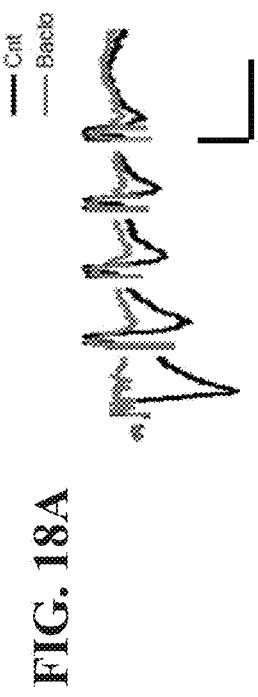
FIG. 18B
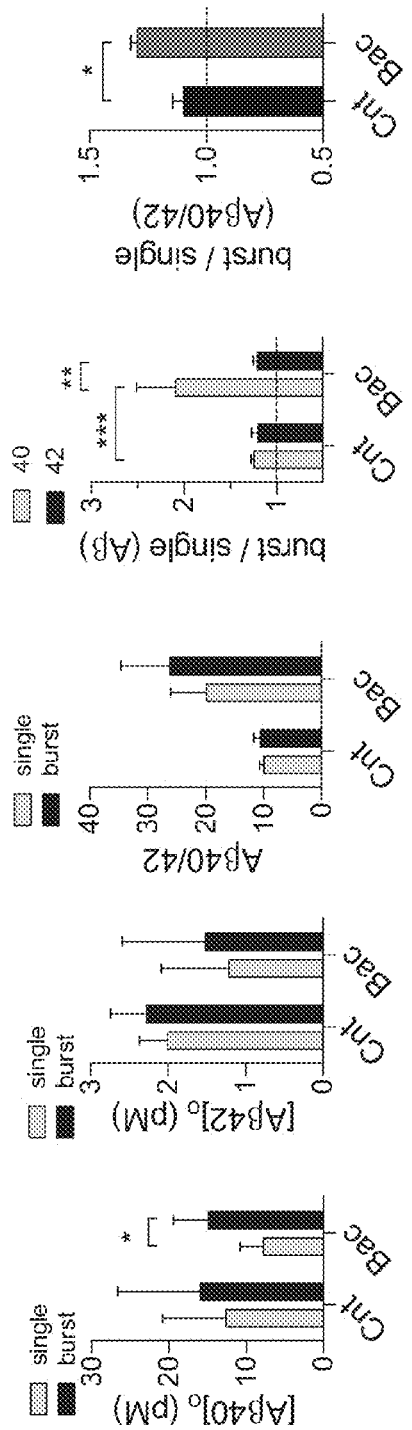
FIG. 18C
FIG. 18D
FIG. 18E
FIG. 18F
FIG. 18G

REGULATION OF AMYLOID BETA MOLECULAR COMPOSITION FOR THE TREATMENT OF ALZHEIMER'S DISEASE

RELATED APPLICATIONS

This application is a National Phase of PCT Patent Application No. PCT/IL2012/050158 having International filing date of May 3, 2012, which claims the benefit of priority under 35 USC §119(e) of U.S. Provisional Patent Application No. 61/482,251 filed on May 4, 2011. The contents of the above applications are all incorporated by reference as if fully set forth herein in their entirety.

FIELD AND BACKGROUND OF THE INVENTION

The present invention, in some embodiments thereof, relates to regulation of Amyloid-β (Aβ) molecular composition for the treatment of Alzheimer's disease (AD).

Alzheimer's disease (AD) is the most common form of both senile and presenile dementia in the world and is recognized clinically as relentlessly progressive loss of memory and intellectual function and disturbances in speech (Merritt, 1979, A Textbook of Neurology, 6th edition, pp. 484-489, Lea & Febiger, Philadelphia, which is incorporated herein by reference). Alzheimer's disease begins with mildly inappropriate behavior, uncritical statements, irritability, a tendency towards grandiosity, euphoria, and deteriorating performance at work; it progresses through deterioration in operational judgment, loss of insight, depression, and loss of recent memory; and it ends in severe disorientation and confusion, apraxia of gait, generalized rigidity, and incontinence (Gilroy & Meyer, 1979, Medical Neurology, pp. 175-179, MacMillan Publishing Co., which is incorporated herein by reference. Alzheimer's disease is found in about 10% of the population over the age of 65 and 47% of the population over the age of 85 (Evans et al., 1989, JAMA, 262:2551-2556, which is incorporated herein by reference).

It has been widely accepted that the accumulation of amyloid-β (Aβ) peptides in the brain extracellular space and alteration in Aβ molecular composition are critical for developing synaptic and cognitive deficits in Alzheimer's disease (AD). Aβ is produced by sequential limited proteolysis of the amyloid precursor protein (APP) by two aspartyl proteases, β- and γ-secretases. Proteolysis by γ-secretase is the last processing step resulting release of Aβ. Normally, γ-secretase cleavage results in 40 amino acids in length Aβ peptides (Aβ40) and smaller amount of longer, 42 amino acid species (Aβ42). Aβ42 exhibits faster rate of amyloid formation and has been proposed to "seed" Aβ40 aggregation. Small alterations in the molecular composition of Aβ, reflected by the Aβ42/40 ratio, can dramatically affect Aβ aggregation kinetics, the morphology of amyloid fibrils and synaptic function.

Elucidating factors that regulate the Aβ42/40 ratio levels is important for understanding AD pathogenesis. Genetic studies provide overwhelming evidence that mutations in genes encoding human amyloid-precursor protein (hAPP), presenilin 1 (PS1) or presenilin 2 (PS2) are associated with early-onset autosomal dominant familial AD (FAD). Many of FAD mutations trigger Aβ oligomerization and subsequent aggregation through relative over-production of Aβ42 isoform with resultant increase in the Aβ42/40 ratio. However, FAD mutations account only for 1-2% of AD cases, thus leaving the physiological mechanisms that trigger experience-dependent Aβ42/40 alternations in the most common, late-onset sporadic AD an enigma.

The use of electrical stimulation for treating neurological disease, including such disorders as movement disorders including Parkinson's disease, essential tremor, dystonia, and chronic pain, has been widely discussed in the literature. It has been recognized that electrical stimulation holds significant advantages over lesioning since lesioning destroys the nervous system tissue. In many instances, the preferred effect is to modulate neuronal activity. Electrical stimulation permits such modulation of the target neural structures and, equally importantly, does not require the destruction of nervous tissue. Such electrical stimulation procedures include electroconvulsive therapy (ECT), repetitive transcranial (rTMS) magnetic stimulation and vagal nerve stimulation (VNS).

Deep brain stimulation (DBS) has been applied to the treatment of central pain syndromes and movement disorders, and it is currently being explored as a therapy for epilepsy. For instance, U.S. Pat. Nos. 6,016,449 and 6,176,242 disclose a system for the electrical stimulation of areas in the brain for the treatment of certain neurological diseases such as epilepsy, migraine headaches and Parkinson's disease.

Ferrucci et al [Neurology, 2008, Vol 71, Pages 493-498] teaches that transcranial direct current stimulation (tDCS) over the temporoparietal areas in patients with Alzheimer disease improved recognition memory.

U.S. Patent Application No. 2006/0212090 teaches electrical stimulation of various areas of the brain including the hippocampus for the treatment of Alzheimer's.

Chronic electrical stimulation of the hippocampus for the treatment of Alzheimer's disease has now reached phase II clinical trials [Annals of Neurology, Vol. 68, Issue 4, pages 521-534].

Additional background art includes U.S. Patent Application Nos: 20090287035, 20090105521, 20090099623, 20080227139, 20070135860, 20050021103 and U.S. Pat. No. 7,603,174.

SUMMARY OF THE INVENTION

According to an aspect of some embodiments of the present invention there is provided a method of treating Alzheimer's disease (AD) in a subject in need thereof, the method comprising electrically stimulating a nerve pathway in a brain region of the subject with at least two high frequency spike bursts of electrical currents, the bursts comprising between 2-20 spikes, wherein a frequency of the spikes in the bursts is between 5-200 msec.

According to an aspect of some embodiments of the present invention there is provided a method of treating AD in a subject in need thereof, the method comprising administering to the subject a therapeutically effective amount of an agent selected from the group consisting of a $GABA_B$ receptor agonist, an $A_1$ receptor agonist, a metabotropic glutamate receptors group II agonist, an $M_2$ muscarinic agonist, a $CB_1$ endocannabinoid receptor agonist, Mu opioid receptor agonist, a voltage-dependent antagonist of voltage-gated calcium channels and a calcium chelator, wherein a dose of the agent is selected such that it lowers synaptic transmission of low frequency pulses in the brain to a greater extent than high frequency bursts.

According to an aspect of some embodiments of the present invention there is provided a method of selecting a stimulator useful for the treatment of AD, the method comprising:

(a) contacting brain cells with the stimulator; and (b) determining an amount of Aβ40 in the brain cells, wherein an increase in an amount of Aβ40 following the contacting is indicative of a stimulator useful for the treatment of AD.

According to some embodiments of the invention, a time between the at least two high frequency spike bursts is from 200 ms to 10 sec.

According to some embodiments of the invention, a membrane depolarization caused by the spikes in the bursts is between about 50-100 mV.

According to some embodiments of the invention, the brain region comprises a hippocampus.

According to some embodiments of the invention, the electrically stimulating is effected at the entorhinal cortex.

According to some embodiments of the invention, a pattern of the spikes of one burst comprises a repeating pattern.

According to some embodiments of the invention, a pattern of the spikes of one burst comprises an irregular, non-repeating pattern.

According to some embodiments of the invention, the pattern comprises a natural burst pattern of a healthy subject.

According to some embodiments of the invention, the natural burst pattern of a healthy subject is a hippocampal natural burst pattern.

According to some embodiments of the invention, the hippocampal natural burst pattern is set forth in Table 1.

According to some embodiments of the invention, the electrically stimulating does not affect the permeability of the blood brain barrier (BBB).

According to some embodiments of the invention, the electrically stimulating is effected by a method selected from the group consisting of repetitive transcranial magnetic stimulation (rTMS); transcranial direct current stimulation (tDCS) and repetitive transorbital alternating current stimulation (rt-ACS).

According to some embodiments of the invention, the method further comprises administering to the subject an agent selected from the group consisting of a $GABA_B$ receptor agonist, an $A_1$ receptor agonist, a metabotropic glutamate receptors group II agonist, an $M_2$ muscarinic agonist, a $CB_1$ endocannabinoid receptor agonist, Mu opioid receptor agonist, a voltage-dependent antagonist of voltage-gated calcium channels.

According to some embodiments of the invention, the administering is effected prior to the stimulating.

According to some embodiments of the invention, the administering is effected following the stimulating.

According to some embodiments of the invention, the administering is effected concomitant with the stimulating.

According to some embodiments of the invention, the stimulating is effected invasively.

According to some embodiments of the invention, the stimulating is effected non-invasively.

According to some embodiments of the invention, a dose of the agent is selected such that it lowers synaptic transmission of low frequency pulses in the brain to a greater extent than high frequency bursts.

According to some embodiments of the invention, the $GABA_B$ receptor agonist is selected from the group consisting of baclofen, CGP44532 and CGP35024.

According to some embodiments of the invention, the $A_1$ receptor agonist is selected from the group consisting of 2-Chloro-N-cyclopentyladenosine (CCPA), N-Cyclopentyladenosine (CPA), N-Bicyclo[2.2.1]hept-2-yl-5'-chloro-5'-deoxyadenosine (ENBA), N-[(1S,2S)-2-Hydroxycyclopentyl]adenosine, and 2-Chloro-N-cyclopentyl-2'-methyladenosine.

According to some embodiments of the invention, the metabotropic glutamate receptor group II agonist is selected from the group consisting of (1R,4R,5S,6R)-4-Amino-2-oxabicyclo[3.1.0]hexane-4,6-dicarboxylic acid (LY 379268), (1S,2S,5R,6S)-2-Aminobicyclo[3.1.0]hexane-2,6-dicarboxylic acid (LY35474), (2R,4R)-4-Aminopyrrolidine-2,4-dicarboxylate and (2S,1'S,2'S)-2-(Carboxycyclopropyl) glycine (L-CCG-I).

According to some embodiments of the invention, the $CB_1$ endocannabinoid receptor agonist is selected from the group consisting of N-(2-Chloroethyl)-5Z,8Z,11Z,14Z-eicosatetraenamide (ACEA), N-(Cyclopropyl)-5Z,8Z,11Z,14Z-eicosatetraenamide (ACPA), rel-5-(1,1-Dimethylheptyl)-2-[(1R,3S)-3-hydroxycyclohexyl] phenol (CP47497) and N-(2-Hydroxyethyl)-7Z,10Z,13Z,16Z-docosatetraenamide.

According to some embodiments of the invention, the voltage-dependent antagonist of voltage-gated calcium channels is selected from the group consisting of ω-conotoxin GVIA, magnesium chloride, magnesium threonate and magnesium chelated with the amino acids glycine and lysine.

According to some embodiments of the invention, the stimulator comprises an electrical stimulator.

According to some embodiments of the invention, the stimulator comprises a pharmacological stimulator.

According to some embodiments of the invention, the contacting is effected in vitro.

According to some embodiments of the invention, the contacting is effected ex vivo.

According to some embodiments of the invention, the contacting is effected for about 3 hours.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings:

FIGS. 1A-F illustrate differential regulation of Aβ40 and Aβ42 isoforms by temporal pattern of afferent input in acute non-transgenic hippocampal slices. (A) Stimulation conditions: (i) no stimulation; (ii) spikes delivered by field electrodes at constant frequency of 1 Hz; (iii) spikes delivered by field electrodes at constant frequency of 5 Hz. The stimulation period was 1 h for all experimental conditions. (B) Increase in the mean firing rate from 1 to 5 Hz uniformly affected $[A\beta 40]_o$ and $[A\beta 42]_o$ isoforms (n=5-7). The fraction of spontaneously-released Aβ without stimulation is negligible. (C) Stimulation conditions: (i) single spikes at constant frequency of 1 Hz; (ii) bursts consisting of 5 pulses with inter-spike-interval of 10-100 ms and inter-burst-interval of 5 s; (iii) "natural" stimulation pattern[28]. The mean stimulation rate and stimulation time were constant across different conditions (1 Hz, 1 h). (D) [Aβ40]$_o$ and [Aβ42]$_o$ measured during different stimulation patterns as described in (c). [Aβ40]$_o$ was higher during 20-100 Hz spike bursts (n=4-8) and during "natural" burst discharges (n=4) comparing to the same amount of single spikes (n=7), while [Aβ42]$_o$ did not differ between input patterns (P>0.2). (E) Pattern dependency determined by burst/single ratio was higher for [Aβ40]$_o$ than for [Aβ42]$_o$ for bursts at frequencies≥20 Hz and "natural" burst pattern (n=4-7). (F) Aβ40/42 ratio was 23% higher during 20 Hz burst (n=4), 46% higher during 50-100 Hz spike bursts (n=7) and 50% higher during "natural" bursts (n=4). ANOVA analysis with post hoc Bonferroni's multiple comparison tests indicate significance. *P<0.05, P<0.01, *P<0.001. Data represent the mean±s.e.m.

FIGS. 2A-E illustrate pharmacological manipulations perturbing spontaneous neuronal activity uniformly regulate Aβ40 and Aβ42 isoforms in rat hippocampal cultures. (A) Blocking spikes by 1 mM tetrodotoxin reduced [Aβ40]$_o$ by 34% and [Aβ42]$_o$ by 31% (TTX, n=3, *P<0.05); blocking GABA$_A$ receptors by 20 mM gabazine increased [Aβ40]$_o$ by 93.5% and [Aβ42]$_o$ by 103% (GBZ, n=3, **P<0.01); ↑Ca/Mg ratio from 1 to 1.5 resulted in increase of [Aβ40]$_o$ by 45% and [Aβ42]$_o$ by 51% (↑Ca/Mg, n=3, *P<0.01). All the treatments have been applied for 1 h at 37° C. (B) Aβ40 and Aβ42 burst/single ratio for bursts consisting of 5 AP@100 Hz with increased inter-burst interval (30 sec, n=3). (C) The Aβ40/42 ratio associated with single and burst patterns in the same experiments as in (B) (n=3). (D) [Aβ40]$_o$ measurements during single spikes and spike bursts in hippocampal slices of APP-KO mice (non detected, n=3), and slices pretreated by b-secretase (BACE1 inhibitor IV, 5 mM, n=3) or g-secretase (L-685,458, 2 mM, n=3). (E) [Aβ42]$_o$ measurements during single spikes and spike bursts in the same experiments as described in (D). Data represent the mean±s.e.m. ANOVA analysis with post hoc Dunnett's multiple comparison tests indicated significance.

FIGS. 3A-D illustrate differential regulation of Aβ40 and Aβ42 isoforms by temporal pattern of afferent input in rat hippocampal cultures. (A) [Aβ40]$_o$ and [Aβ42]$_o$ measured during different stimulation patterns (at constant mean rate of 1 Hz). [Aβ40]$_o$ was 47% higher during spike bursts (n=4, P<0.01) and 44% higher during "natural" discharges (n=4, P<0.01) comparing to single spikes. Conversely [Aβ42]$_o$ was not significantly altered by bursts (n=4, P>0.05). (B) Pattern dependency determined by burst/single ratio was higher for [Aβ40]$_o$ versus [Aβ42]$_o$ (n=4, P<0.01). (C) Pattern dependency for "natural" burst pattern was higher for [Aβ40]$_o$ versus [Aβ42]$_o$ (n=4, P<0.01). (D) Aβ40/42 ratio (expressed as percentage of Aβ40/42 during single spikes) was higher during regular spike bursts (n=4, *P<0.05) and "natural" bursts (n=4, **P<0.01) comparing to single spikes. Data represent the mean±s.e.m. ANOVA analysis with post hoc Bonferroni's multiple comparison tests (A,D); unpaired t-test (B,C).

FIGS. 4A-H illustrate basal neurotransmitter release bi-directionally regulates synaptic and Aβ40 dynamics by bursts. (A) Representative recordings of fEPSPs evoked by a single spike and a burst (each burst contains 5 APs; inter-spike-interval, 20 ms, inter-burst-interval, 30 s) in CA3-CA1 connections following 1 h stimulation under the following conditions: in control ACSF (Cnt), in the modified ACSF with increased Ca/Mg ratio (↑Ca/Mg, from 1.2/1.2 to 1.6/0.8 mM), in the presence of ω-CgTx (2 μM), A$_1$R agonist CCPA (2 nM), or GABA$_B$R agonist baclofen (1 μM). All the drugs were added to ↑Ca/Mg ACSF. Scale bars: 0.1 mV, 20 ms. (B) Average relative slopes of fEPSPs within the burst, normalized to the first peak. Increase in Ca/Mg reduced short-term synaptic facilitation during the burst (n=10) comparing to facilitation in control slices (n=8). ω-CgTx (n=11), CCPA (n=5) and baclofen (n=9) rescued short-term facilitation in ↑Ca/Mg-slices. (C) The magnitude of short-term plasticity determined as the burst/single ratio of fEPSP charge transfer per spike (Q$_{fEPSP}$) was reduced by ↑Ca/Mg, while rescued by ω-CgTx, CCPA and baclofen (the same experiments as in b). (D) ↑Ca/Mg increased [Aβ40]$_o$ during single spikes (n=6), while reduced [Aβ40]$_o$ during spike bursts. ω-CgTx, CCPA and baclofen rescued [Aβ40]$_o$ during single spikes (n=5-6) and spike bursts (n=5-6). (E) [Aβ42]$_o$ during either single- or burst stimulation pattern was uniformly increased by ↑Ca/Mg, while this increase was reversed by ω-CgTx, CCPA and baclofen (n=5-6). (F) ↑Ca/Mg reduced normal pattern dependency of Aβ40 (n=5). ω-CgTx, CCPA and baclofen rescued Aβ40 pattern dependency (n=5-6). (G) The Aβ40/42 ratio associated with single and burst patterns under different experimental conditions (n=5-6). (H) Increase in Ca/Mg reduced pattern dependency of the Aβ40/42 ratio (n=5) that was restored by ω-CgTx, CCPA and (n=5-6). Data represent the mean±s.e.m. ANOVA analysis with post hoc Bonferroni's multiple comparison tests indicate significance. *P<0.05, P<0.01, *P<0.001.

FIGS. 6A-H are graphs illustrating synaptic facilitation bi-directionally regulates Aβ40 dynamics by bursts. (A) Representative recordings of fEPSPs evoked by a burst (each burst contains 5 APs; inter-spike-interval, 20 ms, inter-burst-interval, 30 s) in CA3-CA1 connections following pre-incubation of slices for 3 h in a mini incubator (32° C., 95% O$_2$ and 5% CO$_2$) in control ACSF (Cnt), in the presence of GABA$_B$R antagonist CGP54626 (10 μM), ↑Ca/Mg ratio from 1 to 1.5 and after application of GABA$_B$R agonist baclofen (1 μM) in ↑Ca/Mg-slices. After pre-incubation, all the recordings have been made in normal ACSF. Scale bars: 0.1 mV, 20 ms. (B) Average relative slopes of fEPSPs within the burst, normalized to the first peak. CGP54626 (n=4) and ↑Ca/Mg (n=10) reduced short-term synaptic facilitation during the burst comparing to facilitation in control slices (n=8). Baclofen pretreatment rescued short-term facilitation in ↑Ca/Mg-slices (n=8-13, P<0.01). (C) The magnitude of short-term plasticity determined as the burst/single ratio of fEPSP charge transfer per spike (Q$_{fEPSP}$) was reduced by CGP54626 (n=4, P<0.01) and ↑Ca/Mg (n=7, **P<0.01) compared to control (n=6), while rescued by baclofen in ↑Ca/Mg-slices (n=7-8,

Figures 1E, 1F:
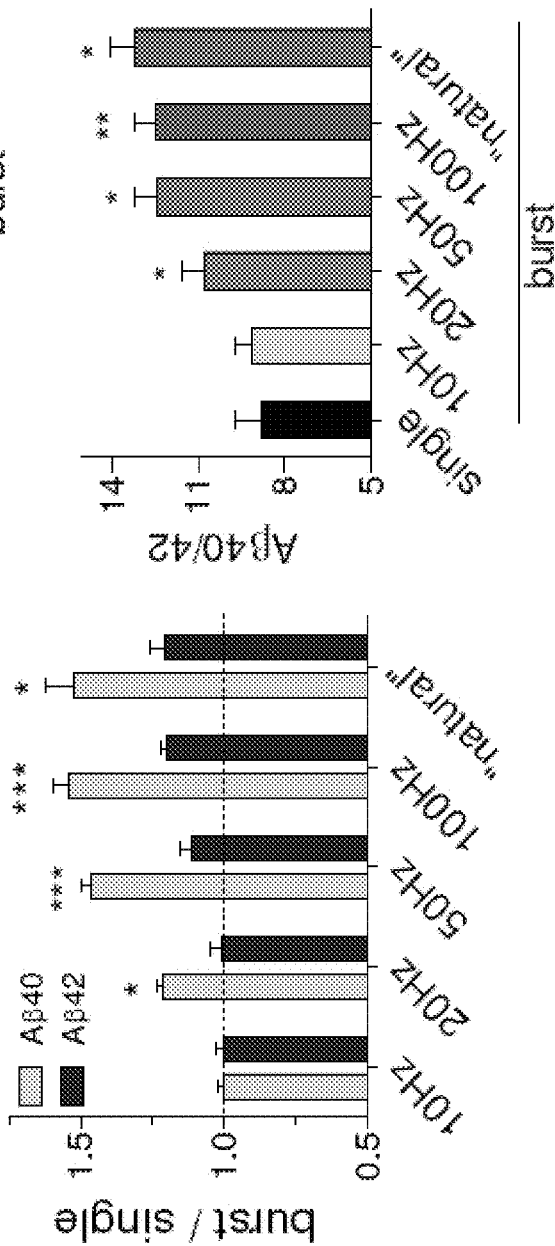

**P=0.0021). (D) CGP54626 and ↑Ca/Mg did not affect [Aβ40]$_o$ during single spikes (n=6, P>0.5), but reduced [Aβ40]$_o$ during spike bursts (n=6, *P<0.05). Baclofen increased [Aβ40]$_o$ during spike bursts (n=7, P<0.01), but not during single spikes (n=7, P>0.5). (E) CGP54626, ↑Ca/Mg and baclofen did not affect [Aβ42]$_o$ during ether single spikes or bursts (n=7, P>0.1). (F) CGP54626 and ↑Ca/Mg reduced normal pattern dependency of Aβ40 (*P<0.001) and abolished the isoform-specific difference on the burst/single ratio (n=7, P>0.3). Baclofen rescued pattern dependency of Aβ40 (n=9, *P<0.001). (G) CGP54626 and ↑Ca/Mg abolished normal difference between the Aβ40/42 ratio associated with single and burst patterns (n=7, P>0.6). Baclofen restored the difference between the Aβ40/42 ratio associated with single and burst patterns (n=9, P<0.01). (H) CGP54626 and ↑Ca/Mg reduced pattern dependency of the Aβ40/42 ratio (n=6-7, P<0.01), while baclofen restored its pattern dependency (n=9, *P<0.0001). Data represent the mean±s.e.m. ANOVA analysis with post hoc Bonferroni's multiple comparison tests indicate significance. Data is plotted as percentage of control stimulated by single spikes (D, E, G).

FIGS. 7A-H deficits in synaptic and Aβ40 dynamics in a familial AD mouse model can be reversed by increase in the GABA$_B$R-mediated presynaptic inhibition. (A) Representative recordings of fEPSPs evoked by single spikes and bursts (each burst contains 5 APs; inter-spike-interval, 20 ms, inter-burst-interval, 30 s) in CA3-CA1 connections in WT, APP/PS1 and baclofen-treated (1 μM, 3 h) APP/PS1 hippocampal slices. After pre-incubation, all the recordings were made in normal ACSF. Scale bars: 0.1 mV, 20 ms. (B) Average relative slopes of fEPSPs within the burst, normalized to the first peak. Baclofen reversed reduction in short-term synaptic facilitation by burst in APP/PS1 mice (n=6). (C) The magnitude of short-term plasticity determined as the burst/single ratio of fEPSP charge transfer per spike (Q$_{fEPSP}$) was lower in APP/PS1 than in WT slices (n=4-6) and reversed by baclofen in APP/PS1 slices (n=5). (D) Higher [Aβ40]$_o$ was measured during single spikes in APP/PS1 comparing to WT hippocampal slices (n=5-7), while [Aβ40]$_o$ did not differ between WT and APP/PS1 slices during spike bursts (n=5-7, P>0.4). Baclofen did not affect [Aβ40]$_o$ in APP/PS1 slices during single spikes (n=5, P>0.5), while increased it during bursts. (E) [Aβ42]$_o$ was higher in APP/PS1 comparing to WT slices either during single spikes (255±20%, n=5-7) or spike bursts (277±24%, n=5-7). Baclofen did not affect [Aβ42]$_o$ during either single spikes or bursts (n=5, P>0.5). (F) Baclofen rescued reduction in the Aβ40 burst/single ratio in APP/PS1 slices, while did not affect burst/single ratio of Aβ42 (n=7). (G) Baclofen increased Aβ40/42 ratio associated with burst patterns in APP/PS1 slices (n=6). (H) Baclofen rescued pattern dependency of the Aβ40/42 ratio in APP/PS1 slices (n=6-7). Data represent the mean±s.e.m. ANOVA analysis with post hoc Bonferroni's multiple comparison tests. *P<0.05, P<0.01, *P<0.001.

FIGS. 8A-J verify the Aβ40 and Aβ42 measurements by WAKO ELISA kit for human Aβ (A-E, n=3) and by Millipore ELISA kit for human Aβ (F-J, n=3).

FIGS. 9A-M illustrate dependency of [Aβ]$_o$ on spike-evoked Ca$^{2+}$ influx via voltage gated calcium channels (VGCCs). (A) Cd$^{2+}$ reduced [Aβ40]$_o$ during either spike pattern (n=4). (B) Cd$^{2+}$ did not affect [Aβ42]$_o$ during either spike pattern (n=4, p>0.1). (C) Cd$^{2+}$ reduced the Aβ40 burst/single ratio (**p<0.01), while did not affect burst/single ratio of Aβ42 (n=4, p>0.5). (D) Cd$^{2+}$ decreased Aβ40/42 ratio (n=4). (E) Cd$^{2+}$ abolished the Aβ40/42 pattern dependency (n=4). (F) Representative recordings of AMPAR-mediated EPSCs (holding potential −70 mV) evoked by single spikes and bursts in CA3-CA1 connections under control conditions and following addition of 50 μM EGTA-AM in acute hippocampal slices. Scale bars: 25 pA, 20 ms. (G) Average relative slopes of EPSCs within the burst, normalized to the first peak. EGTA-AM reduced short-term synaptic facilitation (n=11). (H) The magnitude of short-term plasticity determined as the burst/single ratio of EPSC charge transfer per spike (Q$_{EPSC}$) was lower following EGTA-AM application (n=11). (I) EGTA-AM reduced [Aβ40]$_o$ during spike bursts (n=4, *P<0.05). (J) EGTA-AM did not affect [Aβ42]$_o$ during either single spikes or bursts (n=4, P>0.3). (K) EGTA-AM reduced the Aβ40 burst/single ratio, while did not affect burst/single ratio of Aβ42 (n=4). (L) EGTA-AM decreased Aβ40/42 ratio associated with burst patterns (n=4). (M) EGTA-AM abolished the Aβ40/42 pattern dependency (n=4). Data represent the mean±s.e.m. ANOVA analysis with post hoc Bonferroni's multiple comparison tests (a-e, i-l) and unpaired t-tes (h,m). P<0.01, *P<0.0001.

FIGS. 10A-H illustrate that PS1 conformation does not depend on neuronal activity. (A) Schematic illustration of CFP-PS1-YFP fusion protein construct used for FRET detection: The CFP (donor) is fused to the N-terminus of PS1, whereas YFP (acceptor) is introduced into the TM6-7 loop region of PS1 between amino acids 351 and 352 according to Uemura et al. (Ref. 43). (B) Representative confocal images of hippocampal neuron that was transfected with CFP-PS1-YFP. White outline box in (B$_1$) corresponds to the blow-ups in (B$_2$) and (B$_3$). Arrowheads: the bouton that was bleached for calculation of FRET efficiency in C. (C) Pseudo-color coded fluorescent images of CFP-PS1-YFP before and after YFP photobleaching. Note increase of CFP fluorescence (ex: 442 nm; em: 460-500 nm) after YFP (ex: 514 nm; em: 530-560 nm) photobleaching. (D) L166P PS1 mutation increased CFP-PS1-YFP FRET efficiency from 0.07±0.005 (Cnt, n=114) to 0.10±0.007 (n=63). TTX did not change FRET (n=73, P>0.8). The background FRET assessed by photobleaching at 514 nm in neurons expressing PS1 fused only to CFP was negligible (0.002±0.008, n=20). Data represent the mean±s.e.m. (E) F$_{YFP}$/F$_{CFP}$ (FR) was not affected by application of 1 μM TTX (n=36, P>0.4). (F) FR was not affected by increasing the mean frequency of stimulation from 1 to 5 Hz (n=20, P>0.9). (G) FR was not affected by changing the temporal stimulation pattern from single spikes to spike bursts (n=25, P>0.5). (H) FR was not affected by changing the temporal stimulation pattern from single spikes to spike bursts in the presence of 1 μM baclofen (n=18, P>0.5). Scale bars: 10 μm (B$_1$), 2 μm (B$_3$), 1 μm (C). ANOVA analysis with post hoc Bonferroni's multiple comparison tests (d) and paired t-tes (e,f,g). P<0.01, *P<0.0001.

FIGS. 11A-G illustrate that APP processing was not affected by input pattern and basal transmitter release in hippocampal slices of non-transgenic rat (A-D) and APP/PS1 mice (E-G). 3600 stimuli were delivered for 1 h by single spikes or spike burst as described in FIG. 1C. The homogenates of hippocampal slices were assessed for the levels of full length APP (FL-APP), soluble APP (sAPP), APP C-terminal fragments (CTF) and for actin as a house keeping gene. (a) Representative western blots of FL-APP, sAPP, αCTF and actin in control (Cnt) and after pre-treatment in ACSF with ↑Ca/Mg in rat hippocampal. There were no significant differences between the burst/single ratio of FL-APP (B), sAPP(C) and αCTF (D) between the groups (n=4 per each group, P>0.5, un-paired t-test). (E) Representative western blots of FL-APP, βCTF and actin in APP/PS1 slices before and after pre-treatment with baclofen. There were no significant differences between the burst/single ratio of FL-APP (F)

and βCTF (G) between the groups (n=4 per each group, P>0.15, un-paired t-test). Each band was normalized to the amount of actin per lane. Data represent mean±s.e.m.

FIGS. 12A-D illustrate that Aβ clearance is not altered by neuronal activity. (A) Aβ40 half-life was assessed in cultures pretreated with TeTx (33 nM, 37° C., overnight). After blocking Aβ release by TeTx pretreatment, a fresh medium from untreated cells containing γ-secretase inhibitor was added (L-685,458, 2 μM) before the beginning of the measurements under the following conditions: (i) no stimulation; (ii) stimulation by single spikes, (iii) stimulation by spike bursts. Aβ40 was sampled each 30 min for 3 h. (B) The elimination of Aβ40 followed first-order kinetics. The half-life of Aβ40 was 70.5±8, 67.1±9 and 73.3±9 for non-stimulated cultures, stimulated by single spikes and spike bursts, respectively (n=3-5, P>0.5). (C) Aβ42 half-life was assessed in the same experiments similarly to Aβ40 as described in (A). (D) The elimination of Aβ42 followed first-order kinetics. The half-life of Aβ42 did not differ between non-stimulated cultures and cultures stimulated by single or burst patterns: 85.3±11, 79.3±9 and 80.4±10 (n=3-5, P>0.7).

FIGS. 13A-J illustrate that dark rearing enhances synaptic and Aβ40 facilitation by bursts in hippocampus. (A) Average relative slopes of fEPSPs within the burst, normalized to the first peak in visual cortex slices of normally-reared (NR) and dark-reared (DR) rats. Dark rearing did not affect short-term synaptic depression during the burst (n=6, P>0.05). Insert: Representative recordings of fEPSPs evoked by a burst layer 4→2/3 in visual cortex from NR and DR rats. (B) Dark rearing did not affect the magnitude of short-term depression determined as the $Q_{fEPSP}$ burst/single ratio (n=6, P>0.7). (C) Dark rearing did not affect $[A\beta40]_o$ and $[A\beta42]_o$ at either single or burst patterns (n=6, P>0.5). (D) Dark rearing did not affect pattern dependency of both Aβ40 and Aβ42 in visual cortex (n=6, P>0.6). (E) Dark rearing did not change the Aβ40/42 pattern dependency in visual cortex (n=6, P>0.5). (F) Average relative slopes of fEPSPs within the burst, normalized to the first peak in hippocampal slices of NR and DR rats. Dark rearing increased short-term synaptic facilitation during the burst (n=8). Insert: Representative recordings of fEPSPs evoked by a burst in CA3-CA1 connections of hippocampal slices from NR and DR rats. (G) Dark rearing increased the magnitude of short-term facilitation determined as the $Q_{fEPSP}$ burst/single ratio (n=8). (H) Dark rearing increased by 46% the difference between $[A\beta40]_o$ associated with single spikes vs. bursts, while did not affect $[A\beta42]_o$ (n=8). (I) Dark rearing enhanced burst/single ratio of Aβ40, while did not affect pattern dependency of Aβ42 in hippocampus (n=10). (j) Dark rearing increased Aβ40/42 augmentation by bursts in hippocampus (n=8). Data represent the mean±s.e.m. ANOVA analysis with post hoc Bonferroni's multiple comparison tests (A, C, D, F, H, I); unpaired t-tests (B, E, G, J). *P<0.05, P<0.01, *P<0.001.

Figure 14:
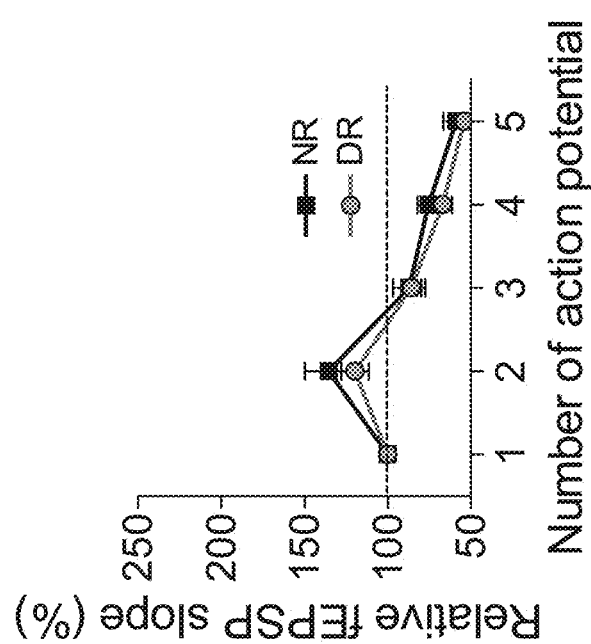

FIG. 14 is a graph illustrating that dark rearing does not alter synaptic facilitation by bursts in layer 6→2/3 of primary visual cortex. Average relative slopes of fEPSPs within the burst, normalized to the first peak in visual cortex slices of normally-reared (NR) and dark-reared (DR) rats. Dark rearing did not affect short-term synaptic depression during the burst (n=11, P>0.3).

FIGS. 15A-D illustrates that correlation between short-term plasticity in CA3-CA1 synaptic connections and dynamics of Aβ isoforms per individual animal across different experimental conditions. (A) Pooled data (n=73) show positive correlation between $Q_{fEPSP}$ and Aβ40 dynamics (slope of linear fit is 0.71±0.06, Spearman r=0.80, *P<0.0001). (B) No correlation was found between $Q_{fEPSP}$ and Aβ42 dynamics (Spearman r=0.22, n=73, P>0.05). (C) $Q_{fEPSP}$ facilitation positively correlates with Aβ40/42 dynamics (slope of linear fit is 0.41±0.04, Spearman r=0.81, n=73, *P<0.0001). (D) Illustration of experience-dependent regulation of the Aβ40/42 ratio and its implication in AD development. Experience-dependent reduction in release probability (Pr) results in enhanced synaptic and Aβ40 facilitation, boosting Aβ40/42. In contrast, experience-dependent increase in release probability causes a decrease in synaptic and Aβ40 facilitation during bursts, leading to Aβ40/42 decline. Given an inverse relationship between Aβ40/42 and the kinetics of amyloid formation[9,10] and synaptic impairments[10], a positive relationship between release probability and Aβ aggregation and toxicity is proposed.

Figure 16A:
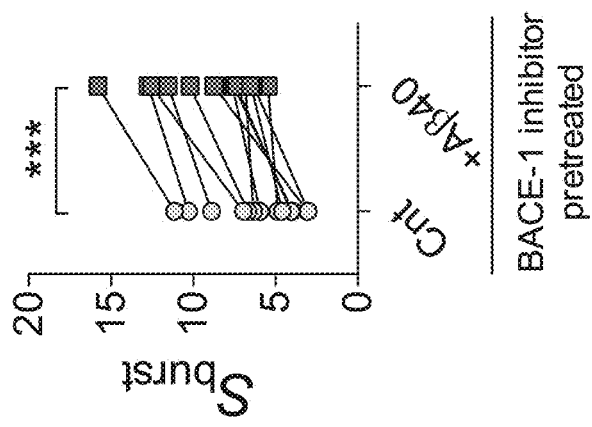
Figure 16B:
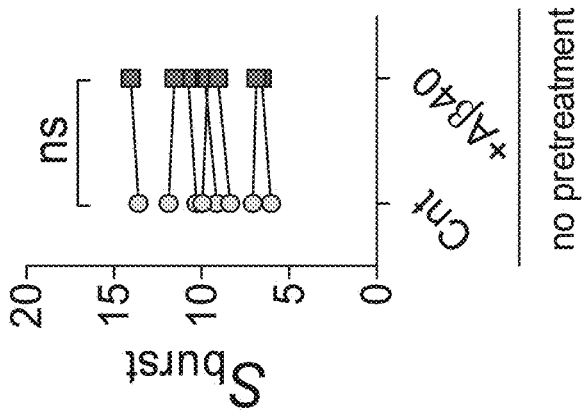

FIGS. 16A-B are graphs illustrating the effect of 100 pM Aβ40 on presynaptic strength during burst stimulation estimated by FM1-43 dye in control (A, n=8, P>0.2) and in BACE1 inhibitor-pretreated hippocampal cultures (B, n=13, ***P<0.0001).

FIGS. 17A-G are graphs illustrating regulation of Aβ40 and Aβ42 isoforms by temporal pattern of stimulation in human hippocampal slices. The data is produced from hippocampal slices of a patient with tumor in amygdala. Each stimulation pattern was repeated 3 times per group for ELISA measurements. (A) Representative recordings of fEPSPs evoked by a burst spike (each burst contains 5 APs; inter-spike-interval, 10 ms, inter-burst-interval, 30 s) in CA3-CA1 connections in ACSF (control) and in the presence of RS-baclofen (20 μM). Traces were normalized to the first control peak Scale bars: 50 ms. (B) Average relative slopes of fEPSPs within the burst, normalized to the first peak. Addition of baclofen increased short-term synaptic facilitation during the burst compared to facilitation in control slice. (C) Baclofen inhibited $[A\beta40]_o$ stronger during single spikes. (D) Baclofen uniformly inhibited $[A\beta42]_o$ during either single- or burst stimulation pattern. (E) Baclofen increased the Aβ40/42 ratio during burst pattern of stimulation. (F) Baclofen increased the burst pattern sensitivity of Aβ40 without affecting Aβ42 pattern dependency. (G) Baclofen induced pattern dependency of the Aβ40/42. Data represent the mean±s.e.m. *P<0.05, P<0.01, *P<0.001.

FIGS. 18A-G are graphs illustrating the egulation of Aβ40 and Aβ42 isoforms by temporal pattern of afferent input in human cortical slices. The data was obtained from cortex of two patients. Each stimulation pattern was repeated 3 times per Cnt and Bac-treated group for ELISA measurements. (A) Representative recordings of fEPSPs evoked by a single spike and a burst (each burst contains 5 APs; inter-spike-interval, 20 ms, inter-burst-interval, 30 s) following lh stimulation in ACSF (control) and in the presence of RS-baclofen (20 μM) Scale bars: 50 μV, 20 ms. (B) Average relative slopes of fEPSPs within the burst, normalized to the first peak. Addition of baclofen reduced short-term synaptic depression. (C) Effect of baclofen on $[A\beta40]_o$. (D) Effect of baclofen on $[A\beta42]_o$. (E) Effect of baclofen on the Aβ40/42 ratio during single spikes and spike bursts. (F) Baclofen increased the burst pattern sensitivity of Aβ40 with no effect on Aβ42 pattern dependency. (G) Addition of baclofen induced pattern dependency of the Aβ40/42. Data represent the mean±s.e.m. *P<0.05, P<0.01, *P<0.001.

DESCRIPTION OF SPECIFIC EMBODIMENTS
OF THE INVENTION

The present invention, in some embodiments thereof, relates to regulation of Amyloid-β (Aβ) molecular composition for the treatment of Alzheimer's disease (AD).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Accumulation and aggregation of the Aβ peptide in the extracellular space of distinct brain regions is a pathological hallmark of Alzheimer's disease. For several decades, scientists have searched for the mechanisms regulating cerebral Aβ oligomerization and subsequent aggregation. While numerous FAD-linked mutations leading to reduction in the Aβ40/42 ratio through over-production of the more pathogenic Aβ42 isoform have been discovered, how experience regulates Aβ40/42 dynamics remains largely unresolved.

The present inventors have examined regulation of Aβ40 and Aβ42 peptides by spiking patterns, release properties of synapses and sensory deprivation. They found that the extracellular concentration of Aβ40, but not that of Aβ42, is strongly regulated by synaptic release dynamics reflecting activity patterns, while no evidence was found for differential effect of activity patterns on either the production or the elimination steps. Hence, in contrast to the many FAD mutations, the present work highlights Aβ40 isoform as the key determinant of experience-dependent Aβ40/42 dynamics in hippocampal circuits.

The present data reveals a critical role for the temporal pattern of afferent input in Aβ40/42 regulation. Increase in the mean rate or number of single spikes at low frequencies uniformly augment the extracellular Aβ40 and Aβ42 levels. Conversely, keeping the mean rate constant with concomitant change in the temporal spiking pattern via a shift from single spikes to spike bursts preferentially increases $[A\beta 40]_o$. Bursts at constant frequencies≥20 Hz and 'natural' burst patterns boost Aβ40 without significant changes in the Aβ42 level. Thus, spike bursts, playing a central role in synaptic plasticity and memory encoding, represent a basic feature determining Aβ40/42 ratio in hippocampal circuits.

Thus, according to one aspect of the present invention there is provided a method of selecting a stimulator useful for the treatment of Alzheimer's disease (AD), the method comprising:

(a) contacting brain cells with the stimulator; and (b) determining an amount of Aβ40 in the brain cells, wherein an increase in an amount of Aβ40 following the contacting is indicative of a stimulator useful for the treatment of AD.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia.

According to one embodiment, the Alzheimer's is sporadic (i.e. not a familial form of the disease).

Exemplary stimulators contemplated by the present invention include for example electrical, chemical (e.g. pharmacological) magnetic, thermal, ultrasonic stimulators or combinations thereof.

Contacting cells with electrical stimulators may be performed by using a stimulation electrode. The stimulating may be effected in a recording chamber with field stimulation.

Different electrical stimulation patterns may be analyzed using this assay. Typically the stimulation pattern comprises bursts of electrical current.

Contacting cells with pharmacological stimulators can be performed by any in vitro conditions including for example, adding the pharmacological stimulator to cells derived from a subject (e.g., a primary cell culture, a cell line) or to a biological sample comprising same (e.g., a fluid, liquid which comprises the cells) such that the pharmacological stimulator is in direct contact with the cells. According to some embodiments of the invention, the cells of the subject are incubated with the pharmacological stimulator. The conditions used for incubating the cells are selected for a time period/concentration of cells/concentration of drug/ratio between cells and pharmacological stimulator and the like which enable the pharmacological stimulator to induce cellular changes, such as changes in the concentration of amyloid-β (Aβ) peptides. An exemplary incubation time is about 3-4 hours, e.g. 3 hours.

According to one embodiment, the contacting is effected in vitro.

According to another embodiment, the contacting is effected ex vivo.

The cells being analyzed are typically derived from a mammal, such as a rat, mouse, human etc.

The cells being analyzed may be dispersed (e.g. in a cell culture) or may form part of a tissue (e.g. a brain slice).

An exemplary cell culture contemplated by the present invention includes a primary culture of CA3-CA1 hippocampal neurons.

Exemplary brain slices contemplated by the present invention includes coronal slices (e.g. 300-500 μm) of hippocampus and primary V1 visual cortex.

According to one embodiment, the slices are pre-incubated in a pre-incubation medium prior to stimulation. The pre-incubation medium may comprise NaCl, (e.g. 125 mM); KCl, (e.g. 2.5 mM); $CaCl_2$, (e.g. 1.2 mM); $MgCl_2$, (e.g. 1.2 mM; $NaHCO_3$, (e.g. 25 mM); $NaH_2PO_4$, e.g. 1.25 mM; and glucose, (e.g. 25 mM).

As mentioned, the method of the present invention is effected by determining the amount of Aβ40 (and optionally Aβ42) in the extracellular medium of brain cells following the stimulation.

The term "amyloid" as used herein, refers to various types of protein aggregations that share specific traits when examined microscopically. Amyloid is typically identified by a change in the fluorescence intensity of planar aromatic dyes such as Thioflavin T or Congo Red. This is generally attributed to the environmental change as these dyes intercolate between beta-strands. The amyloid fold is characterized by a cross-beta sheet quaternary structure, that is, a monomeric unit contributes a beta strand to a beta sheet which spans across more than one molecule. While amyloid is usually identified using fluorescent dyes, stain polarimetry, circular dichroism, or FTIR (all indirect measurements), the "gold-standard" test to see if a structure is amyloid is by placing a sample in an X-ray diffraction beam; there are two characteristic scattering bands produced at 4 and 10 angstroms each, corresponding to the interstrand distances in the beta sheet structure. The amyloid protein disclosed in the present application refers to amyloid beta, as described below.

The phrase "amyloid beta", "Abeta", "beta-amyloid" or "amyloid beta peptide" is a physiological soluble product normally released from the amyloid beta protein precursor (βAPP or APP) through β and γ secretase cleavage and consists of two 40 and 42 amino acid peptides, usually abbreviated as Aβ40 and Aβ42, respectively (Selkoe, D. (2002), J. Clin. Invest. 110:1375-1381. The 42 amino acid amyloid beta peptide (Aβ42) is more hydrophobic & "sticky" (and hence aggregates more readily) than the 40 amino acid amyloid beta peptide (Aβ40), and has an increased tendency to form insoluble fibrils (Thioflavin S, Thioflavin T or congo red histologically positive) and increased neurotoxicity.

The nucleic acid and amino acid sequences for amyloid beta precursor protein and Aβ40 and Aβ42 are found in SEQ ID NOS: 1, 2, 3, 4 and 5. SEQ ID NO: 1 is the nucleic acid sequence encoding human amyloid beta precursor protein; SEQ ID NO: 2 is the nucleic acid encoding human Aβ40 peptide; SEQ ID NO: 3 is the amino acid sequence of human Aβ40 peptide; SEQ ID NO: 4 is the nucleic acid encoding human Aβ42, SEQ ID NO: 5 is the amino acid sequence of human Aβ42 peptide.

Methods of determining an amount of Aβ40 are known in the art. Such methods include the use of agents (e.g. antibodies) which are capable of specifically recognizing Aβ40 and not Aβ42. Such antibodies are commercially available from such companies as Wako, Abcam, Acris antibodies, Covance Research Products, Pierce and Sigma-Aldrich.

Exemplary methods for determining the concentration of Aβ40 in extracellular medium are listed herein below:

Enzyme Linked Immunosorbent Assay (ELISA): For Aβ40 (and Aβ42) detection a sandwich ELISA method is used. In this method the sample containing the Aβ40 or Aβ42 are loaded to a high binding microtiter plate which is coated with an Aβ antibody. The Aβ in the loaded sample binds to the Aβ coated plate. The complex of Aβ antibody and Aβ peptide from the loaded sample is recognized by a specific Aβ40 or Aβ42 antibodies labeled with horseradish peroxidase. After addition of TMB solution, and stopping the reaction with $H_2SO_4$ stop solution the absorbance is measured at 450 nm. If well calibrated and within the linear range of response, the amount of substrate present in the sample is proportional to the amount of color produced. A substrate standard is generally employed to improve quantitative accuracy. Elisa kits are commercially available for the detection of Aβ40—e.g. Wako c.n.

Western Blot: This method involves separation of a substrate from other protein by means of an acrylamide gel followed by transfer of the substrate to a membrane (e.g., nitrocellulose or PVDF). Presence of the substrate is then detected by antibodies specific to the substrate, which are in turn detected by antibody binding reagents. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance of the specific protein in the acrylamide gel during electrophoresis.

Radio-Immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence Activated Cell Sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical Analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In Situ Activity Assay: According to this method, a chromogenic substrate is applied on the cells containing an active enzyme and the enzyme catalyzes a reaction in which the substrate is decomposed to produce a chromogenic product visible by a light or a fluorescent microscope.

In Vitro Activity Assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

As mentioned, an increase in an amount of Aβ40 following stimulation is indicative of a stimulator useful for the treatment of AD.

Typically, the amount of Aβ40 is increased by more than about 10%.

According to another embodiment, the amount of Aβ40 is increased by more than about 20%.

According to another embodiment, the amount of Aβ40 is increased by more than about 30%.

According to another embodiment, the amount of Aβ40 is increased by more than about 40%.

According to another embodiment, the amount of Aβ40 is increased by more than about 50%.

As mentioned, the accuracy of the above described method may be further enhanced by determining an amount of Aβ42 in the brain cells, wherein an increase in Aβ40: Aβ42 is indicative of stimulator useful for the treatment of AD.

Methods of determining amounts of Aβ42 in brain cells are similar to those listed herein above with respect to Aβ40, except that antibodies that specifically recognize Aβ42 are used. Such antibodies are commercially available.

Typically when the Aβ40: Aβ42 ratio increases by at least 10%, this is indicative of an agent being useful for the treatment of AD.

According to another embodiment, the Aβ40: Aβ42 ratio increases by more than about 20% when the agent is useful for treating AD.

According to another embodiment, the Aβ40: Aβ42 ratio increases by more than about 30% when the agent is useful for treating AD.

According to another embodiment, the Aβ40: Aβ42 ratio increases by more than about 40% when the agent is useful for treating AD.

According to another embodiment, the Aβ40: Aβ42 ratio increases by more than about 50% when the agent is useful for treating AD.

Using the above described assay, the present inventors found particular electrical stimulation patterns that increased the Aβ40: Aβ42 ratio and as such were deemed useful for treating AD.

Thus, according to another aspect of the present invention, there is provided a method of treating Alzheimer's disease (AD) in a subject in need thereof, the method comprising electrically stimulating a nerve pathway in a brain region of the subject with at least two high frequency spike bursts of electrical currents, the bursts comprising between 2-20 spikes, wherein a frequency of the spikes in the bursts is between 5-200 msec.

As used herein, the phrase "electrically stimulating" refers to stimulation that modulates electric signals in neuronal tissue of brain regions.

As used herein, the term "brain region" refers to any tissue comprising that part of the central nervous system contained within the cranium.

Contemplated brain regions include, but are not limited to the hippocampus and the hypothalamus.

The connections of conscious memory derive from the association areas and reach the hippocampus via the parahippocampal, perirhinal and entorhinal cortex. From the entorhinal cortex the medial and lateral perforant pathway lead to the hippocampus. The efferent pathway from the hippocampus is mainly via the fornix to the hypothalamus. This last pathway is responsible for conscious (explicit) memory. The auditory cortex connects to the entorhinal area, the origin of the perforant pathways and the entry into the hippocampus.

Within the hippocampus (a structure on the temporal lobe of the neocortex), pertinent cellular areas involved with a specific pathway include the dentate gyrus, the CA1 field, the CA3 fields. Various examples include, but are not limited to, the upstream and downstream connections to the hippocampus (e.g., the hypothalamus, frontal cortex, entorhinal cortex, cingulate cortex, mammillary bodies, septum, bed nucleus of stria terminalis, amygdala, and nucleus accumbens).

According to a specific embodiment, the stimulating is directed at layers 2/3 of the Entorhinal Cortex—the area that stimulates the hippocampus via the lateral and medial Perforant Pathway.

As used herein, the term "burst" refers to a period in a spike train that has a much higher discharge rate than surrounding periods in the spike train. Thus, burst can refer to a plurality of groups of spike pulses. A burst is a train of action potentials that occurs during a 'plateau' or 'active phase', followed by a period of relative quiescence called the 'silent phase' (Nunemaker, Cellscience Reviews Vol 2 No. 1, 2005.) Thus, an exemplary burst may constitute 5 stimuli at 20-200 Hz, with 5 sec inter-burst-interval.

According to this embodiment, each burst comprises between 2-20 spikes.

Those of skill in the art realize that the spike rate within the burst does not necessarily occur at a fixed rate; this rate can be variable.

As used herein, the term "spike" refers to an action potential.

The duration of a treatment may vary from about 15 minutes to 2 hours.

It will be appreciated that the number of spike bursts per treatment may range from about 200-2000.

Preferably, each spike of the treatment will cause depolarization by 50-100 mV.

According to one embodiment, the spikes inside a burst are delivered in a repeating pattern.

According to another embodiment, the spikes inside the burst are delivered in an irregular, non-repeating pattern.

Exemplary irregular, non-repeating patterns contemplated by the present invention are those that are found in the brain of a healthy subject, e.g. in the hippocampus of a healthy subject.

Examples of "natural" burst patterns (inter-stimulus-intervals within the burst, ms) are provided in Table 1 herein below:

TABLE 1

| Burst Pattern |
|---|
| 120.4, 3.5, 4.1, 95.2, 10.9, 134.7, 19.4, 57.3, 15.3 |
| 223.8, 5.7, 198.2, 9.6, 3.7, 96.7, 3.5, 35.3, 64.8, 12.5, 160.2 |
| 22.6, 119.6, 7.7, 12.1, 76.6, 19.1, 11.9, 171.6, 43.3, 206.1 |
| 6.2, 242.7, 3.6, 7.3, 10.8, 96.3, 109.1, 202.1 |
| 4.1, 217, 10, 5, 6.8, 224.8, 309.8, 215.5 |
| 3.8, 4.5, 236.6 |
| 5.8, 3.4, 100.1, 4.9, 125.3, 4.6, 40.4, 170.4 |
| 11.1, 104.2, 13.6, 4, 91.6, 7, 11.8, 208.1 |
| 106.1, 107.7, 7.3, 10.7, 88.7, 18.7 |
| 120.9, 100.9, 7.2, 6.8, 103.1, 3.4, 13.5, 139.3, 7.1, 6.7, 38.8, 5.8 |
| 3.2, 98.3, 5.6, 115.6, 15.3, 101.2, 84.1, 23.3 |
| 4.6, 7.7, 222.6, 199.6, 5.4, 6.9, 102 |
| 207.1, 4.5, 4.7, 89.3, 4.3, 18.9, 180, 13.9, 189.3 |
| 113.4, 99.9, 11.6, 517.1 |
| 107.4, 115.3, 11.2, 91.3, 19.9, 34.4, 36.3, 90.7, 16.7, 79.1, 4.5, 8.2, 5.1, 95.3, 4.3 |
| 44.2, 108.1, 06.7, 7.3, 23.1, 88.4, 3.8 |
| 7.4, 20.5, 28, 11.6, 6.3, 11.3, 6.5, 32.4, 92.7, 87.8, 38.4, 18.3, 11, 27.3, 89.6, 4.8, 116.3, 4 |
| 5.2, 6.6, 105.5, 203.7, 11.2, 85.6, 106.3, 6.2, 5.5, 15 |
| 12.1, 115.2, 114.4, 6.7, 105.2, 3.6, 9.5, 4.4, 96.9, 81.9, 13, 7.5, 7.2, 5.6, 54.7, 9.3, 28.3, 88.8, 25.9, 67.3, 9, 48, 125.1, 88.7, 237.6, 26.2, 9.9, 128.3 |
| 10.3, 49.3, 5.2, 6.3, 49.4, 19, 11.3, 47.4, 41.3, 6.6, 25.2, 4.3, 128.8 |
| 3.6, 239.6, 95, 3.3, 8.7, 163.9, 12.7, 85.8, 30.2 |
| 113.9, 147.5, 43.9, 4.4, 14.5, 7.4 |
| 85.5, 5.1, 7.1, 8.8, 83.5, 20.2, 14.6, 46.2, 50.2, 182.4, 5 |
| 4, 5.8, 100.5, 7.4, 5.7, 95.5, 95.1, 7.9, 6.3, 10, 59.3 |
| 8.2, 106.5, 114.2, 34.1, 69.1, 163, 6.3, 7, 26.1, 6, 13.3, 306.3, |
| 9.5, 38.8, 9.5, 8.4, 31.6, 10.7, 72.4, 22.5 |
| 12.4, 3.2, 184.1, 5.6, 113.2, 79.9, 5.1, 109.6 |
| 4.3, 10.2, 97.3, 7.8, 185.3, 9.3, 51.5, 92.1, 4.8, 10.1, 5, 84.4, 3.2, 102, 97, 10.3 |
| 7.5, 97.4, 4.1, 7.5, 100.8, 4.7, 8, 88.3, 4.7, 6.5, 7.1 |
| 9.2, 6.7, 11.9, 186, 8.2, 8, 4.7, 107.7, 105.2, 4.5, 76.2 |

TABLE 1-continued

Burst Pattern 11.9, 5, 83.7, 73.3, 4.5, 27.9, 13.8, 14.1, 56.5, 117.9, 37.3, 84.8
216.6, 4, 4.7, 107.3, 3.6, 105.2, 93.4, 20.7, 7.1, 4.1
320.8, 3.8, 97.3, 5.8, 7.8, 95, 3.4, 7.6, 12.2, 160.4
5.9, 3.6, 3.1, 203, 98.2, 32.6, 45.1, 55.2
605.6, 7.3, 55.4, 105.1, 6.8, 5.9, 12.5, 19.8, 3.2
4.5, 11.5, 8.4, 6.2, 107.3, 3, 3.3, 68.2, 8.6, 28.6, 15.7, 9.5, 13.2, 27.2
86.7, 3.6, 44.1, 29.5, 5.9, 32.9, 14.2, 6.1, 9.4, 109.2, 3.6
3.5, 6.9, 46.6, 65.8, 3.8, 9.6, 110.7, 3.4, 5.2, 34.3, 56.3, 4.6, 4.6, 21
69.9, 3.7, 6.3, 96.6, 6.1
15.7, 208.3, 71.6, 9.7, 5.3, 6.4, 4.3, 4
81.3, 4.2, 12.8, 4.3, 6.4, 130.2, 18.2, 6.6, 5.8, 5.1, 29.9, 9.1, 7.9
7.1, 72.1, 12.2, 7.3, 3.4, 4.4, 7.7, 71.8, 84.2, 6.5, 26.2, 24.1
5.5, 49.7, 6.3, 6.4, 9.9, 8.9, 10, 22.8, 4.5, 39.2, 39.3
95.3, 89.1, 6.6, 39.1, 51.9, 7, 5.4, 15.9
242.2, 5.1, 6.9, 11, 4.8, 184.6, 3.8, 5.2, 9.5
11.4, 7, 50.9, 78.3, 9.2, 9.1, 3.6, 90.2, 3.7, 7.7, 4.3, 6.2
7, 3.9, 204.1, 3.6, 7.7, 3.6, 3.9, 88.4, 94.7, 7.3, 11.9
6.4, 6.6, 3.9, 5.3, 53.5, 24, 61.8, 8.1, 3.5, 5, 94.6, 4.5, 19.6
17.8, 200.6, 10, 4.2, 19, 57.4, 21, 92.5, 5.4, 15.2, 6, 59.1, 13.8, 19.7, 91.4
228.9, 5.5, 218.8, 3.9, 3.8, 221.4, 4, 5.3, 544.2, 16.6
18.7, 12.8, 155.3, 7.7, 80.8, 115.6, 18.6, 56.3, 9.1
7.9, 79.3, 94.3, 10.1, 8.3, 7.6, 6.3, 9.4, 46.9, 6.8, 79.1, 15.4, 89.1
16.4, 61.5, 94.3, 3.7, 15.5, 16.9, 15.8, 149, 15.3
8.6, 3.4, 4.5, 6.1, 82.4, 47.8, 5.6, 8.7, 68.7, 3.4, 32.5, 4.3, 7.4
116.4, 87.1, 4.8, 3.3, 6.2, 10.7, 3.4, 61.4, 5.2, 11.3, 49, 12.3, 4.6, 3.9, 90.5, 3.6, 4.3, 6.5
194.6, 5.2, 7.5, 6.3, 15.8, 7.1, 32.6, 10.9, 4.8, 28.7, 71.9, 29.1, 109.1
213.6, 6.1, 8.9, 20.3, 52.5, 3.5, 4.7, 92.9, 11.4, 8.8, 78.2, 95.6, 17.5, 19.5
4.5, 4, 25.3, 5.2, 64.1, 89.7, 7.5, 10, 5.8, 11.8, 55.2, 6.7, 7.8, 98, 9.3
102.3, 14.9, 3.5, 3.5, 4.8, 62.6, 7.6, 4.4, 12.4, 5.2, 73.1, 4.9, 84.4
5.2, 12.8, 4.4, 57.4, 7.7, 8.3, 13.8, 20.3, 81.8, 10.1, 78.9, 8.1, 4.7, 3.9
6.9, 3.6, 10.6, 78.5, 92.2, 19.1, 5, 9.2, 13.9, 26.8, 7.1, 6, 4.2
9.5, 83.3, 2.9, 12.6, 97.6, 3.5, 6.2
2.9, 6.3, 19.6, 5.9, 61.9, 3.8, 13.1, 58.6, 31.5, 5.9, 39.2, 32.1, 8.2, 5
7.8, 3.6, 81.6, 118.2, 11.6, 20.2, 151.6, 9.4, 4.9, 8.1, 262.2
22.7, 4.3, 4.1, 4.2, 138.2, 5.5, 38.1, 71.6
90.9, 9.7, 12.8, 15.5, 170.8, 11.6, 17.9, 7.3, 8.1, 152, 18.4
23, 180.7, 5.3, 66.5, 6.2, 17.3, 19.2, 73.2, 4.3, 8, 52.1, 4.3
97.4, 12.5, 5, 3.9, 14.1, 3.1, 31.4, 28.1, 8, 15.7, 74.9, 6.3, 6.9, 6.2, 5.9, 31.4
44.1, 24.6, 4.5, 4.7
20.8, 7.4, 12.6, 41.8, 15.9, 22.6, 17.5
93.2, 5.6, 5.2, 9.6, 9.4, 90.1, 119.4
7.1, 15.6, 52.1, 151.4, 21.3, 23, 88.1, 7.8, 3.7, 12.6, 16.5, 35, 5.9, 3.8, 38.2
48.2, 14.4, 17, 4.9, 79.8, 5, 11.4, 15.5, 64.4, 5, 11.5, 8.7, 108.1
13, 99.3, 5, 7.5, 4.3, 8.9, 10, 46.7, 9.6, 74.6, 43.9, 62.3, 11.7
5.4, 95.7, 91.2, 5.3, 26.1, 5.1, 10.4, 24, 4.7
105.7, 5.3, 3.4, 11.1, 79.2, 10.5, 7.3, 91.4, 6.5, 14.5, 24.3, 31.1, 104, 10.1, 26.3
17, 6.7, 76, 15, 75.7, 14.6, 16.1, 8.3, 10.5, 138.5
1.1, 4.9, 89.6, 75.8, 14, 9.5, 5.9, 17.8, 5.8, 49.2, 5.7, 3.6, 79.1, 5.1, 7, 25.5, 12.8, 4.1, 75.7
13.4, 13, 6.1, 3.7, 64.8, 10.5, 27.1, 77.9, 26.2, 8.7, 5.1, 4.5, 86.1, 8.1, 107.5
85.9, 28.4, 12.6, 8.4, 215.6, 3.9
4, 4.3, 209.4, 5, 16.5, 4.6, 33.2, 20.8, 12.4, 9.2, 18.4, 61.5, 5.3, 20.8, 16.5, 61.6, 5.8
102, 170, 13.7, 83.9, 5.5, 84, 11.9, 3.8, 3.3, 94.6
15.5, 10.8, 5.6, 65.6, 4.2, 12.2, 76.2, 4.4, 10.4, 67, 7.8, 91.1, 4.7, 4.6, 10.8, 11.5, 16.8, 38.6, 21.7, 77.5, 10.7, 96.4, 3.8, 4.7, 4.1
16.3, 6.6, 172.9, 5.6, 9.4, 8, 13.6, 60.7, 103.1
8.4, 181.7, 4.1, 7, 3.9, 14.1, 4.6, 74.3, 81.6, 12.6, 3, 4.1, 5.8, 23.2, 4.2, 59.8, 76.8, 7.7, 16.1, 8, 4.1
8.8, 93.6, 110, 14.3, 6.5, 4.2, 134.8, 6.9, 41.4, 89.83.2, 8.8, 7.8, 3.7, 83.1, 98.9, 4.1, 80.9

According to one embodiment, the stimulating is effected non-invasively.

Preferably, the site which is targeted by the non-invasive stimulation is at the Entorhinal Cortex.

Thus, the present invention envisages the use of transcranial direct current stimulation (tDCS) to stimulate the brain. This method is described in Marshall et al. J Neuros; November 2004; Antal et al. IVOS February 2004; and Madhavan S et al; Exp Brain Res. 2011 March.

Another type of stimulation envisaged by the present inventors includes repetitive transorbital alternating current stimulation (rtACS) as described by:Fedorov A et al.; Restor Neurol Neurosci. 2010 Jan. 2; and oliadze et al; J. Physiol. 2010 Dec. 15.

Quick pulses of magnetic stimulation can be applied externally or transcranially, for example repetitive transcranially magnetic stimulation (rTMS).

This noninvasive method causes depolarization in the neurons of the brain. TMS uses electromagnetic induction to induce weak electric currents using a rapidly changing magnetic field. This method is more fully described in Brighina et al., J Headache Pain. 2011 Feb 25; Poulet E et al.; Psychiatr Danub. 2010 November; and Koch G et al.; Funct Neurol. 2010 July-September; 25(3): 159-63.

According to one embodiment, the stimulating is effected invasively (e.g. by deep brain stimulation (DBS).

Examples of electrodes that may be used for invasive stimulation include the single multi contact electrode with eight contacts separated by 2½ mm, and each contract would have a span of approximately 2 mm. Another example is an electrode with two 1 cm contacts with a 2 mm intervening gap. Yet further, another example of an electrode that can be used in the present invention is a 2 or 3 branched electrode/catheter to cover the predetermined site or target site. Each one of these three pronged catheters/electrodes have four contacts 1-2 mm contacts with a center to center separation of 2 of 2.5 mm and a span of 1.5 mm.

The present invention also contemplates administration of a pharmaceutical agent (or a combination of pharmaceutical agents) either independently or in combination with electrical stimulation.

When in combination, the pharmaceutical agent may be administered prior to electrical stimulation (e.g. 1 hour before; 6 hours before; or 24 hours before); concomitant with stimulation; or following stimulation (e.g. 1 hour after; 6 hours after; or 24 hours after).

Selection of a particular pharmaceutical agent (or combination thereof) may be effected using the assay system described herein above. Further, it will be appreciated that the assay system described herein above may also be used for selecting a particular dose of the pharmaceutical agent. According to this aspect of the invention, a pharmaceutical agent may be selected that increases the amount of Aβ40 in a sample of brain cells (or a slice of brain tissue). According to a preferred embodiment, the pharmaceutical agent is selected that increases the Aβ40/42 ratio in a sample of brain cells (or a slice of brain tissue).

The present inventors have found that decreasing ongoing basal neurotransmitter release specifically increases the Aβ40/42 ratio during periods of spike bursts relatively to single spikes. Thus, the present inventors propose that agents (and doses thereof) for the treatment of Alzheimer's should be selected which selectively inhibit basal neurotransmitter release and not burst-evoked transmitter release.

Typically, doses of pharmaceutical agents that lower synaptic transmission of low frequency pulses in the brain to a greater extent than high frequency bursts are low doses, in the range of dissociation constant (Kd) of the agent (up to concentration equal to 2×Kd).

Exemplary pharmaceutical agents contemplated by the present invention include $GABA_B$ receptor agonists, $A_1$ receptor agonist, metabotropic glutamate receptors group II agonists, $M_2$ muscarinic agonists, $CB_1$ endocannabinoid receptor agonists, Mu opioid receptor agonists, voltage-dependent antagonists of voltage-gated calcium channels and calcium chelators.

Examples of $GABA_B$ receptor agonist is selected from the group consisting of baclofen, CGP44532 and CGP35024.

Examples of $A_1$ receptor agonists include 2-Chloro-N-cyclopentyladenosine (CCPA), N-Cyclopentyladenosine (CPA), N-Bicyclo[2.2.1]hept-2-yl-5'-chloro-5'-deoxyadenosine (ENBA), N-[(1S,2S)-2-Hydroxycyclopentyl]adenosine and 2-Chloro-N-cyclopentyl-2'-methyladenosine.

Examples of metabotropic glutamate receptor group II agonists include (1R,4R,5S,6R)-4-Amino-2-oxabicyclo [3.1.0]hexane-4,6-dicarboxylic acid (LY379268),(1S,2S,5R, 6S)-2-Aminobicyclo[3.1.0]hexane-2,6-dicarboxylic acid (LY35474), (2R,4R)-4-Aminopyrrolidine-2,4-dicarboxylate and (2S,1'S,2'S)-2-(Carboxycyclopropyl)glycine (L-CCG-I).

Examples of $CB_1$ endocannabinoid receptor agonists include N-(2-Chloroethyl)-5Z,8Z,11Z,14Z-eicosatetraenamide (ACEA), N-(Cyclopropyl)-5Z,8Z,11Z,14Z-eicosatetraenamide (ACPA), rel-5-(1,1-Dimethylheptyl)-2-[(1R,3S)-3-hydroxycyclohexyl] phenol (CP47497) and N-(2-Hydroxyethyl)-7Z,10Z,13Z,16Z-docosatetraenamide.

Examples of antagonists of voltage-gated calcium channels include magnesium chloride, magnesium threonate and magnesium chelated with the amino acids glycine, cadmium and lysine. Toxins specific to voltage gated calcium channels (e.g. N-type calcium channels) such as ω-conotoxin GVIA, ω-Aga-IIIA, and ω-CTx-MVIIC are also contemplated.

Examples of calcium chelators include, but are not limited to BAPTA (1,2-bis(o-amino phenoxy)ethane-N,N,N',N'-tetraacetic acid), EGTA (glycol-bis(2-aminoethylether)-N,N, N',N'-tetraacetic acid), EDTA (2-[2-(bis(carboxymethyl) amino)ethyl-(carboxymethyl)amino]acetic acid), or CDTA (trans-1,2-cyclohexane diamine-tetraacetic acid) which are non-permeant agents, or the corresponding permeant forms, that is to say BAPTA-AM (1,2-bis-(o-Amino phenoxy) ethane-N,N,N',N'-tetraacetic tetra-(acetoxymethyl) acid Ester), derivatives of BAPTA-AM such as 5,5'-difluoro-BAPTA-AM (5,5' F2 BAPTA), or 5-5'-dimethyl-BAPTA-AM, EGTA-AM, EDTA-AM and CDTA-AM. Preferred calcium chelator is EGTA-AM.

Combinations of pharmaceutical agents are also contemplated by the present inventors include. Preferably each pharmaceutical agent in a particular combination works via a different mechanism (e.g. via different receptors) to avoid over stimulation of a particular pathway.

The pharmaceutical agent may be administered directly into the brain or provided it is able to cross the blood brain barrier it may be administered systemically.

Thus, suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion, infusion pumps); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions comprising the agents of the present invention for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, artificial CSF or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., Alzheimer's disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially using the assay system described herein above. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Clinical evaluation of a subject treated according to the methods of the present invention include subjective measures such as, for example, neurological examinations and neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

In addition to electrical stimulation and/or chemical stimulation, other forms of stimulation can be used, for example magnetic, or thermal or combinations thereof. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Thermal stimulation can be provided by using implanted probes that are regulated for heat and/or cold temperatures which can stimulate or inhibit neuronal activity, for example, U.S. Pat. No. 6,567,696, which is incorporated herein by reference in its entirety. Still further, stimulation may also be in the form of ultrasound. (Norton 2003).

It is expected that during the life of a patent maturing from this application many relevant $GABA_B$ receptor agonists, $A_1$ receptor agonisst, metabotropic glutamate receptors group II agonists, $M_2$ muscarinic agonists, $CB_1$ endocannabinoid receptor agonists, Mu opioid receptor agonists, voltage-dependent antagonists of voltage-gated calcium channels will be developed and the scope of those terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed.

(1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Slice preparation and treatment: All animal experiments were approved by the Tel Aviv University Committee on Animal Care. 1-2-month-old Wistar rats, 3-month-old APPswe/PS1dE9[31] and corresponding WT mice (B6C3F1/J background), APP[−/−][29] and corresponding WT mice (C57BL/6J background) were used. Coronal slices (400 μm) of hippocampus and primary visual cortex (V1) were prepared in a cold (4° C.) storage buffer containing (in mM): sucrose, 206; KCl, 2; $MgSO_4$, 2; $NaH_2PO_4$, 1.25; $NaHCO_3$, 26; $CaCl_2$, 1; $MgCl_2$, 1; glucose, 10. The slicing procedure was performed using a Leica VT1200 vibratome. Slices were transferred to a submerged recovery chamber at room temperature containing oxygenated (95% $O_2$ and 5% $CO_2$) artificial cerebrospinal fluid (ACSF) for 1 h before the experiment. The ACSF contained, in mM: NaCl, 125; KCl, 2.5; $CaCl_2$, 1.2; $MgCl_2$, 1.2; $NaHCO_3$, 25; $NaH_2PO_4$, 1.25; glucose, 25. In experiments with the modified ACSF (↑Ca/Mg, FIG. 4), extracellular magnesium concentration was reduced to 0.8 mM, while extracellular calcium concentration was increased to 1.6 mM preserving the total ion concentration. Following 1 h of recovery slices were transferred to a stimulating chamber inside a mini incubator (32° C., 95% $O_2$ and 5% $CO_2$) for 1 h electrical stimulation (4 slices per 500 ml ACSF). For experiments including pharmacological treatments (FIG. 4 and FIGS. 12F-M), the drug required for each experiment (1 mM baclofen, 2 nM CCPA, 2 mM w-conotoxin, or 50 mM EGTA-AM) was added to the ACSF in the stimulation chamber. For prolonged incubation experiments (FIGS. 6 and 7) slices were kept in ACSF containing the required drug for 3 h prior to stimulation in the mini incubator.

Hippocampal Cell Culture. Primary cultures of CA3-CA1 hippocampal neurons were prepared from newborn Wistar rats on postnatal days 0-2, as described[28]. For the Munc13-1/2 double knockout mice[33] (Munc13-DKO), hippocampal cultures were prepared from embryonic day 19 (E19). The experiments were performed in mature (15-28 days in vitro) high-density (synaptic density>1.5 synapses/mm$^2$ of dendritic surface area) cultures. The cultures were grown in a culture medium (Gibco, 51200-038) with modified $[Mg^{2+}]_o$ (1.2 mM instead of 0.8 mM)[70].

Electrical Stimulations of Slices and Cultures. All stimulations were done in the presence of NMDAR and AMPAR blockers (50 mM AP-5, 20 mM DNQX). Two distinct stimulation protocols were utilized (FIGS. 4-15), preserving the mean rate constant (3600 stimuli per 1 hour): (1) Single, low-frequency stimulation, 3600 stimuli at 1 Hz; (2) High-frequency spike bursts: 3600 stimuli consisting of 720 bursts; each burst contained 5 spikes with inter-spike-interval of 10 ms and inter-burst-interval of 5 sec. Cultures were stimulated in the same medium they were maintained in prior to stimulation excluding Aβ clearance experiments as described below. Following stimulation, ACSF was collected from stimulating chamber for extracellular Aβ measurements by ELISA. Slices from each experimental condition were transferred to a recording chamber for fEPSP/EPSC recordings and biochemical analysis. As fEPSPs were stable during the stimulation period of 1 hour in the ACSF solution containing 50 mM AP-5 (data not shown), electrophysiological recordings were performed after the stimulation. Stimulated slices were collected for APP and its metabolites detection by Western blot.

Dark Rearing: Wistar rats were randomly assigned to the Dark Rearing (DR) or to the control, Normal Rearing (NR) group. DR rats were kept in complete darkness for 4-5 weeks, from P8 to P35-P42. A parallel NR control group was placed in a normal light/dark cycle (12 h/12 h). P35-P42 coronal hippocampal and visual cortex slices from DR and NR rats were prepared.

Slice Electrophysiology: Extracellular fEPSP and intracellular EPSC recordings were performed at room temperature in a recording chamber on the stage of a Zeiss Axiovert S100 microscope. fEPSPs were recorded using a glass pipette containing ACSF (1-2 MΩ). Whole-cell patch pipettes (2-3 MΩ) were used to record EPSCs under −70 mV holding potential using the following intracellular solution (in mM): KGluconate, 120; KCl, 3; HEPES, 10; NaCl, 8; $CaCl_2$, 0.5; EGTA, 5; $Mg^{2+}$-ATP, 2; and GTP, 0.3; pH adjusted to 7.25 with NaOH. Serial resistance was not compensated. For AMPAR-mediated EPSCs recordings, AP-5 (50 mM) and gabazine (30 mM, Tocris) were added to the ACSF solution. fEPSPs recordings were done in the presence of AP-5 (50 mM). Stimuli in the Schaffer collateral-commissural pathway evoked fEPSPs or EPSCs responses which were recorded from the CA1 stratum radiatum. For intracortical recordings, the stimulating electrode was placed in layer 4 or in layer 6 right above the white matter, and the recording electrode was placed in layer 2/3 of the same column. Stimulations were delivered through a glass suction electrode (10-20 mm tip) filled with ACSF. fEPSPs were induced by repetitive stimulations at 0.033 Hz or by bursts (each burst contains 5 spikes, inter-spike-interval 20 ms, inter-burst-interval 30 s). The change in fEPSP slope between spikes in the burst was measured as percentage from the first fEPSP to estimate short-term plasticity. The integral of the burst-evoked fEPSP was divided by the number of spikes to calculate the charge transfer per spike ($Q_{fEPSP}$). Signals were recorded using a MultiClamp 700A/B amplifiers, digitized by DigiData1440A (Molecular Devices) at 10 kHz, and filtered at 2 kHz. fEPSPs and EPSCs were analyzed by pClamp10 software (Molecular Devices).

Aβ detection. Concentrations of rat Aβ40 and Aβ42 in ACSF were determined following stimulations by sandwich ELISA using highly sensitive kits, Wako, c.n. 294-62501 and 292-64501 for Aβ40 and Aβ42, respectively; BNT77 (Aβ11-28) was used as a capture antibody, BA27 as antibody for C-terminal of Aβ40, and BC05 for C-terminal of Aβ42. Quantification of human Aβ40 and Aβ42 concentrations (FIG. 7) were also determined using two additional sets of human Aβ sandwich ELISA kits: Wako, c.n. 292-62301; 298-62401 and Milipore EZBRAIN40; EZBRAIN42 (FIG. 8). All ELISA kits procedures were done according to the manufacturer's instructions. In cultures, the background levels of Aβ in the medium measured before stimulation were subtracted from the Aβ values after the stimulation. In acute slices, the background levels of Aβ were negligible (<3% of the signal) and were not subtracted from Aβ values measured after the stimulation.

PS1 FRET Imaging and Analysis: The CFP-PS1-YFP construct was generated on the basis of GFP-PS1-RFP. GFP was replaced by Cerulean (denoted as CFP) using Age1 and Xho1 and RFP was replaced by Citrine (denoted as YFP) using Not1. PS1-CFP only was constructed by cutting out YFP with Not1. FRET imaging was carried as described before[30,71] using FV1000 spectral confocal microscope (Olympus). CFP was excited at 442 nm and fluorescence emission was measured between 460-500 nm. YFP was imaged at 514 nm (excitation) and 525-560 nm (emission). Photobleaching of YFP was carried out with 514 nm laser line, at 2.3 mW of laser output. Images were 512×512 pixels, with a pixel width of 92-110 nm. Z-stacks were collected from 3-4 μm optical slice, at 0.6-0.8 μm steps. Donor dequenching due to the desensitized acceptor was measured from CFP emission before and after the acceptor photobleaching. FRET efficiency, E, was then calculated using the equation $E=1-I_{DA}/I_D$, where $I_{DA}$ is the peak of donor emission in the presence of the acceptor and $I_D$ is the peak after acceptor photobleaching. In order to exclude potential contribution of donor/acceptor ratio to FRET efficiency measurements, all FRET experiments have been performed under saturation conditions of acceptor over donor. Detection of CFP/YFP signals has been done using custom-written scripts in MATLAB as described earlier[30,71].

Aβ Elimination Half-Life. Half-life of Aβ40 and Aβ42 in the extracellular fluid was determined in hippocampal cultures following pretreatment with TeTx (33 nM, 37° C., overnight). After TeTx treatment, the medium was replaced with medium from untreated sister cultures including 2 μM L-685, 458, a cell-permeable g-secretase inhibitor was applied. Samples were collected every 30 min during 3 h after L-685, 458 application, and then assessed for Aβ40 and Aβ42 by ELISA.

Immunoblot Analysis. At the end of each stimulation, hippocampal slices were homogenized and prepared for the detection of full-length APP, soluble APP and APP-C terminal fragment (APP-CTF) by western blotting as described previously[18]. Full length APP and soluble APP was probed using anti-APP 22C11 monoclonal antibody (Millipore, Temecula, Calif., 1:2000). In APP/PS1 slices, APP-bCTF was detected using 82E1 monoclonal antibody (IBL, Japan, 1:200). Both 22C11 and 82E1 probing were followed by goat anti-mouse HRP conjugated secondary antibody (Jackson ImmunoResearch, West Grove, Pa., 1:5000). APP-aCTF was detected using rabbit anti-APP-CTF antibody (Millipore, Temecula, Calif., 1:10,000) followed by goat anti-rabbit HRP conjugated secondary antibody (Jackson ImmunoResearch, West Grove, Pa., 1:5000). Following detection, blots were stripped with Restore™ Western Blot Stripping Buffer (Pierce, Thermo Scientific, Rockford, Ill.) and then re-probed with mouse anti-actin (SIGMA, Israel, 1:10,000) and HRP-conjugated goat anti-mouse (1:5000) antibodies as a loading control protein. All proteins were visualized by SuperSignal® West Pico Chemiluminescent (Pierce; Thermo Scientific, Rockford, Ill.). Densitometry was performed using the ImageJ Analysis software, and each band was normalized to its actin signal.

Estimation of Short-Term Presynaptic Plasticity Based on FM Dye Staining. Synaptic vesicle release at single synapses in primary hippocampal cultures was determined using the activity-dependent FM1-43 dye as described previously[28]. Briefly, action potentials (APs) in neurons were initiated by field stimulation during dye loading, and the terminals, after undergoing vesicle exocytosis coupled to endocytosis, were stained by 10 mM FM1-43. During FM loading and unloading the extracellular solution contained (in mM): NaCl, 145; KCl, 3; glucose, 15; HEPES, 10; $MgCl_2$, 1.2; $CaCl_2$, 1.2; pH adjusted to 7.4 with NaOH. Kynurenic acid (0.5 mM) was added to prevent recurrent activity through blockage of excitatory postsynaptic responses during loading and unloading. After dye loading, external dye was washed away in $Ca^{2+}$-free solution containing ADVASEP-7 (0.1 mM; Sigma). To confirm that the fluorescent spots corresponded to release sites, we evoked at 5 Hz for 4 min during the unloading step to obtain release of dye-filled vesicles. The total amount of releasable fluorescence at each bouton (ΔF) was calculated from the difference between fluorescence after loading and after unloading ($\Delta F = F_{loading} - F_{unloading}$). The total presynaptic strength has been calculated as S=DF×D, whereas D is the density of FM-(+) puncta per image area. To determine the sign and magnitude of short-term plasticity, we calculated the Sburst/Ssingle ratio over the same image area, whereas Ssingle was measured for the loading of 30 APs@1 Hz and Sburst for 30 APs@6 bursts (each burst contained 5 APs, inter-spike interval=10 ms, inter-burst-interval=5 sec).

Chemical Reagents. DNQX, Baclofen, CGP54626, CCPA and Gabazine were purchased from Tocris; AP-5 and Tetanus toxin (TeTx) were purchased from Sigma; Tetrodotoxin (TTX) and w-conotoxin GIVA (w-CgTx) from Almone Labs, BACE1 inhibitor IV and L-685,458 from Calbiochem, EGTA-AM from Invitrogen, and FM1-43 from Biotium.

Statistical Analysis. Error bars shown in the figures represent standard error of the mean (s.e.m.). The number of animals is defined by n. One-way ANOVA analysis with post hoc Bonferroni's were used to compare several conditions (*P<0.05; P<0.01; *P<0.001). Unpaired two-tailed t-tests were used for two-group comparison. Nonparametric Spearman test has been used for correlation analysis.

Example 1

Temporal Spiking Pattern Differentially Regulates Aβ42 and Aβ40 Isoforms

To address the question, whether attributes of neuronal activity affect the molecular composition of Aβ, the regulation of Aβ42 and Aβ40 species by neuronal activity patterns in hippocampal slices was examined. First, the effect of the mean neuronal firing rate on the extracellular levels of Aβ42 and Aβ40 was examined. In each experiment, rat hippocampal slices were divided into three groups (FIG. 1A): (i) slices without stimulation for the measurement of spontaneously released Aβ, (ii) slices stimulated by single spikes at a constant rate of 1 Hz; (iii) slices stimulated by single spikes at a constant rate of 5 Hz. The duration of stimulation was 1 h in both groups (ii) and (iii). As presynaptic terminals have been suggested to be a key site for Aβ production and release, the effect of presynaptic axonal activation on Aβ release was isolated by blocking postsynaptic excitatory AMPA and NMDA receptors with specific antagonists (20 mM DNQX and 50 mM AP-5, respectively). Following stimulation, the concentrations of Aβ40 and Aβ42 in the ASCF ([Aβ40]$_o$ and [Aβ42]$_o$) were measured by sandwich ELISA. The concentrations of spontaneously released Aβ peptides in non-stimulated slices were less than 3% of those evoked by 1 Hz stimulation (FIG. 1B). A five-fold rise in the stimulation rate (or stimuli number) resulted in ~80% increase of both [Aβ40]$_o$ and [Aβ42]$_o$ (P<0.001, FIG. 1B). Thus, an increase in the firing rate at a constant frequency equally regulated [Aβ40]$_o$ and [Aβ42]$_o$. Furthermore, a variety of pharmacological manipulations perturbing spontaneous neuronal and synaptic activity in hippocampal cultures had similar effects on [Aβ40]$_o$ and [Aβ42]$_o$ (FIG. 2A), in agreement with previously reported data.

Next, the effect of varying the temporal pattern of stimulation on [Aβ40]$_o$ and [Aβ42]$_o$ was assessed. The effect of high-frequency spike bursts was explored on the ratio between [Aβ40]$_o$ and [Aβ42]$_o$ (Aβ40/42) by comparing three stimulation patterns (FIG. 1C): (i) single spikes delivered at a constant frequency of 1 Hz; (ii) 'spike bursts' constituting of 5 stimuli at regular frequency of 10, 20, 50 or 100 Hz with 5 sec inter-burst-interval, and (iii) a 'natural' pattern of high-frequency discharges reproduced from in vivo recordings in hippocampal CA1 region of behaving rats[28]. Note that the mean rate was preserved at 1 Hz for the 1 h duration of stimulation, corresponding to an equal stimuli number in all paradigms. It was found that [Aβ40]$_o$ measured following bursts periods gradually increased with the frequency of spikes within the bursts and at frequencies≥20 Hz was significantly higher than [Aβ40]$_o$ accumulated during periods of single stimuli (FIG. 1D). As a result, Aβ40 burst/single ratio increased to ~1.5 at 50-100 Hz regular and "natural" burst patterns (FIG. 1E). Surprisingly, [Aβ42]$_o$ was practically insensitive to the stimulation pattern (FIG. 1D-E). As a result of this isoform-specific susceptibility, Aβ40/42 was higher following periods of bursts compared with periods of single spikes (FIG. 1F). Increase in the inter-burst interval from 5 to 30 sec resulted in a comparable pattern dependency of Aβ40/42 (FIG. 2B,C). [Aβ40]$_o$ and [Aβ42]$_o$ were negligible in slices pretreated with inhibitors of b-secretase (BACE1 inhibitor IV, 5 mM) or g-secretase (L-685,458, 2 mM) and below detection limits in hippocampal slices from APP$^{-/-}$ mice[29] (FIG. 2D-E, n=3), confirming the specificity of ELISA. Similar results were obtained in primary hippocampal cultures displaying ~4-fold higher [Aβ40]$_o$ and [Aβ42]$_o$ levels compared with the levels measured in slices (FIG. 3), suggesting that the observed isoform-specific Aβ dynamics was independent of the absolute Aβ levels. Taken together, these results demonstrate that Aβ40/42 is dynamically regulated by spiking patterns due to selective 'burst-sensitivity' of the Aβ40 isoform.

Example 2

Bi-Directional Regulation of Aβ40/42 Dynamics by Transmitter Release

Figure 4A:
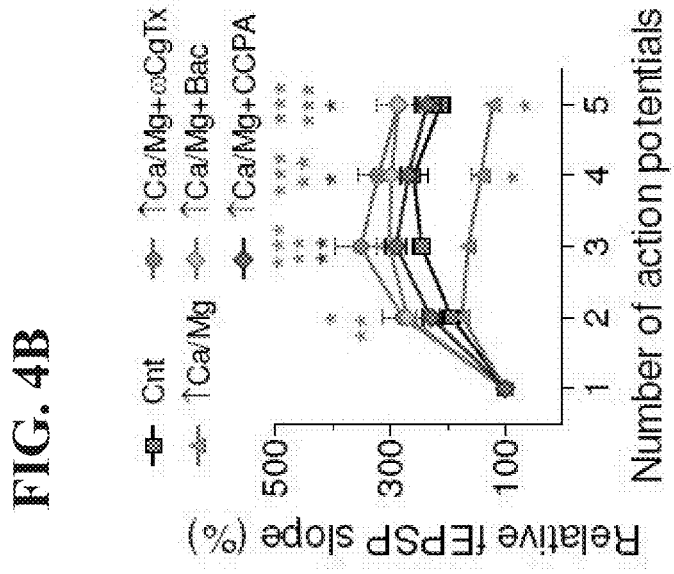
Figure 4B:
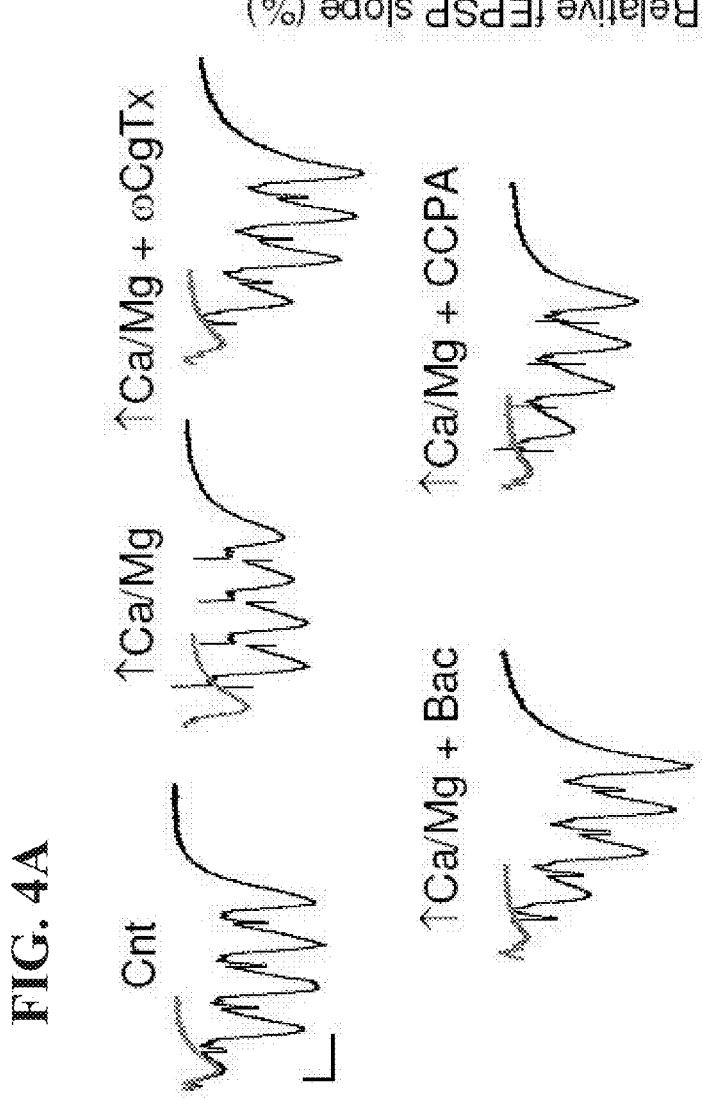
Figure 5A:
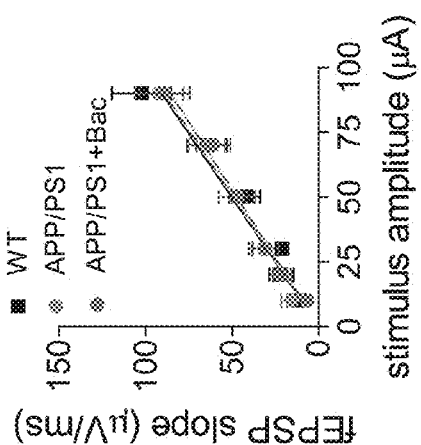
FIGS. 5A-C are graphs illustrating embodiments of the present invention. (A) Input-output relationship between stimulation amplitude (delivered at 0.1 Hz) and the slope of fEPSP in control slices (n=8, slope of linear fit is 0.78±0.04) and in slices following acute application of the following drugs before the stimulation: modified ACSF solution containing 1.6 mM Ca$^{2+}$ and 0.8 mM Mg$^{2+}$ (↑Ca/Mg, n=6, slope of linear fit is 1.13±0.03), ↑Ca/Mg+w-CgTx (n=8, slope of linear fit is 0.82±0.03)), ↑Ca/Mg+1 mM baclofen (n=10, slope of linear fit is 0.77±0.02), and ↑Ca/Mg+2 nM CCPA (n=6, slope of linear fit is 0.49±0.03). (B) Input-output relationship between stimulation amplitude (delivered at 0.1 Hz) and the slope of fEPSP in slices pretreated for 3 h by control ACSF (n=9, slope of linear fit is 1.13±0.07) or ACSF containing CGP54626 (n=4, 1.13±0.06), ↑Ca/Mg (n=8, 1.18±0.06) or 1 mM baclofen (n=7, 1.25±0.09). Prolong changes in basal neurotransmitter release for 3 hours resulted in homeostasis of synaptic strength in CA3-CA1 connections. (C) Input-output relationship between stimulation amplitude (delivered at 0.1 Hz) and the slope of fEPSP did not differ between WT (n=5, slope of linear fit is 1.01±0.07), APP/PS1 (n=6, 0.99±0.07) and baclofen-treated APP/PS1 (n=4, 0.95±0.06) hippocampal slices.
Figure 5B:
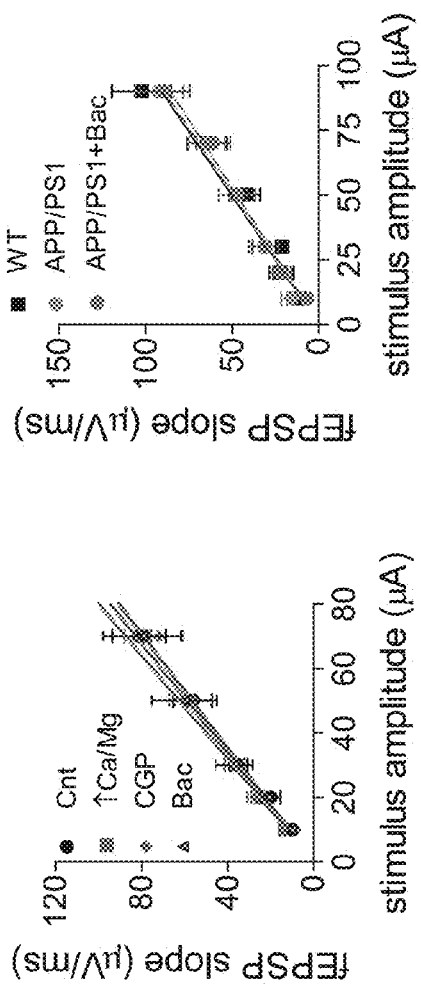

As release of Aβ from presynaptic sites depends on synaptic vesicle recycling, the present inventors evaluated how the properties of synaptic vesicle release affect Aβ40/42. Basal neurotransmitter release determines the filter mode of synapses through regulation of short-term synaptic plasticity[26]. Synapses with low initial release probability typically display facilitation during high-frequency firing, thus functioning as high-pass filters, transmitting bursts while filtering out single spikes. Conversely, synapses with high release probability normally exhibit depression during high-frequency firing, acting as low-pass filters and preferentially transmitting single spikes. First, the basal neurotransmitter release in hippocampal synapses was enhanced (FIG. 4) by increasing the Ca$^{2+}$/Mg$^{2+}$ ratio (↑Ca/Mg) in the ACSF from 1.2/1.2 to 1.6/0.8 mM. The slices were subjected to 1 h stimulations by single spikes or spike bursts (each burst consisted of 5 APs, inter-spike-interval 10 ms, inter-burst interval 5 s) in the modified ACSF. Extracellularly recorded field EPSPs (fEPSPs) evoked by high-frequency spike bursts were used to assess short-term synaptic plasticity in CA3-CA1 hippocampal connections. As expected, ↑Ca/Mg resulted in attenuation of short-term synaptic facilitation (P<0.05, FIGS. 4A-B), indicating an increase in basal neurotransmitter release. The mean charge transfer per action potential ($Q_{fEPSP}$) was calculated by dividing the integral under the fEPSP by the number of spikes. Given the decreased facilitation, the ratio between the $Q_{fEPSP}$ during burst stimulation pattern and single spike pattern was significantly reduced by the ↑Ca/Mg (FIG. 4C). Overall synaptic strength, evaluated by the slope of input (stimulus amplitude)/output (slope of fEPSP) relationship, was increased by ~45% following 1 h stimulation period in ↑Ca/Mg (FIG. 5A).

Next, the present inventors investigated whether the dynamics of the Aβ40 and Aβ42 isoforms was affected by the altered synaptic release properties. Interestingly, ↑Ca/Mg increased by 20% [Aβ40]$_o$ during single spikes, while significantly attenuating the increase in [Aβ40]$_o$ during spike bursts (P<0.05, FIG. 4D). That is, the 'burst-sensitivity' of Aβ40 was reduced with increased basal release probability (FIG. 4F). Notably, ↑Ca/Mg increased by ~30% [Aβ42]$_o$ during either single spikes or spike bursts (P<0.05, FIG. 4E). Therefore, its ratio between bursts and single spike patterns remained unaltered (FIG. 4F). The corollary of these isoform-specific modifications is that synaptic network with stronger basal release and weaker short-term facilitation exhibits lower Aβ40/42 during bursts (FIGS. 4G-H).

In order to understand whether these changes in Aβ40/42 are reversible and can be dynamically regulated by synaptic release properties in the opposite direction, the present inventors induced a reduction in the basal neurotransmitter release in slices incubated in ↑Ca/Mg by (i) direct blocking of presynaptic N-type Ca channels; (ii) activating presynaptic adenosine 1 receptors (A$_1$Rs); or (iii) activating GABA$_B$ receptors (GABA$_B$Rs). Application of either w-conotoxin GVIA (w-CgTx, 2 mM), a specific blocker of N-type Ca channels, A$_1$R agonist CCPA (2 nM), or the GABA$_B$R agonist baclofen (1 mM) during 1 h of stimulation rescued the basal synaptic transmission (FIG. 5A) with consequent increase in short-term synaptic facilitation (FIGS. 4A-C). These reverse changes in synaptic release properties by w-CgTx, CCPA and baclofen were paralleled by changes in the Aβ40/42 dynamics. All these treatments decreased [Aβ40]$_o$ during single spikes, while increasing its concentration during spike bursts (FIG. 4D). Notably, these treatments uniformly reduced [Aβ42]$_o$ during either single- or burst-pattern stimuli periods by 25-30% (FIG. 4E), thus leaving Aβ42 burst/single ratio unaltered (FIG. 4F). Therefore, w-CgTx, CCPA and baclofen increased the burst sensitivity of the Aβ40 isoform, boosting Aβ40/42 during periods of high-frequency burst firing (FIGS. 4G-H). These results suggest that Aβ40/42 dynamically depends on the release properties of hippocampal synapses.

Given that drugs administered in vivo typically display a half-life time in the range of several hours and may trigger homeostatic mechanisms, the long-term (hours) effect of GABA$_B$R agonist regulating short-term synaptic plasticity was examined. Indeed, pretreatment of hippocampal slices with baclofen for 3 h before electrical stimulation did not alter total synaptic strength (FIG. 5B), suggesting homeostatic mechanisms compensating for increase in release probability, while maintaining the synaptic strength in CA3-CA1 connections. Despite the homeostasis of basal synaptic strength, short-term synaptic facilitation and Aβ40 dynamics were augmented during spike bursts, enhancing Aβ40/42 dynamics (FIG. 6). Furthermore, pretreatment of slices with GABA$_B$R antagonist CGP54626 (10 mM, 3 h), disrupting the tonic presynaptic inhibition in Schaffer Collateral synapses[30], resulted in the opposite effect: attenuation of short-term facilitation and Aβ40/42 dynamics due to specific reduction in the burst-evoked [Aβ40]$_o$ (FIG. 6H). Thus, 'burst-sensitivity' of Aβ40/42 dynamics seems to be preserved also under prolonged periods of treatment.

Taken together, these results suggest that the susceptibility of Aβ40/42 to activity patterns is bi-directionally regulated by transmitter release.

Example 3

Regulation of Synaptic and Aβ40/42 Dynamics in an AD Mouse Model

Figure 5C:
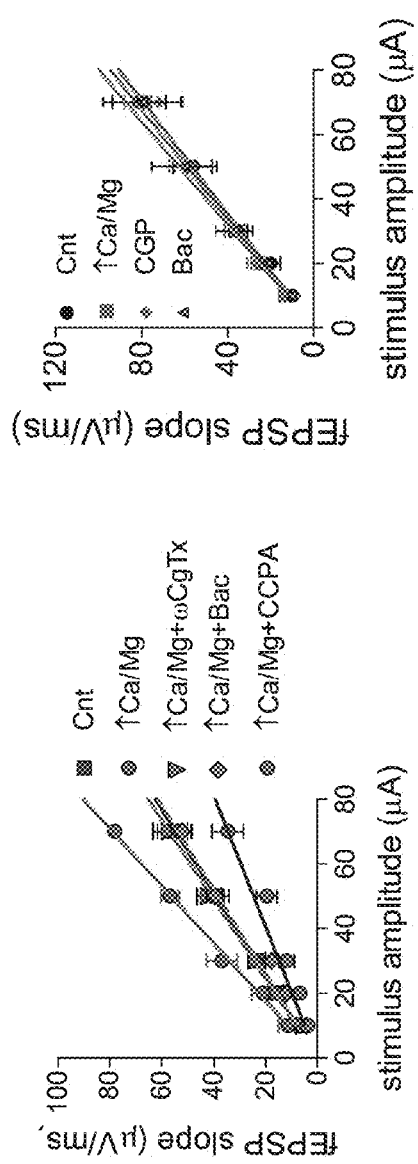
Figure 7B:
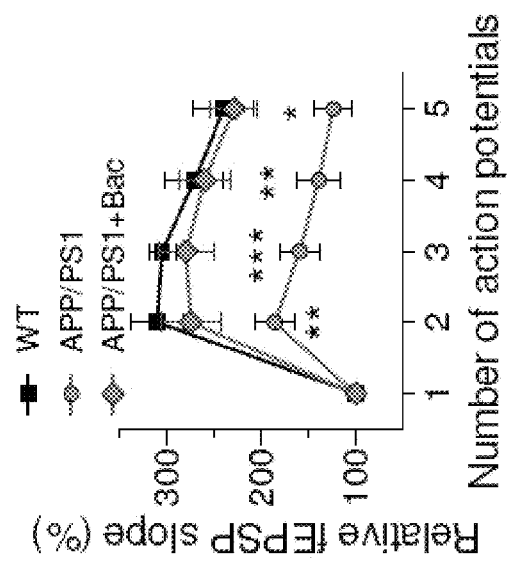
Figure 7A:
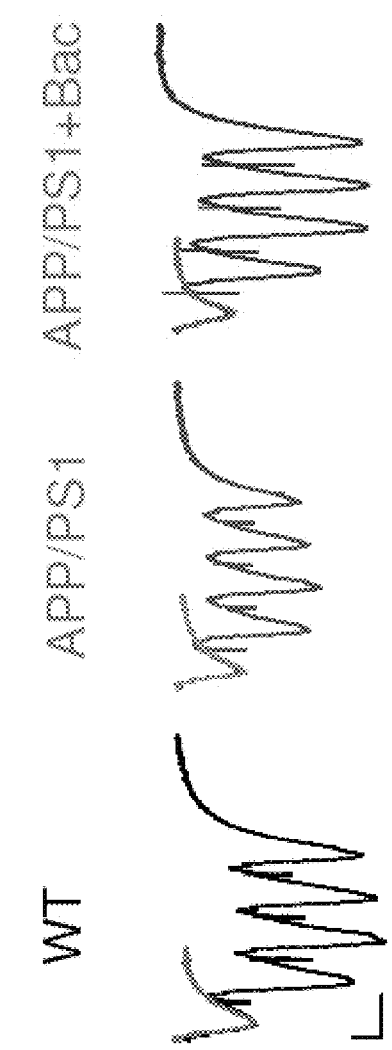

The relationship between synaptic release properties and Aβ40/42 was explored in an animal model of familial AD, APP transgenic mice of the APPswe/PS1dE9 genotype (APP/PS1). Hippocampal slices were taken from 3 months old animals, before the appearance of amyloid plaques[31]. It was found that short-term facilitation in CA3-CA1 connections of APP/PS1 mice was significantly lower than in wild-type (WT) mice (P<0.01, FIGS. 7A-C), while basal synaptic strength was comparable to WT mice (FIG. 5C). Similarly to results obtained in rats (FIG. 1), higher [Aβ40]$_o$ was measured during periods of spike bursts than single spikes in WT mice (P<0.01, FIG. 7D), while [Aβ42]$_o$ did not display sensitivity to the activity pattern (FIG. 7E). Remarkably, in APP/PS1 mice, [Aβ40]$_o$ was higher than in WT during periods of single spikes (P<0.01, FIG. 7D), while it did not differ during periods of spike bursts (P>0.05). [Aβ42]$_o$ was ~2.5-fold higher in hippocampus of APP/PS1 mice, compared with WT, during either burst or single patterns (P<0.001, FIG. 7E). Thus, in APP/PS1 mice, both [Aβ40]$_o$ and [Aβ42]$_o$ were insensitive to the activity pattern (FIG. 7F). The Aβ40/42 ratio in these animals was attenuated (FIG. 7G) and lost its pattern sensitivity (FIG. 7H).

To test if the reduction in Aβ40/42 dynamics in the familial AD model can be rescued by increasing the level of presynaptic inhibition as shown in non-transgenic rats, the effect of baclofen on short-term synaptic plasticity and Aβ molecular composition in APP/PS1 hippocampal slices was analyzed. Pretreatment with baclofen (1 mM, 3 h) rescued the short-term synaptic facilitation in APP/PS1 CA3-CA1 connections (P<0.05, FIGS. 7A-C). Strikingly, baclofen preferentially increased [Aβ40]$_o$ associated with spike bursts (P<0.001, FIG. 7D), while it did not affect [Aβ42]$_o$ (P>0.05, FIG. 7E). As a result of these isoform-specific changes, baclofen restored the pattern sensitivity of Aβ40 (P<0.05, FIG. 7F) and Aβ40/42 augmentation by bursts (P<0.01, FIGS. 7G-H). It is noteworthy that similar results were obtained by two additional ELISA kits for human Aβ40 and Aβ42 (FIG. 8) verifying the reliability of the obtained results. Taken together, these results suggest that FAD-associated mutations do not impair the physiological regulation of Aβ40/42 dynamics by basal neurotransmitter release.

Example 4

Effect of Cadmium Influx on Aβ40 and Aβ42 Dynamics

Figures 9A, 9B, 9C, 9D, 9E:
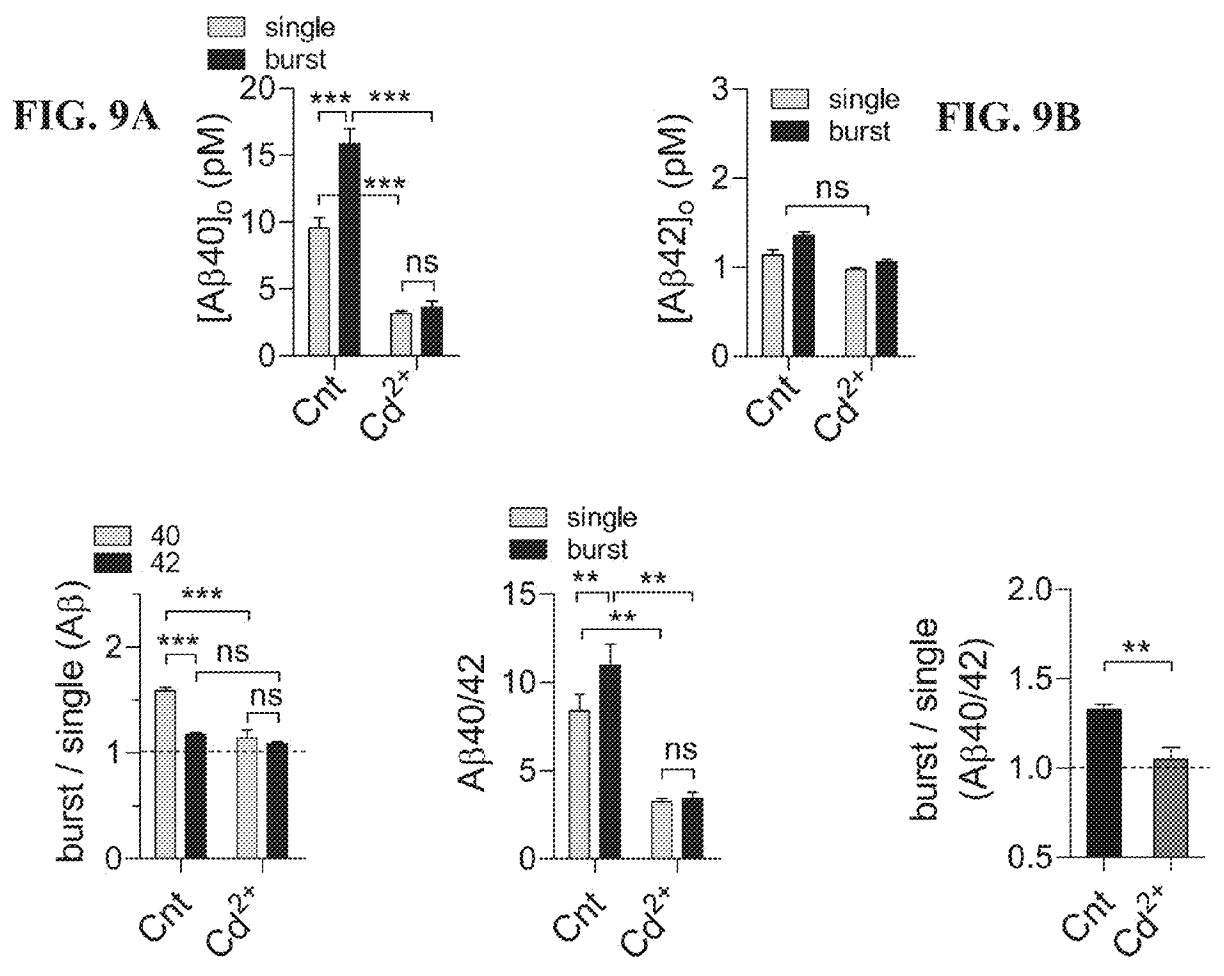

As the data uncovers a correlation between synaptic and Aβ40, but not Aβ42 dynamics, the present inventors asked whether spike-evoked neurotransmitter release differentially regulates the Aβ isoforms. Therefore, synaptic transmission was completely blocked by cadmium, a non-specific blocker of Ca$^{2+}$ influx through voltage-gated calcium channels (VGCCs). Application of 100 μM cadmium reduced [Aβ40]$_o$ by 67% during single spikes and by 77% during spike bursts (p<0.0001, FIG. 9A). Conversely, cadmium did not alter [Aβ42]$_o$ at either stimulation pattern (p>0.1, FIG. 9B). As a result, the pattern-dependency of Aβ40 and, consequently, of Aβ40/42 was abolished (FIG. 9C-E). These results strongly suggest that Ca$^{2+}$ influx through VGCCs and neurotransmitter release are the major regulators of spike-evoked Aβ40, but not of Aβ42 release.

Example 5

Ca$^{2+}$ Accumulation During Bursts Selectively Boosts Aβ40 Release

Next, the present inventors asked whether the release of Aβ40 vs. Aβ42 isoforms during high-frequency bursts displays different dependency on presynaptic Ca$^{2+}$ accumulation, a critical determinant of short-term synaptic facilitation[34-36]. To address this question, the slow Ca$^{2+}$ chelator EGTA was used that can effectively chelate residual Ca$^{2+}$, thus preventing synaptic facilitation due to accumulation of free Ca$^{2+}$ in Schaffer Collateral synapses[37]. Application of the membrane-permeant EGTA-AM at low concentration (50 mM) reduced by 70% synaptic facilitation of excitatory postsynaptic currents (EPSCs) measured by voltage-clamp whole-cell recordings (FIGS. 9G-H), while it reduced EPSCs evoked by single spikes by 20% only (n=9, P<0.05). Notably, EGTA-AM abolished facilitation of Aβ40 by bursts (FIG. 9I), but did not significantly affect [Aβ42]$_o$ levels (FIG. 9J). As a result, Aβ40 burst-sensitivity was impaired, diminishing Aβ40/42 facilitation (FIG. 9K-M). These results suggest that residual Ca$^{2+}$ preferentially regulates [Aβ40]$_o$ by high-frequency bursts, leading to Aβ40/42 facilitation.

Example 6

PS1 Conformation is not Altered by Spiking Patterns

Differences in the production step of Aβ peptides could potentially contribute to the observed isoform-specific, pattern-dependent Aβ regulation. Thus, the effect of neuronal activity on g-secretase cleavage was assessed by examining conformation of Presenilin-1 (PS1), the catalytic subunit in the g-secretase complex, which is responsible for the last step in generation of Aβ species. To analyze conformational changes in PS1 at individual hippocampal synapses as function of neuronal activity in general, and spiking pattern in particular, fluorescent resonance energy transfer (FRET) was used. An intra-molecular CFP-PS1-YFP FRET probe containing CFP at the PS1 N terminus (NT) and YFP in the large cytosolic-loop domain was constructed, on the basis of the reporter engineered by Uemura et al.[38,39] (FIG. 10A). This FRET reporter of PS1 conformation (PS1 NT to loop proximity) reliably predicts changes in the Aβ40/42 ratio[39].

Figure 10C:
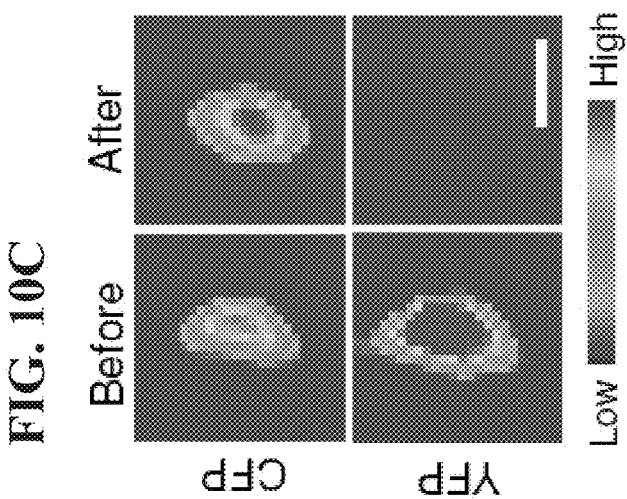
Figure 10B:
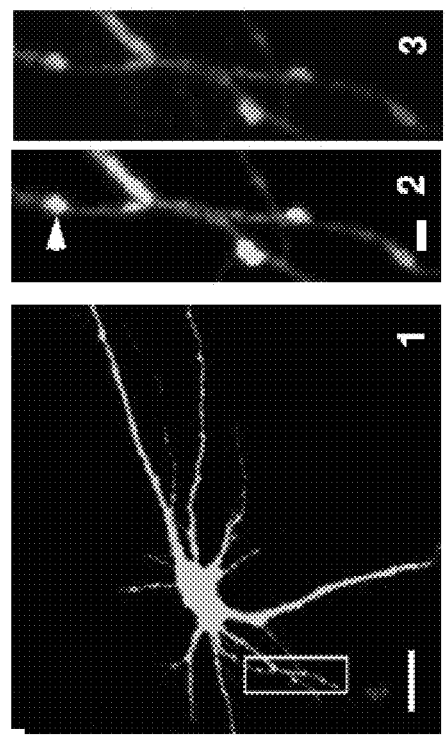
Figure 10A:
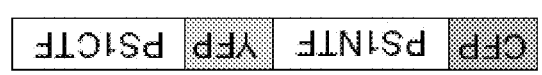
Figure 12B:
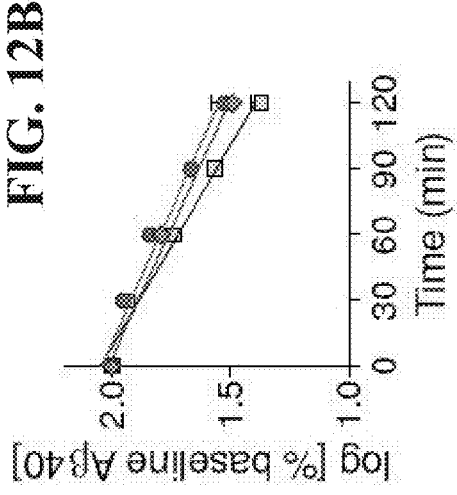
Figure 12D:
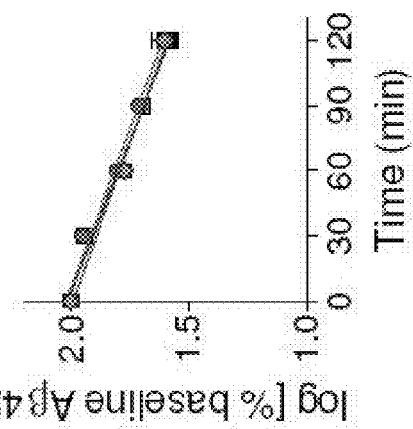
Figure 12A:
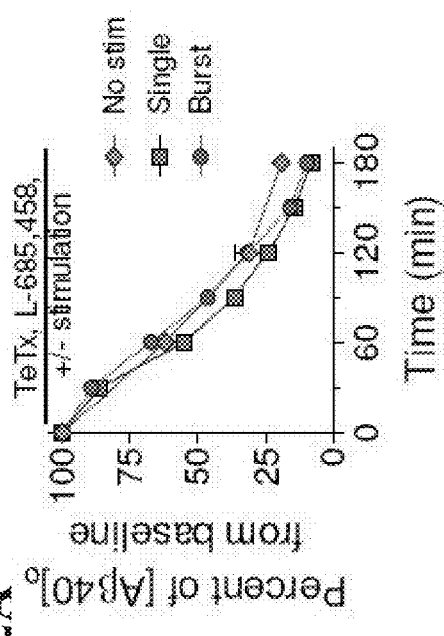
Figure 12C:
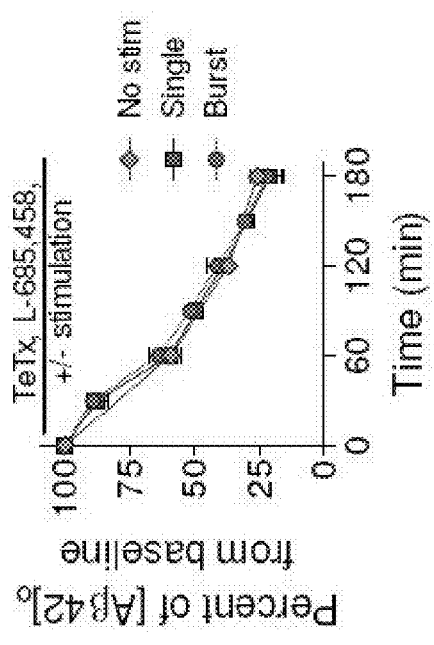
Figure 13A:
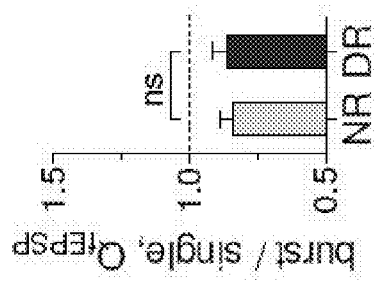
Figure 13B:
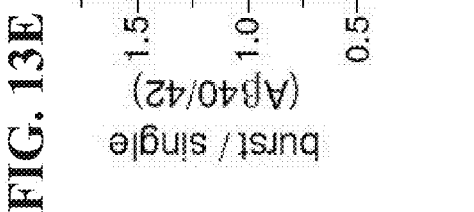
Figure 13C:
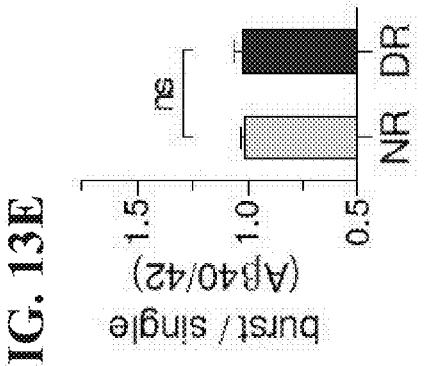
Figure 13D:
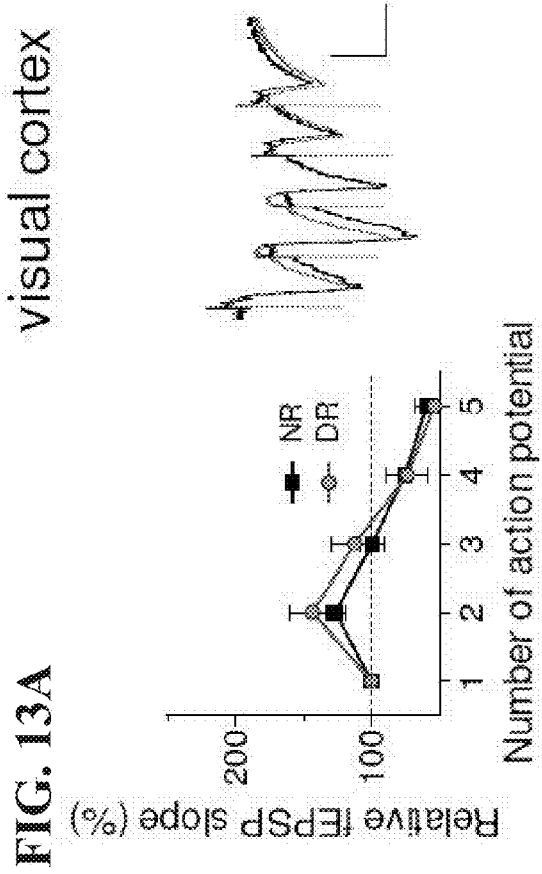
Figure 13E:
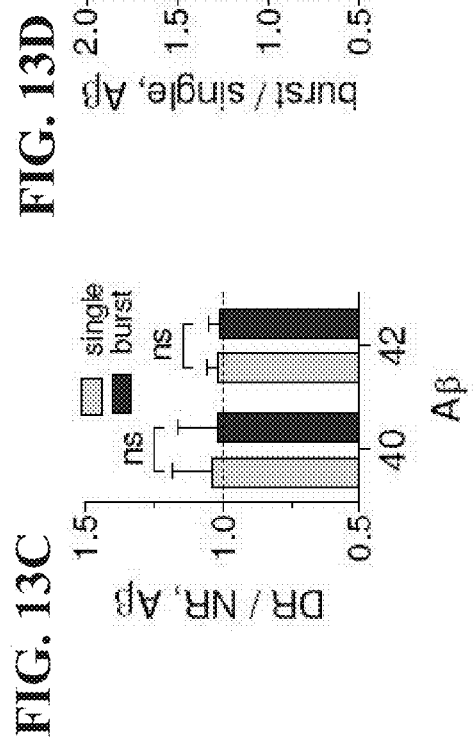

First, the steady-state FRET efficiency (E) was measured utilizing the acceptor photobleaching method at individual synapses[30] in cultured hippocampal neurons expressing CFP-PS1-YFP (FIG. 10B). High-magnification confocal images show an increase in CFP fluorescence after YFP photobleaching (FIG. 10C), indicating dequenching of the donor and the presence of FRET at the bouton marked by arrowhead in FIG. 10B$_2$. On average, CFP-PS1-YFP FRET efficiency across hippocampal boutons was 0.07±0.005 (FIG. 10D), significantly higher (P<0.0001) than the background FRET assessed by photobleaching at 514 nm in neurons expressing PS1 fused only to CFP. Next, the present inventors verified if L166P PS1 FAD mutation, known to lower FRET and Aβ40/

42 ratio in HEK cells[39], increases CFP-PS1-YFP FRET in hippocampal neurons. Indeed, L166P increased CFP-PS1-YFP FRET efficiency by 43% (P<0.001, FIG. 10D).

Having confirmed the sensitivity of CFP-PS1-YFP FRET to changes in the Aβ40/42 ratio, the present inventors tested if FRET depends on the properties of neuronal activity. Blocking spikes by tetrodotoxin (TTX) did not affect mean FRET efficiency (P>0.8, FIG. 10D). To test the TTX effect on FRET at the same population of boutons (i.e. without photobleaching), the ratio of YFP to CFP emission ($F_{YFP}/F_{CFP}$) under CFP excitation before and after TTX application was monitored. TTX did not affect $F_{YFP}/F_{CFP}$ ratio at hippocampal boutons (P>0.4, FIG. 10E). Furthermore, neither increasing mean spike rate from 1 to 5 Hz, nor altering the spike pattern from single spikes to spike bursts, changed the $F_{YFP}/F_{CFP}$ ratio (P>0.5, FIGS. 10F-G). Similar pattern insensitivity was observed in cultures with enhanced short-term facilitation in the presence of 1 mM baclofen (FIG. 10H). These results suggest that the conformation of presynaptic PS1 as estimated by FRET does not depend on the attributes of neuronal activity on a short timescale (1 h). This may be in contrast to activity-dependent, Arc-mediated changes in activity of PS1 at postsynaptic sites that occur on longer time scales[40].

No significant activity-dependent modifications were found in the expression level of full APP, sAPP-a and CTF-a in wild-type hippocampal slices with different basal release probabilities as assessed by Western blot analysis (FIGS. 11A-D). In the same manner, APP processing by β-secretase, estimated by Western blot analysis of CTF-β and full-APP, was not affected by spiking pattern in APP/PS1 slices (FIGS. 11E-G).

Example 7

Aβ Clearance is not Altered by Spiking Patterns

Next, the present inventors determined whether altered clearance of Aβ in the extracellular space contributes to the observed isoform-specific, activity pattern-dependent Aβ regulation. While the lack of TTX effect on elimination rate of total Aβ was observed in vivo[19], the effect of spiking patterns on elimination of Aβ40 and Aβ42 isoforms has not been addressed. Here, Aβ clearance was explored in isolation, following blockade of both secretion and production of Aβ. Thus, half-life time ($t_{1/2}$) for [Aβ40]$_o$ and [Aβ42]$_o$ was examined under different stimulation patterns in hippocampal cultures pretreated by TeTx. Before stimulation, the medium was replaced by the medium from untreated sister cultures and g-secretase inhibitor (L-685,458, 200 nM) was applied. [Aβ40]$_o$ and [Aβ42]$_o$ were measured each half hour during 3 h in three groups of slices: (i) without stimulation, (ii) stimulated by single spikes, (iii) stimulated by spike bursts. The present results demonstrate that $t_{1/2}$ of Aβ40 did not differ between non-stimulated and stimulated slices by either single or burst patterns (67-73 min, n=3-5, P>0.5, FIG. 12A). Similarly, $t_{1/2}$ of Aβ42 did not vary between non-stimulated and stimulated conditions (80-85 min, n=3-5, P>0.4, FIG. 12C). A semi-log plot of baseline concentration versus time was linear for Aβ40 and Aβ42 in all three groups ($r^2$=0.97-0.99, FIG. 12B, D), suggesting first-order kinetics. These results indicate that the elimination kinetics of either Aβ40 or Aβ42 does not depend on neuronal activity.

Example 8

Regulation of Synaptic and Aβ40/42 Dynamics by Sensory Experience

Finally, the biological relevance of Aβ40/42 physiological dynamics was tested by exploring whether it can be regulated by in vivo elicited, experience-dependent synaptic modifications. Since the pioneering studies of Hubel and Wiesel[41], it has been well-documented that neuronal circuits in the primary sensory cortices are shaped by sensory experience during 'critical periods' in early postnatal life. Visual deprivation such as dark rearing prolongs critical period for both ocular dominance and Hebbian-like plasticity[42]. The effects of dark rearing in rats before eye-opening (P8) until the end of critical period (P35-42) were assessed on short-term plasticity of excitatory synaptic connections and dynamics of Aβ40 and Aβ42 isoforms. The biochemical and electrophysiological measurements were performed in primary V1 visual cortex and hippocampus that receives sensory inputs from visual cortex through perirhinal and entorhinal cortex[43]. As has been previously demonstrated[44,45], dark rearing did not alter short-term synaptic plasticity in excitatory synaptic connections of layer 4 to 2/3 visual cortex in P35-42 rats (n=7, P>0.05, FIGS. 13A,B). Similar results were obtained by stimulating layer 6 and recording in layer 2/3 (FIG. 14). Furthermore, dark rearing did not affect dynamics of either Aβ40 or Aβ42 isoform, or the Aβ40/42 ratio in the primary visual cortex at different patterns of neuronal activity (n=7, P>0.05, FIGS. 13C-E).

Unexpectedly, in the hippocampus, dark-reared (DR) rats displayed a pronounced increase in short-term synaptic facilitation in CA3-CA1 pathway comparing to normally-reared (NR) rats (n=8, P<0.01, FIGS. 13F,G). These results suggest that visual deprivation promotes synaptic facilitation by spike bursts in Schaffer Collateral hippocampal synapses. These alterations in hippocampal synaptic dynamics caused by sensory deprivation were paralleled by changes in Aβ40 dynamics similarly to the pharmacological manipulations described above, and [Aβ40]$_o$ was selectively increased during bursts in slices from DR animals (FIG. 13H), while [Aβ42]$_o$ was not altered. Thus Aβ40 displayed stronger burst sensitivity in the hippocampus of DR rats, compared with NR rats (FIG. 13I). That is, hippocampal synapses in DR animals with stronger short-term synaptic facilitation exhibit concurrently Aβ40/42 with higher dynamic range and susceptibility to burst inputs (FIG. 13J).

Example 9

Correlation Between Synaptic and Aβ40/42 Dynamics in Hippocampus

The present data reveal that changes in [Aβ40]$_o$, but not in [Aβ42]$_o$, are strongly correlated with the short-term synaptic facilitation, and are affected by factors modulating synaptic release. It was thus hypothesized that short-term synaptic facilitation is the primary factor underlying increase in Aβ40 dynamics by bursts. To test it, the relationship between the burst/single ratio of Aβ peptides and burst/single ratio of the mean charge transfer per action potential ($Q_{fEPSP}$) per individual animal was plotted across all the experimental conditions (FIGS. 15A, B). It can be seen from these plots that $Q_{fEPSP}$ burst/single ratio in CA3-CA1 connections varies considerably among animals and between groups with different history of synaptic activation (n=73, FIGS. 15A-C). Strikingly however, it significantly correlated with Aβ40 dynamics per individual animal (Spearman r=0.80, P<0.0001, FIG. 15A). In contrast, no correlation was observed between synaptic and Aβ42 dynamics (Spearman r=0.22, P>0.05, FIG. 15B). As a consequence of the differential regulation of Aβ40 and Aβ42 isoforms, $Q_{EPSP}$ burst/single ratio strongly correlated with Aβ40/42 dynamics among animals (Spearman r=0.80, P<0.0001, FIG. 15C). Thus, short-term synaptic plasticity in excitatory hippocampal synaptic connections was correlated with Aβ40/42 augmentation by bursts per individual animal. Given that $Q_{EPSP}$ linearly correlates with the number of released synaptic vesicles[35], the present data indicate that the release of Aβ40 is dependent on the total number of released vesicles.

Discussion

Accumulation and aggregation of the Aβ peptide in the extracellular space of distinct brain regions is a pathological hallmark of Alzheimer's disease. For several decades, scientists have searched for the mechanisms regulating cerebral Aβ oligomerization and subsequent aggregation. While numerous FAD-linked mutations leading to reduction in the Aβ40/42 ratio through over-production of the more pathogenic Aβ42 isoform have been discovered[13-15], how experience regulates Aβ40/42 dynamics remains largely unresolved. In this study, the present inventors have examined regulation of Aβ40 and Aβ42 peptides by spiking patterns, release properties of synapses and sensory deprivation. They find that the extracellular concentration of Aβ40, but not that of Aβ42, is strongly regulated by synaptic release dynamics reflecting activity patterns, while no evidence was found for differential effect of activity patterns on either the production or the elimination steps. Hence, in contrast to the many FAD mutations, the present work highlights Aβ40 isoform as the key determinant of experience-dependent Aβ40/42 dynamics in hippocampal circuits.

Burst as a Positive Regulator of Aβ40/42

The data reveal a critical role for the temporal pattern of afferent input in Aβ40/42 regulation. Increase in the mean rate or number of single spikes at low frequencies uniformly augment the extracellular Aβ40 and Aβ42 levels. Conversely, keeping the mean rate constant with concomitant change in the temporal spiking pattern via a shift from single spikes to spike bursts preferentially increases $[Aβ40]_o$. Bursts at constant frequencies≥20 Hz and 'natural' burst patterns boost Aβ40 without significant changes in the Aβ42 level. Thus, spike bursts, playing a central role in synaptic plasticity and memory encoding[25,26], represent a basic feature determining Aβ40/42 ratio in hippocampal circuits.

Aβ40 Dynamics Reflects Short-Term Synaptic Plasticity

Is Aβ40/42 dynamics solely determined by the characteristics of neuronal input or is it also affected by synaptic properties of the neuron? An inverse relationship between changes in the basal release probability which determines short-term synaptic plasticity and Aβ40 dynamics was observed, but no such correlation exists with Aβ42. Remarkably, this relationship was maintained across hippocampal circuits with different synaptic release properties, including those with FAD-associated mutations (FIGS. 15A-C).

The present inventors asked whether the effect of higher levels of endogenously released Aβ during bursts saturate, thus preventing further increase of release probability. Indeed, application of Aβ40 in neurons lacking Aβ production due to BACE-1 inhibition uncovered an increase in presynaptic strength during bursts (FIG. 16). Thus, increase in endogenously released Aβ40 during bursts is involved in facilitation of presynaptic activity.

Figure 15D:
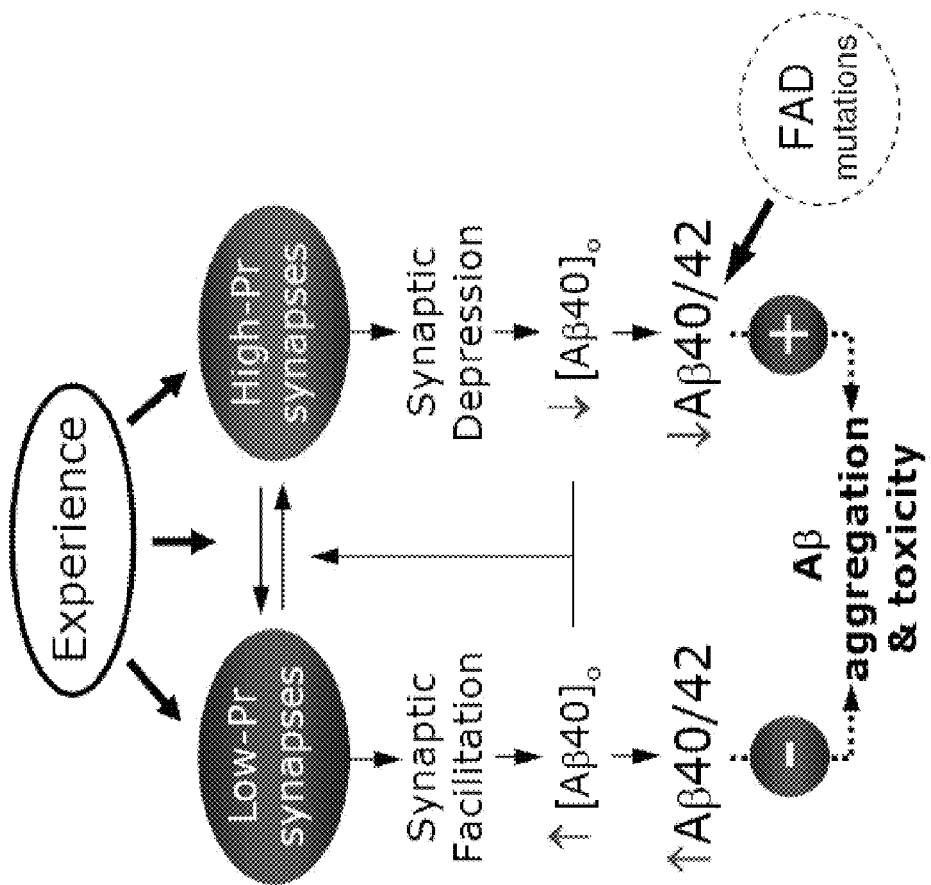

Taken together, the data imply regulation of Aβ quality by the properties of synaptic filter (FIG. 15D). Synaptic circuits with lower release probability, optimized for efficient burst transfer, exhibit increased Aβ40/42 augmentation by bursts and thus broader Aβ40/42 dynamic range. Conversely, synaptic circuits with higher release probability optimized for the transfer of single spikes are characterized by short-term synaptic depression and reduced Aβ40/42.

Synaptic Vesicle Exocytosis at the Active Zone Mediates Spike-Evoked Aβ Release

To date, the exact mechanism that couples synaptic activity and Aβ release at presynaptic terminals remains unresolved. Early studies reported that APP is internalized with recycling synaptic vesicle membrane proteins, but sorted away from synaptic vesicles to Rab5-containing endocytic organelles[46,47]. Subsequent APP proteolytic processing in endosomes generates Aβ[48,49] which may be released as function of synaptic vesicle recycling[19,20]. According to this model, synaptic vesicle exocytosis enhances Aβ generation and subsequent release from exosomes due to increase in APP endocytosis at the plasma membrane. On the other hand, recent studies, utilizing super-resolution microscopy, EM and biochemistry suggest the presence of g-secretase complex components, Aβ40 and APP also in a fraction of synaptic vesicles[50,51]. These findings, together with the predominant role of synaptic vesicle recycling in neurons, lead to the hypothesis that synaptic vesicle release may represent a major activity-dependent exocytotic pathway of APP derivatives[51].

While a prominent block of Aβ release by TeTx-dependent synaptic vesicle exocytosis has been demonstrated (Ref. 19 and FIGS. 9A,B), it is still unclear whether block of the fusion of synaptic vesicles or of endosome-like structures underlies TeTx-induced inhibition of Aβ release. The targets of TeTx cleavage, VAMP2/3 SNAREs, are present at synaptic vesicles as well as at early and recycling endosomes[32] and have also been implicated in constitutive exocytosis[52]. Therefore, the present inventors searched for a molecular perturbation that specifically inhibits synaptic vesicle release at the presynaptic active zone. So far, only five active zone enriched protein families have been identified: Munc13s, RIMs, Basson and Piccolo/Aczonin, ELKSs, and α-liprins (for reviews see[53,54]). Munc13-1 and Munc13-2 are the only Munc13 isoforms co-expressed in hippocampal boutons and constitute essential components of the synaptic vesicle priming apparatus in glutamatergic and GABAergic synapses[33]. Double knockout Munc13-1/2 neurons in culture (Munc13-DKO) are morphologically normal with unaltered synaptogenesis and no detectable changes in membrane protein localization, indicating that constitutive secretory processes are not affected substantially by the loss of Munc13-1 and Munc13-2. However, Munc13-DKO neurons entirely lack both evoked and spontaneous synaptic vesicle release[33], which makes them an ideal model to selectively study the role of synaptic vesicle exocytosis in Aβ secretion. The present data show that spontaneous Aβ secretion was only partially reduced in the DKO mice (FIG. 9E), indicating that constitutive secretory processes, including exosome-mediated secretion, may also contribute to activity-independent Aβ release. In contrast, both single spike- and burst-evoked Aβ40 and Aβ42 release were almost completely abolished in the DKO mice (FIG. 9C, D). Thus, it may be concluded that the activity-dependent Aβ route of release follows synaptic vesicle exocytosis at the active zone, letting one presume that the difference observed between Aβ release evoked by burst vs. single spikes should reside in a differential regulation of the synaptic vesicle exocytosis path.

What could be the possible mechanisms underlying selective regulation of $[Aβ40]_o$, but not of $[Aβ42]_o$, by bursts? Possible differences in $Ca^{2+}$-dependency of Aβ40 vs. Aβ42 release may explain a uniform increase in $[Aβ40]_o$ and $[Aβ42]_o$ by single spikes, but preferential increase in $[Aβ40]_o$ by bursts. Indeed, both [Aβ40]$_o$ and [Aβ42]$_o$ were sensitive to modulations of presynaptic Ca$^{2+}$ flux evoked by single spikes (FIG. 4E), but only [Aβ40]$_o$ depended on the intracellular Ca$^{2+}$ accumulation during bursts (FIG. 9I, J), indicating that Aβ42 secretion may saturate at lower Ca$^{2+}$ levels. Moreover, the Aβ isoforms may exhibit different presynaptic localization in various functional pools of synaptic vesicles and/or endosomes. It is well-established that low-frequency spikes typically recruit synaptic vesicles from the readily releasable pool, while short, high-frequency spike bursts trigger exocytosis of synaptic vesicles form the recycling pool[55]. Given a higher Aβ40 release during bursts, recycling vesicles may contain higher Aβ40/42 ratio than vesicles in the readily releasable pool undergoing endosomal sorting[56]. High-resolution methods are needed to unequivocally determine where in presynaptic compartment Aβ isoforms are localized and what is the exact mechanism leading to differential Aβ40 vs. Aβ42 release by bursts.

Sensory Deprivation Enhances Aβ40/42 Dynamics in Hippocampus

Sporadic, late-onset AD represents the most common form of dementia. Influence of everyday experience on AD susceptibility and development in humans[57,58] and transgenic FAD mouse models[59,60] have been proposed long time ago. Physical and cognitive stimulations by means of environmental enrichment, if introduced at the early stages preceding memory decline in a FAD mouse model, increases the Aβ40/Aβ42 ratio[61]. However, the mechanisms underlying experience-dependent Aβ40/42 regulation remain obscure. It is well accepted that sensory experience modifies cortical circuitry by inducing use-dependent changes in synapses[62]. Thus, based on the present in vitro data, it was hypothesized that modulations of sensory experience might co-regulate the properties of synaptic filter and the Aβ40/42 ratio in vivo. Visual deprivation during the 'critical period' of cortical plasticity was used, a well-studied model of experience-dependent synaptic modifications in the visual cortex[63,64]. Strikingly, dark rearing increased short-term synaptic facilitation and Aβ40 dynamics in hippocampus, while it did not affect either glutamate release or Aβ molecular composition in intracortical connections of V1 (FIG. 13). Importantly, Aβ42 dynamics was not susceptible to visual deprivation. As sensory information converges on the entorhinal cortex which then projects directly to the CA1 and dentate gyrus regions of the hippocampus, changes in the hippocampal CA3-CA1 pathway are likely to be caused by spread of activity changes from the perforant pathway. The lack of change in synaptic release functions in V1 following DR is in agreement with recent findings[44,45], and can serve as an internal control for the link between shifts in short-term synaptic plasticity and Aβ40.

Given an inverse correlation between the Aβ40/42 ratio and amyloid formation and toxicity[8-10], the present results provide a possible mechanism for region-specific, activity-dependent local Aβ aggregation[65]. Finally, these results propose that changes in sensory experience, recorded in hippocampal synapses as increase in short-term synaptic facilitation, may cause Aβ40/42 augmentation, slowing the progression of β-amyloidosis (FIG. 15D). Indeed, long-term whisker deprivation reduces amyloid plaque growth and new plaque formation in the barrel cortex of APP/PS1 mice[65] possibly due to deprivation-induced reduction in glutamate release probability[66]. As Aβ is more effective at low-release probability synapses during single spikes[28], high-frequency bursts may protect synaptic function by two mechanisms: through increase in the Aβ40/42 ratio and reduction in the responsiveness of presynaptic boutons to high Aβ levels.

Ageing is the highest risk factor for the most common, late-onset sporadic AD. Given that magnesium intake[67], A$_1$R density[68] and GABA$_B$R binding[69] all decline with age, future studies are needed to explore whether increase in the basal release probability might contribute to Aβ40/42 attenuation in sporadic AD. Co-regulation of glutamate and Aβ40 dynamics by experience highlights a potential role for changes in synaptic transfer function in disease development and offers novel therapeutic and conceptual insights to prevent Aβ40/42 decline in the most common, sporadic Alzheimer's disease.

Example 10

Regulation of Aβ40 and Aβ42 Isoforms by Temporal Pattern of Stimulation in Human Brain Slices Having established dependency of Aβ40/42 dynamics on synapse release probability in hippocampal slices of wild-type rats, mice and transgenic APP/PS1 mice AD model, the present inventors assessed the relevance of their findings to human brain tissue. For this reason, they examined the correlation between synaptic facilitation and Aβ40/42 dynamics in human hippocampal and cortical tissues from patients with brain tumors. Human slices were subjected to 1 hour stimulations by single spikes or spike bursts as described for experiments in rodents herein above (each burst contains 5 APs, inter-spike-interval 10 ms, inter-burst interval 5 s) in ACSF in the presence of 50 μM AP-5 for blocking postsynaptic excitatory NMDA receptors. Following stimulation, [Aβ40]$_o$ and [Aβ42]$_o$ in ACSF were measured by sandwich ELISA. Extracellularly recorded field EPSPs (fEPSPs) were used to assess short-term synaptic plasticity.

Similar to rodents, CA3-CA1 hippocampal connections display a pronounced degree of facilitation in human slices (FIGS. 17A-B). The Aβ40/42 ratio was about 10:1 under basal conditions (FIG. 17E). Both [Aβ40]$_o$ and [Aβ42]$_o$ showed no significance increase following bursts stimulation in control slices (FIGS. 17C-D), resulting in the lack of Aβ40/42 pattern sensitivity (FIGS. 17E-F). In order to examine whether Aβ40/42 dynamics is regulated by synaptic release probability, basal neurotransmitter release was reduced by baclofen, a selective agonist of GABA$_B$Rs, as in the rodent experiments, herein above. Addition of 20 μM RS-baclofen resulted in an increase of short-term synaptic facilitation (FIGS. 17A-B). [Aβ40]$_o$ decreased by baclofen, whereas the degree of inhibition was higher during single spikes (FIG. 17C). Notably, baclofen inhibited [Aβ42]$_o$ equally during single spikes and spike bursts (FIG. 17D). As a result, baclofen increased Aβ40 (FIG. 17F<0.001) and Aβ40/42 (FIGS. 17E and 17G p<0.05) burst/single ratio. Taken together, the results obtained from human hippocampal slices confirm that increase in synaptic facilitation by baclofen augments Aβ40/42 dynamics during spike bursts due to selective 'burst-sensitivity' of the Aβ40 isoform.

Next, the relationship between synaptic release properties and Aβ40/42 dynamics was examined in human cortices. fEPSPs evoked by spike bursts revealed a strong depression that has been decreased by baclofen (FIGS. 18A-C). Notably, baclofen significantly increased Aβ40 burst/single ratio (FIG. 18C, p<0.05; FIG. 18F, p<0.001), without affecting Aβ42 (FIG. 18D, F). As a result, baclofen increased Aβ40/42 pattern dependency (FIG. 18H, p<0.05).

In summary, the data in human hippocampal and cortical tissue validate the basic principles of Aβ40/42 regulation by synapse release probability and propose increase in synaptic facilitation as a potential treatment for prevention of synaptic and cognitive decline in AD.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Haass, C. & Selkoe, D. J. Soluble protein oligomers in neurodegeneration: lessons from the Alzheimer's amyloid beta-peptide. *Nat Rev Mol Cell Biol* 8, 101-12 (2007).
2. Palop, J. J. & Mucke, L. Amyloid-beta-induced neuronal dysfunction in Alzheimer's disease: from synapses toward neural networks. *Nat Neurosci* 13, 812-8 (2010).
3. Haass, C. et al. Amyloid beta-peptide is produced by cultured cells during normal metabolism. *Nature* 359, 322-5 (1992).
4. Seubert, P. et al. Isolation and quantification of soluble Alzheimer's beta-peptide from biological fluids. *Nature* 359, 325-7 (1992).
5. Shoji, M. et al. Production of the Alzheimer amyloid beta protein by normal proteolytic processing. *Science* 258, 126-129 (1992).
6. De Strooper, B. & Annaert, W. Proteolytic processing and cell biological functions of the amyloid precursor protein. *J Cell Sci* 113 (Pt 11), 1857-70 (2000).
7. Haass, C. Take five—BACE and the gamma-secretase quartet conduct Alzheimer's amyloid beta-peptide generation. *Embo J* 23, 483-8 (2004).
8. Jarrett, J. T., Berger, E. P. & Lansbury, P. T., Jr. The carboxy terminus of the beta amyloid protein is critical for the seeding of amyloid formation: implications for the pathogenesis of Alzheimer's disease. *Biochemistry* 32, 4693-7 (1993).
9. Hasegawa, K., Yamaguchi, I., Omata, S., Gejyo, F. & Naiki, H. Interaction between A beta(1-42) and A beta(1-40) in Alzheimer's beta-amyloid fibril formation in vitro. *Biochemistry* 38, 15514-21 (1999).
10. Kuperstein, I. et al. Neurotoxicity of Alzheimer's disease Abeta peptides is induced by small changes in the Abeta42 to Abeta40 ratio. *Embo J* 29, 3408-20 (2010).
11. Kim, J. et al. $A^2$40-Inhibits Amyloid Deposition In Vivo. *The Journal of Neuroscience* 27, 627-633 (2007).
12. Bertram, L., Lill, C. M. & Tanzi, R. E. The Genetics of Alzheimer Disease: Back to the Future. *Neuron* 68, 270-281 (2010).
13. Suzuki, N. et al. An increased percentage of long amyloid beta protein secreted by familial amyloid beta protein precursor (beta APP717) mutants. *Science* 264, 1336-40 (1994).
14. Duff, K. et al. Increased amyloid-beta42(43) in brains of mice expressing mutant presenilin 1 *Nature* 383, 710-3 (1996).
15. Scheuner, D. et al. Secreted amyloid beta-protein similar to that in the senile plaques of Alzheimer's disease is increased in vivo by the presenilin 1 and 2 and APP mutations linked to familial Alzheimer's disease. *Nat Med* 2, 864-70 (1996).
16. Ashe, K. H. & Zahs, K. R. Probing the biology of Alzheimer's disease in mice. *Neuron* 66, 631-45 (2010).
17. Brouwers, N., Sleegers, K. & Van Broeckhoven, C. Molecular genetics of Alzheimer's disease: an update. *Ann Med* 40, 562-83 (2008).
18. Kamenetz, F. et al. APP processing and synaptic function. *Neuron* 37, 925-37 (2003).
19. Cirrito, J. R. et al. Synaptic activity regulates interstitial fluid amyloid-beta levels in vivo. *Neuron* 48, 913-22 (2005).
20. Cirrito, J. R. et al. Endocytosis is required for synaptic activity-dependent release of amyloid-beta in vivo. *Neuron* 58, 42-51 (2008).
21. Kang, J. E. et al. Amyloid-beta dynamics are regulated by orexin and the sleep-wake cycle. *Science* 326, 1005-7 (2009).
22. Buxbaum, J. D. et al. Alzheimer amyloid protein precursor in the rat hippocampus: transport and processing through the perforant path. *J Neurosci* 18, 9629-37 (1998).
23. Harris, J. A. et al. Transsynaptic progression of amyloid-beta-induced neuronal dysfunction within the entorhinal-hippocampal network. *Neuron* 68, 428-41 (2010).
24. Wei, W. et al. Amyloid beta from axons and dendrites reduces local spine number and plasticity. *Nat Neurosci* (2009).
25. Lisman, J. E. Bursts as a unit of neural information: making unreliable synapses reliable. *Trends Neurosci* 20, 38-43 (1997).
26. Abbott, L. F. & Regehr, W. G. Synaptic computation. *Nature* 431, 796-803 (2004).
27. Tsodyks, M. V. & Markram, H. The neural code between neocortical pyramidal neurons depends on neurotransmitter release probability. *Proc Natl Acad Sci USA* 94, 719-23 (1997).
28. Abramov, E. et al. Amyloid-[beta] as a positive endogenous regulator of release probability at hippocampal synapses. *Nat Neurosci* 12, 1567-1576 (2009).
29. Zheng, H. et al. beta-Amyloid precursor protein-deficient mice show reactive gliosis and decreased locomotor activity. *Cell* 81, 525-31 (1995).
30. Laviv, T. et al. Basal GABA regulates GABA(B)R conformation and release probability at single hippocampal synapses. *Neuron* 67, 253-67 (2010).
31. Jankowsky, J. L. et al. Mutant presenilins specifically elevate the levels of the 42 residue beta-amyloid peptide in vivo: evidence for augmentation of a 42-specific gamma secretase. *Human Molecular Genetics* 13, 159-170 (2004).
32. Proux-Gillardeaux, V., Rudge, R. & Galli, T. The tetanus neurotoxin-sensitive and insensitive routes to and from the plasma membrane: fast and slow pathways? *Traffic* 6, 366-73 (2005).
33. Varoqueaux, F. et al. Total arrest of spontaneous and evoked synaptic transmission but normal synaptogenesis in the absence of Munc13-mediated vesicle priming. *Proceedings of the National Academy of Sciences* 99, 9037-9042 (2002).
34. Katz, B. & Miledi, R. The role of calcium in neuromuscular facilitation. *J Physiol* 195, 481-92 (1968).
35. Zucker, R. S. & Regehr, W. G. Short-term synaptic plasticity. *Annu Rev Physiol* 64, 355-405 (2002).

36. Neher, E. & Sakaba, T. Multiple roles of calcium ions in the regulation of neurotransmitter release. *Neuron* 59, 861-72 (2008).
37. Blatow, M., Caputi, A., Burnashev, N., Monyer, H. & Rozov, A. Ca2+ Buffer Saturation Underlies Paired Pulse Facilitation in Calbindin-D28k-Containing Terminals. *Neuron* 38, 79-88 (2003).
38. Uemura, K. et al. Substrate docking to gamma-secretase allows access of gamma-secretase modulators to an allosteric site. *Nat Commun* 1, 130 (2011).
39. Uemura, K. et al. Allosteric modulation of PS1/gamma-secretase conformation correlates with amyloid beta(42/40) ratio. *PLoS One* 4, e7893 (2009).
40. Wu, J. et al. Arc/Arg3.1 regulates an endosomal pathway essential for activity-dependent beta-amyloid generation. *Cell* 147, 615-28 (2011).
41. Hubel, D. H. & Wiesel, T. N. Receptive Fields of Cells in Striate Cortex of Very Young, Visually Inexperienced Kittens. *J Neurophysiol* 26, 994-1002 (1963).
42. Kirkwood, A., Lee, H. K. & Bear, M. F. Co-regulation of long-term potentiation and experience-dependent synaptic plasticity in visual cortex by age and experience. *Nature* 375, 328-31 (1995).
43. Suzuki, W. A. & Amaral, D. G. Topographic organization of the reciprocal connections between the monkey entorhinal cortex and the perirhinal and parahippocampal cortices. *J Neurosci* 14, 1856-77 (1994).
44. Philpot, B. D., Sekhar, A. K., Shouval, H. Z. & Bear, M. F. Visual experience and deprivation bidirectionally modify the composition and function of NMDA receptors in visual cortex. *Neuron* 29, 157-69 (2001).
45. Cheetham, C. E. J. & Fox, K. The role of sensory experience in presynaptic development is cortical area specific. *The Journal of Physiology* 589, 5691-5699 (2011).
46. Ikin, A. F. et al. Alzheimer Amyloid Protein Precursor Is Localized in Nerve Terminal Preparations to Rab5-containing Vesicular Organelles Distinct from Those Implicated in the Synaptic Vesicle Pathway. *Journal of Biological Chemistry* 271, 31783-31786 (1996).
47. Marquez-Sterling, N. R., Lo, A. C. Y., Sisodia, S. S. & Koo, E. H. Trafficking of Cell-Surface Beta-Amyloid Precursor Protein: Evidence that a Sorting Intermediate Participates in Synaptic Vesicle Recycling. *The Journal of Neuroscience* 17, 140-151 (1997).
48. Lah, J. J. & Levey, A. I. Endogenous presenilin-1 targets to endocytic rather than biosynthetic compartments. *Mol Cell Neurosci* 16, 111-26 (2000).
49. Vassar, R. et al. Beta-secretase cleavage of Alzheimer's amyloid precursor protein by the transmembrane aspartic protease BACE. *Science* 286, 735-41 (1999).
50. Frykman, S. et al. Synaptic and endosomal localization of active gamma-secretase in rat brain. *PLoS One* 5, e8948 (2010).
51. Groemer, T. W. et al. Amyloid precursor protein is trafficked and secreted via synaptic vesicles. *PLoS One* 6, e18754 (2011).
52. Oishi, Y. et al. Role of VAMP-2, VAMP-7, and VAMP-8 in constitutive exocytosis from HSY cells. *Histochem Cell Biol* 125, 273-81 (2006).
53. Rosenmund, C., Rettig, J. & Brose, N. Molecular mechanisms of active zone function. *Curr Opin Neurobiol* 13, 509-19 (2003).
54. Schoch, S. & Gundelfinger, E. D. Molecular organization of the presynaptic active zone. *Cell Tissue Res* 326, 379-91 (2006).
55. Rizzoli, S. O. & Betz, W. J. Synaptic vesicle pools. *Nat Rev Neurosci* 6, 57-69 (2005).
56. Hoopmann, P. et al. Endosomal sorting of readily releasable synaptic vesicles. *Proceedings of the National Academy of Sciences* 107, 19055-19060 (2010).
57. Katzman, R. Education and the prevalence of dementia and Alzheimer's disease. *Neurology* 43, 13-20 (1993).
58. Stern, Y. et al. Influence of education and occupation on the incidence of Alzheimer's disease. *Jama* 271, 1004-10 (1994).
59. Jankowsky, J. L. et al. Environmental Enrichment Mitigates Cognitive Deficits in a Mouse Model of Alzheimer's Disease. *J. Neurosci.* 25, 5217-5224 (2005).
60. Lazarov, O. et al. Environmental Enrichment Reduces A[beta] Levels and Amyloid Deposition in Transgenic Mice. *Cell* 120, 701-713 (2005).
61. Herring, A. et al. Preventive and therapeutic types of environmental enrichment counteract beta amyloid pathology by different molecular mechanisms. *Neurobiol Dis* 42, 530-8 (2011).
62. Katz, L. C. & Shatz, C. J. Synaptic activity and the construction of cortical circuits. *Science* 274, 1133-8 (1996).
63. Hensch, T. K. Critical period plasticity in local cortical circuits. *Nat Rev Neurosci* 6, 877-88 (2005).
64. Smith, G. B., Heynen, A. J. & Bear, M. F. Bidirectional synaptic mechanisms of ocular dominance plasticity in visual cortex. *Philos Trans R Soc Lond B Biol Sci* 364, 357-67 (2009).
65. Bero, A. W. et al. Neuronal activity regulates the regional vulnerability to amyloid-beta deposition. *Nat Neurosci* 14, 750-6 (2011).
66. Bender, K. J., Allen, C. B., Bender, V. A. & Feldman, D. E. Synaptic Basis for Whisker Deprivation-Induced Synaptic Depression in Rat Somatosensory Cortex. *The Journal of Neuroscience* 26, 4155-4165 (2006).
67. Ford, E. S. & Mokdad, A. H. Dietary magnesium intake in a national sample of U.S. adults. *J Nutr* 133, 2879-82 (2003).
68. Deckert, J. r. et al. Loss of human hippocampal adenosine A1 receptors in dementia: evidence for lack of specificity. *Neuroscience Letters* 244, 1-4 (1998).
69. Turgeon, S. M. & Albin, R. L. GABAB binding sites in early adult and aging rat brain. *Neurobiol Aging* 15, 705-11 (1994).
70. Slutsky, I., Sadeghpour, S., Li, B. & Liu, G. Enhancement of synaptic plasticity through chronically reduced Ca2+ flux during uncorrelated activity. *Neuron* 44, 835-49 (2004).
71. Laviv, T. et al. Compartmentalization of the GABAB Receptor Signaling Complex Is Required for Presynaptic Inhibition at Hippocampal Synapses. *The Journal of Neuroscience* 31, 12523-12532 (2011).

What is claimed is:

1. A method of treating Alzheimer's disease (AD) in a subject in need thereof, the method comprising:
   (a) electrically stimulating a nerve pathway in a brain region of the subject with at least two high frequency spike bursts of electrical currents, wherein a pattern of said high frequency spike bursts is a natural burst pattern of a healthy subject; and
   (b) administering to the subject an agent selected from the group consisting of a $GABA_B$ receptor agonist, an $A_1$ receptor agonist, a metabotropic glutamate receptors group II agonist, an $M_2$ muscarinic agonist, a $CB_1$ endocannabinoid receptor agonist, Mu opioid receptor agonist, a voltage-dependent antagonist of voltage-gated calcium channels.

2. The method of claim 1, wherein said electrically stimulating is effected at the entorhinal cortex.

3. The method of claim 1, wherein said brain region comprises a hippocampus.

4. The method of claim 1, wherein said natural burst pattern of a healthy subject is a hippocampal natural burst pattern.

5. The method of claim 4, wherein said hippocampal natural burst pattern is set forth in Table 1.

6. The method of claim 1, wherein said electrically stimulating does not affect the permeability of the blood brain barrier (BBB).

7. The method of claim 1, wherein said administering is effected prior to said stimulating.

8. The method of claim 1, wherein said administering is effected following said stimulating.

9. The method of claim 1, wherein said administering is effected concomitant with said stimulating.

10. The method of claim 1, wherein a dose of said agent is selected such that it lowers synaptic transmission of low frequency pulses in the brain to a greater extent than high frequency bursts.

11. The method of claim 1, wherein said $GABA_B$ receptor agonist is selected from the group consisting of baclofen, CGP44532 and CGP35024.

12. The method of claim 1, wherein said $A_1$ receptor agonist is selected from the group consisting of 2-Chloro-N-cyclopentyladenosine (CCPA), N-Cyclopentyladenosine (CPA), N-Bicyclo[2.2.1]hept-2-yl-5'-chloro-5'-deoxyadenosine (ENBA), N-[1S,2S)-2-Hydroxycyclopentyl]adenosine, and 2-Chloro-N-cyclopentyl-2'-methyladenosine.

13. The method of claim 1, wherein said metabotropic glutamate receptor group II agonist is selected from the group consisting of (1R,4R,5S,6R)-4-Amino-2-oxabicyclo[3.1.0]hexane-4,6-dicarboxylic acid (LY379268),(1S,2S,5R,6S)-2-Aminobicyclo[3.1.0]hexane-2,6-dicarboxylic acid (LY35474), (2R,4R)-4-Aminopyrrolidine-2,4-dicarboxylate and (2S,1'S,2'S)-2-(Carboxycyclopropyl)glycine (L-CCG-I).

14. The method of claim 1, wherein said $CB_1$ endocannabinoid receptor agonist is selected from the group consisting of N-(2-Chloroethyl)-5Z,8Z,11Z,14Z-eicosatetraenamide (ACEA), N-(Cyclopropyl)-5Z,8Z,11Z,14Z-eicosatetraenamide (ACPA), rel-5-(1,1-Dimethylheptyl)-2-[(1R,3S)-3-hydroxycyclohexyl] phenol (CP47497) and N-(2-Hydroxyethyl)-7Z,10Z,13Z,16Z-docosatetraenamide.

15. The method of claim 1, wherein a dose of said agent is selected such that it lowers synaptic transmission of low frequency pulses in the brain to a greater extent than high frequency bursts.

16. A method of treating AD in a subject in need thereof, the method comprising administering to the subject a therapeutically effective amount of an agent selected from the group consisting of a $GABA_B$ receptor agonist, an $A_1$ receptor agonist, a metabotropic glutamate receptors group II agonist, an $M_2$ muscarinic agonist, a $CB_1$ endocannabinoid receptor agonist, Mu opioid receptor agonist, a voltage-dependent antagonist of voltage-gated calcium channels and a calcium chelator wherein a dose of said agent is selected such that it lowers synaptic transmission of low frequency pulses in the brain to a greater extent than high frequency bursts.

17. A method of selecting a stimulator useful for the treatment of AD, the method comprising:
   (a) contacting brain cells with the stimulator; and
   (b) determining an amount of Aβ40 in said brain cells, wherein an increase in an amount of Aβ40 following said contacting is indicative of a stimulator useful for the treatment of AD.

18. The method of claim 17, wherein said stimulator comprises an electrical stimulator.

19. The method of claim 17, wherein said stimulator comprises a pharmacological stimulator.

20. The method of claim 17, further comprising determining an amount of Aβ42 in said brain cells following step (a), wherein an increase in Aβ40: Aβ42 is indicative of stimulant useful for the treatment of AD.

21. The method of claim 19, wherein said contacting is effected for about 3 hours.

22. A method of treating Alzheimer's disease (AD) in a subject in need thereof, the method comprising:
   (a) electrically stimulating a nerve pathway in a brain region of the subject with at least two high frequency spike bursts of electrical currents, said bursts comprising between 2-20 spikes, wherein a frequency of said spikes in said bursts is between 5-200 msec; and (b) administering to the subject an agent selected from the group consisting of a GABA$_B$ receptor agonist, an A$_1$ receptor agonist, a metabotropic glutamate receptors group II agonist, an M$_2$ muscarinic agonist, a CB$_1$ endocannabinoid receptor agonist and a Mu opioid receptor agonist.

23. The method of claim 22, wherein said GABA$_B$ receptor agonist is selected from the group consisting of baclofen, CGP44532 and CGP35024.

24. The method of claim 22, wherein said A$_1$ receptor agonist is selected from the group consisting of 2-Chloro-N-cyclopentyladenosine (CCPA), N-Cyclopentyladenosine (CPA), N-Bicyclo[2.2.1]hept-2-yl-5'-chloro-5'-deoxyadenosine (ENBA), N-[(1S,2S)-2-Hydroxycyclopentyl]adenosine, and 2-Chloro-N-cyclopentyl-2'-methyladenosine.

25. The method of claim 22, wherein said metabotropic glutamate receptor group II agonist is selected from the group consisting of (1R,4R,5S,6R)-4-Amino-2-oxabicyclo[3.1.0]hexane-4,6-dicarboxylic acid (LY379268),(1S,2S,5R,6S)-2-Aminobicyclo[3.1.0]hexane-2,6-dicarboxylic acid (LY35474), (2R,4R)-4-Aminopyrrolidine-2,4-dicarboxylate and (2S,1'S,2'S)-2-(Carboxycyclopropyl)glycine (L-CCG-I).

26. The method of claim 22, wherein said CB$_1$ endocannabinoid receptor agonist is selected from the group consisting of N-(2-Chloroethyl)-5Z,8Z,11Z,14Z-eicosatetraenamide (ACEA), N-(Cyclopropyl)-5Z,8Z,11Z,14Z-eicosatetraenamide (ACPA), rel-5-(1,1-Dimethylheptyl)-2-[(1R,3S)-3-hydroxycyclohexyl] phenol (CP47497) and N-(2-Hydroxyethyl)-7Z,10Z,13Z,16Z-docosatetraenamide.

27. The method of claim 22, wherein a dose of said agent is selected such that it lowers synaptic transmission of low frequency pulses in the brain to a greater extent than high frequency bursts.

* * * * *

SEQUENCE LISTING

<160> NUMBER OF SEQ ID NOS: 5

<210> SEQ ID NO 1
<211> LENGTH: 3416
<212> TYPE: DNA
<213> ORGANISM: Homo sapiens

```
<400> SEQUENCE: 1
gctgactcgc ctggctctga gccccgccgc cgcgctcggg ctccgtcagt ttcctcggca      60
gcggtaggcg agagcacgcg gaggagcgtg cgcggggggcc ccgggagacg cggcggtgg     120 cggcgcgggc agagcaagga cgcggcggat cccactcgca cagcagcgca ctcggtgccc    180
cgcgcagggt cgcgatgctg cccggtttgg cactgctcct gctggccgcc tggacggctc    240
gggcgctgga ggtacccact gatggtaatg ctggcctgct ggctgaaccc cagattgcca    300
tgttctgtgg cagactgaac atgcacatga atgtccagaa tgggaagtgg gattcagatc    360
catcagggac caaaacctgc attgatacca aggaaggcat cctgcagtat tgccaagaag    420
tctaccctga actgcagatc accaatgtgg tagaagccaa ccaaccagtg accatccaga    480
actggtgcaa gcggggccgc aagcagtgca agacccatcc ccactttgtg attccctacc    540
gctgcttagt tggtgagttt gtaagtgatg cccttctcgt tcctgacaag tgcaaattct    600
tacaccagga gaggatggat gtttgcgaaa ctcatcttca ctggcacacc gtcgccaaag    660
agacatgcag tgagaagagt accaacttgc atgactacgg catgttgctg ccctgcggaa    720
ttgacaagtt ccgaggggta gagtttgtgt gttgcccact ggctgaagaa agtgacaatg    780
tggattctgc tgatgcggag gaggatgact cggatgtctg gtggggcgga gcagacacag    840
actatgcaga tgggagtgaa gacaaagtag tagaagtagc agaggaggaa gaagtggctg    900
aggtggaaga agaagaagcc gatgatgacg aggacgatga ggatggtgat gaggtagagg    960
aagaggctga ggaaccctac gaagaagcca cagagagaac caccagcatt gccaccacca   1020
ccaccaccac cacagagtct gtggaagagg tggttcgagt tcctacaaca gcagccagta   1080
cccctgatgc cgttgacaag tatctcgaga cacctgggga tgagaatgaa catgcccatt   1140
tccagaaagc caaagagagg cttgaggcca agcaccgaga gagaatgtcc caggtcatga   1200
gagaatggga agaggcagaa cgtcaagcaa agaacttgcc taaagctgat aagaaggcag   1260
ttatccagca tttccaggag aaagtggaat ctttggaaca ggaagcagcc aacgagagac   1320
agcagctggt ggagacacac atggccagag tggaagccat gctcaatgac cgccgccgcc   1380
tggccctgga gaactacatc accgctctgc aggctgttcc tcctcggcct cgtcacgtgt   1440
tcaatatgct aaagaagtat gtccgcgcag aacagaagga cagacagcac accctaaagc   1500
atttcgagca tgtgcgcatg gtggatccca gaaaagccgc tcagatccgg tcccaggtta   1560
tgacacacct ccgtgtgatt tatgagcgca tgaatcagtc tctctcccotg ctctacaacg   1620 tgcctgcagt ggccgaggag attcaggatg aagttgatga gctgcttcag aaagagcaaa   1680
actattcaga tgacgtcttg gccaacatga ttagtgaacc aaggatcagt tacggaaacg   1740
atgctctcat gccatctttg accgaaacga aaaccaccgt ggagctcctt cccgtgaatg   1800
gagagttcag cctggacgat ctccagccgt ggcattcttt tgggggctgac tctgtgccag   1860 ccaacacaga aaacgaagtt gagcctgttg atgcccgccc tgctgccgac cgaggactga   1920
ccactcgacc aggttctggg ttgacaaata tcaagacgga ggagatctct gaagtgaaga   1980
tggatgcaga attccgacat gactcaggat atgaagttca tcatcaaaaa ttggtgttct   2040
ttgcagaaga tgtgggttca aacaaaggtg caatcattgg actcatggtg ggcggtgttg   2100
tcatagcgac agtgatcgtc atcaccttgg tgatgctgaa gaagaaacag tacacatcca   2160
ttcatcatgg tgtggtggag gttgacgccg ctgtcacccc agaggagcgc cacctgtcca   2220
agatgcagca gaacggctac gaaaatccaa cctacaagtt ctttgagcag atgcagaact   2280 agaccccccgc cacagcagcc tctgaagttg gacagcaaaa ccattgcttc actacccatc   2340
```

```
ggtgtccatt tatagaataa tgtgggaaga acaaacccg ttttatgatt tactcattat    2400
cgccttttga cagctgtgct gtaacacaag tagatgcctg aacttgaatt aatccacaca    2460
tcagtaatgt attctatctc tctttacatt ttggtctcta tactacatta ttaatgggtt    2520
ttgtgtactg taaagaattt agctgtatca aactagtgca tgaatagatt ctctcctgat    2580
tatttatcac atagccccttt agccagttgt atattattct tgtggtttgt gacccaatta    2640
agtcctactt tacatatgct ttaagaatcg atggggatg cttcatgtga acgtgggagt     2700
tcagctgctt ctcttgccta agtattcctt tcctgatcac tatgcatttt aaagttaaac    2760
atttttaagt atttcagatg ctttagagag attttttttc catgactgca ttttactgta    2820
cagattgctg cttctgctat atttgtgata taggaattaa gaggatacac acgtttgttt    2880
cttcgtgcct gttttatgtg cacacattag gcattgagac ttcaagcttt tcttttttg     2940 tccacgtatc tttgggtctt tgataaagaa aagaatccct gttcattgta agcacttta    3000 cggggcgggt ggggagggt gctctgctgg tcttcaatta ccaagaattc tccaaaacaa     3060
ttttctgcag gatgattgta cagaatcatt gcttatgaca tgatcgcttt ctacactgta    3120
ttacataaat aaattaaata aaataacccc gggcaagact tttctttgaa ggatgactac    3180
agacattaaa taatcgaagt aattttgggt ggggagaaga ggcagattca attttcttta    3240
accagtctga agtttcattt atgatacaaa agaagatgaa aatggaagtg gcaatataag    3300
gggatgagga aggcatgcct ggacaaaccc ttcttttaag atgtgtcttc aatttgtata    3360
aaatggtgtt ttcatgtaaa taaatacatt cttggaggag caaaaaaaaa aaaaaa       3416

<210> SEQ ID NO 2
<211> LENGTH: 120
<212> TYPE: DNA
<213> ORGANISM: Homo sapiens

<400> SEQUENCE: 2
gatgcagaat tccgacatga ctcaggatat gaagttcatc atcaaaaatt ggtgttcttt     60
gcagaagatg tgggttcaaa caaaggtgca atcattggac tcatggtggg cggtgttgtc    120

<210> SEQ ID NO 3
<211> LENGTH: 40
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 126
<212> TYPE: DNA
<213> ORGANISM: Homo sapiens

<400> SEQUENCE: 4
gatgcagaat tccgacatga ctcaggatat gaagttcatc atcaaaaatt ggtgttcttt     60
gcagaagatg tgggttcaaa caaaggtgca atcattggac tcatggtggg cggtgttgtc    120
atagcg                                                              126
```

```
<210> SEQ ID NO 5
<211> LENGTH: 42
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```